(12) United States Patent
McElroy et al.

(10) Patent No.: US 6,750,379 B2
(45) Date of Patent: Jun. 15, 2004

(54) HOMOLOGOUS RECOMBINATION-MEDIATED TRANSGENE ALTERATIONS IN PLANTS

(75) Inventors: David McElroy, Redwood City, CA (US); David A. Walters, North Stonington, CT (US); Larry A. Gilbertson, Chesterfield, MO (US)

(73) Assignee: DeKalb Genetics Corporation, DeKalb, IL (US)

( * ) Notice: Subject to any disclaimer, the term of this patent is extended or adjusted under 35 U.S.C. 154(b) by 0 days.

(21) Appl. No.: 09/801,261

(22) Filed: Mar. 7, 2001

(65) Prior Publication Data

US 2001/0056583 A1 Dec. 27, 2001

Related U.S. Application Data

(63) Continuation-in-part of application No. 09/521,557, filed on Mar. 9, 2000, now Pat. No. 6,580,019.

(51) Int. Cl.[7] .................. C12N 15/82; C12N 15/31; A01H 1/00
(52) U.S. Cl. .................. 800/278; 800/275; 800/260; 800/288; 800/300; 800/306; 800/312; 800/314; 800/317.2; 800/320; 800/320.1; 800/320.2; 800/320.3
(58) Field of Search ............... 800/260, 275, 800/278, 288, 300, 306, 312, 314, 317.2, 320, 320.1, 320.2, 320.3

(56) References Cited

U.S. PATENT DOCUMENTS

| | | | |
|---|---|---|---|
| 4,535,060 A | 8/1985 | Comai | 435/172.3 |
| 4,959,317 A | 9/1990 | Sauer | 435/172.3 |
| 5,134,074 A | 7/1992 | Gordon et al. | 435/240.4 |
| 5,254,801 A | 10/1993 | Dotson et al. | 800/205 |
| 5,276,268 A | 1/1994 | Strauch et al. | 800/205 |
| 5,302,523 A | 4/1994 | Coffee et al. | 435/172.1 |
| 5,322,783 A | 6/1994 | Tomes et al. | 435/172.1 |
| 5,384,253 A | 1/1995 | Krzyzek et al. | 435/172.3 |
| 5,464,765 A | 11/1995 | Coffee et al. | 435/172.3 |
| 5,482,852 A | 1/1996 | Yoder et al. | 435/172.3 |
| 5,489,520 A | 2/1996 | Adams et al. | 435/172.3 |
| 5,508,184 A | 4/1996 | Negrutiu et al. | 435/172.3 |
| 5,508,468 A | 4/1996 | Lundquist et al. | 800/205 |
| 5,538,877 A | 7/1996 | Lundquist et al. | 435/172.3 |
| 5,538,880 A | 7/1996 | Lundquist et al. | 435/172.3 |
| 5,550,318 A | 8/1996 | Adams et al. | 800/205 |
| 5,563,055 A | 10/1996 | Townsend et al. | 435/172.3 |
| 5,590,390 A | 12/1996 | Maarschalkerweerd | 422/186.3 |
| 5,591,616 A | 1/1997 | Hiei et al. | 435/172.3 |
| 5,610,042 A | 3/1997 | Chang et al. | 435/172.3 |
| 5,627,061 A | 5/1997 | Barry et al. | 438/172.3 |
| 5,654,182 A | 8/1997 | Wahl et al. | 435/172.1 |
| 5,658,772 A | 8/1997 | Odell et al. | 435/172.3 |
| 5,723,765 A | 3/1998 | Oliver et al. | 800/205 |
| 5,780,708 A | 7/1998 | Lundquist et al. | 800/205 |
| 5,792,924 A | 8/1998 | Yoder et al. | 800/205 |
| 5,801,030 A | 9/1998 | McVey et al. | 435/172.3 |
| 5,876,988 A | 3/1999 | Selten et al. | 435/172.3 |
| 5,929,307 A | 7/1999 | Hodges et al. | 800/303 |
| 6,051,431 A | 4/2000 | Selten et al. | 435/465 |

FOREIGN PATENT DOCUMENTS

| | | | |
|---|---|---|---|
| EP | 0154204 | 9/1985 | C12N/15/00 |
| EP | 0911412 | 4/1999 | |
| WO | 92/17598 | 10/1992 | C12N/15/82 |
| WO | 97/04103 | 2/1997 | C12N/15/54 |
| WO | WO 97/13401 | * 4/1997 | |
| WO | 97/26366 | 7/1997 | C12N/15/82 |
| WO | WO 01/21780 | 3/2001 | |
| WO | WO 01/96583 | 12/2001 | |

OTHER PUBLICATIONS

Lee et al. The Plant Cell 2(5): 415–425, May 1990.*
Conner et al., "Meiotic stability of transgene expression is unaffected by flanking matrix–associated regions." *Molecular Breeding*. 4(1):47–58. 1997.
Fischer et al., "Selectable marker recycling in the chloroplast." *Mol. Gen. Genet.*, 251:373–380. 1996. No. 3.
Iamtham and Day. "Removal of anitbiotic resistance genes from transgenic tobacco plastids," *Nature Biotechnology*. 18:1172–1176. 2000.
Yoder and Goldsbrough. "Transformation systems for generating marker–free transgenic plants." *Bio/Technology*. 12:263–267. 1994.
Abdullah, R., et al., "Efficient Plant Regeneration From Rice Protoplasts Through Somatic Embryogenesis", *Bio/Technology*, 4, pp. 1087–1090, (Dec. 1986).
Assaad, F.F., et al., "Somatic and Germinal Recombination of a Direct Repeat in Arabidopsis", *Genetics*, 132, pp. 553–566, (Oct. 1992).
Bates, G.W., "Genetic Transformation of Plants by Protoplasts Electroporation", *Molecular Biotechnology*, 2, pp. 135–145, (1994).
Battraw, M., et al., "Stable transformation of Sorghum bicolor protoplasts with chimeric neomycin phosphotransferase II and β–glucuronidase genes", *Theoretical and Applied Genetics*, 82, pp. 161–168, (1991).
Bhattacharjee, B., et al., "Fertile transgenic Indica Rice Produced by Expression of Maize Ubiquitin Promoter–bar Chimaeric Gene in the Protoplasts", *J. Plant Biochemistry & Biotechnology*, 6, pp. 69–73, (Jul. 1997).
Ghosh Biswas, G.C., et al., "Transgenic Indica rice (*Oryza sativa* L.) plants obtained by direct gene transfer to protoplasts", *Journal of Biotechnology*, 32, pp. 1–10, (1994).

(List continued on next page.)

*Primary Examiner*—David T. Fox
(74) *Attorney, Agent, or Firm*—Fulbright & Jaworski L.L.P.

(57) ABSTRACT

The invention provides a process to prepare a recombined transgenic *Zea mays* plant from a transgenic *Zea mays* plant, wherein the transgene in the recombinant plant has an altered genetic structure relative to the genetic structure of the transgene in the transgenic plant, due to homologous recombination-mediated transgene deletion, amplification or rearrangement.

14 Claims, 13 Drawing Sheets

OTHER PUBLICATIONS

Bower, R., et al., "Transgenic sugarcane plants via mircoprojectile bombardment", *The Plant Journal*, 2 (*3*), pp. 409–416, (1992).

Buising, C.M., et al., "Molecular analysis of transgenic plants generated by microprojectile bombardment: effect of petunia transformation booster sequence", *Mol. Gen. Genet.*, *243*, pp. 71–81, (1994).

Callis, J., et al., "Introns Increase Gene Expression in Cultured Maize Cells", *Genes and Development*, *1*, pp. 1183–1200, (1987).

Casas, A.M., et al., "Transgenic Sorghum Plants via Microprojectile Bombardment", *PNAS USA*, *90*, pp. 11212–11216, (Dec. 1993).

Christou, P., et al., "Stable transformation of soybean by electroporation and root formation from transformed callus", *PNAS*, *84*, pp. 3962–3966, (Jun. 1987).

Czako, M., et al., "The Herpes Simplex Virus Thymidine Kinase Gene as a Conditional Negative–Selection Marker Gene in *Arabidopsis thaliana*", *Plant Physiol.*, *104*, pp. 1067–1071, (1994).

D'Halluin, K., et al., "Transgenic Maize Plants by Tissue Electroporation", *The Plant Cell*, *4*, pp. 1495–1505, (Dec. 1992).

De Block, M., et al., "Engineering Herbicide Resistance in Plants by Expression of a Detoxifying Enzyme", *EMBO J.*, *6* (*9*), pp. 2513–2518, (1987).

De Block, M., et al., "Transformation of *Brassica napus* and *Brassica oleracea* Using *Agrobacterium tumefaciens* and the Expression of the bar and neo Genes in the Transgenic Plants", *Plant Physiol.*, *91*, pp. 694–701, (1989).

Dellaporta, S.L., et al., "Molecular Cloning of the Maize R–nj Allele by Transposon Tagging with Ac", *In: Chromosome Structure and Function: Impact of New Concepts*, Plenum Press, New York: Gustafson, J.P., et al., (Eds.), pp. 263–282, (1988).

Depicker, A.G., et al., "A Negative Selection Scheme for Tobacco Protoplast–Derived Cells Expressing the T–DNA Gene 2", *Plant Cell Reports*, *7*, pp. 63–66, (1988).

Dotson, S.B., et al., "A phosphonate monoester hydrolase from *Burkholderia caryophilli* PG2982 is useful as a conditional lethal gene in plants", *The Plant Journal*, *10* (*2*), pp. 383–392, (1996).

Dotson, S.B., et al., "Identification, Characterization, and Cloning of a Phosphonate Monoester Hydrolase from *Burkholderia caryophilli* PG2982", *The Journal of Biological Chemistry*, *271* (*42*), pp. 25754–25761, (Oct. 18, 1996).

Evans, D.A., et al., "Chapter 18: Mitotic Crossing–over in Higher Plants", *In: Plant Cell and Tissue Culture Principles and Applications*, W.R. Sharp, et al., (Eds.), Ohio State University Press: Columbus, pp. 315–351, (1979).

Fedoroff, N.V., "Chapter 1: Controlling Elements in Maize", *In: Mobile Genetic Elements*, Academic Press: James A. Shapiro, (Ed.), pp. 1–63, (1983).

Fraley, R.T., et al., "The SEV System: A New Disarmed TI Plasmid Vector System For Plant Transformation", *Bio/Technology*, *3*, pp. 629–635, (Jul. 1985).

Fromm, M.E., et al., "Stable Transformation of Maize after Gene Transfer by Electroporation", *Nature*, *319*, pp. 791–793, (Feb. 27, 1986).

Gal, S., et al., "Genomic homologous recombination in planta", *The EMBO J.*, *10* (*6*), pp. 1571–1578, (1991).

Hardy, S., et al., "Construction of Adenovirus Vectors through Cre–lox Recombination", *Journal of Virology*, *71* (*3*), pp. 1842–1849, (Mar. 1997).

He, D.G., et al., "Transformation of wheat (*Triticum aestivum* L.) through electroporation of protoplasts", *Plant Cell Reports*, *14*, pp. 192–196, (1994).

Hensgens, L.A., et al., "Transient and stable expression of gusA fusions with rice genes in rice, barley and perennial ryegrass", *Plant Molecular Biology*, *22*, pp. 1101–1127, (1993).

Hiei, Y., et al., "Transformation of rice mediated by *Agrobacterium tumefaciens*", *Plant Molecular Biology*, *35*, pp. 205–218, (1997).

Hinchee, M.A., et al., "Production of Transgenic Soybean Plants Using Agrobacterium–Mediated DNA Transfer", *Bio/Technology*, *6*, pp. 915–922, (Aug. 1988).

Hou, B., et al., "Rapid Optimization of Electroporation Conditions for Soybean and Tomato Suspension Cultured Cells", *Plant Physiology, Supp. 2, V. 111*, Abstract No. 781, p. 166, (Jun. 1996).

Ikuta, N., et al., "The α–Amylase Gene as a Marker for Gene Coloning: Direct Screening of Recombinant Clones", *Bio/Technology*, *8*, pp. 241–242, (Mar. 1990).

Ishida, Y., et al., "High efficiency transformation of maize (*Zea mays* L.) mediated by *Agrobacterium tumefaciens*", *Nature Biotechnology*, *14*, pp. 745–750, (Jun. 1996).

Jelesko, J.G., et al., "Rare germinal unequal crossing–over leading to recombinant gene formation and gene duplication in *Arabidopsis thaliana*", *PNAS*, *96*, pp. 10302–10307, (Aug. 1999).

Kaeppler, H.F., et al., "Silicon Carbide Fiber–Mediated DNA Delivery into Plant Cells", *Plant Cell Reports*, *9*, pp. 415–418, (1990).

Katz, E., et al., "Cloning and Expression of the Tyrosinase Gene from *Streptomyces antibioticus* in *Streptomyces lividans*", *J. of General Microbiology*, *129*, pp. 2703–2714, (1983).

Knittel, N., et al., "Transformation of sunflower (*Helianthus annuus* L.): a reliable protocol", *Plant Cell Reports*, *14*, pp. 81–86, (1994).

Laursen, C.M., et al., "Production of Fertile Transgenic Maize by Electroporation of Suspension Culture Cells", *Plant Mol. Biol.*, *24*, pp. 51–61, (1994).

Lazzeri, P.A., "Chapter 7: Stable Transformatin of Barley via Direct DNA Uptake", *In: Methods in Molecular Biology: Plant Gene Transfer and Expression Protocols*, Humana Press, Inc., Totowa, New Jersey: Heddwyn Jones, (Ed.), pp. 95–106, (1995).

Lee, J.S., et al., "Gene Transfer into Intact Cells of Tobacco by Electroporation", *Korean J. Genetics*, *11–2*, pp. 65–72, (1989).

Lorz, H., et al., "Gene Transfer to Cereal Cells Mediated by Protoplast Transformation", *Mol. Gen. Genet.*, *199*, pp. 178–182, (1985).

Marcotte, W.R., et al., "Regulation of a wheat promoter by abscisic acid in rice protoplasts", *Nature*, *335*, pp. 454–457, (Sep. 29, 1988).

McCabe, D.E., et al., "Transformation of Elite Cotton Cultivars via particle Bombardment of Meristems", *Bio/Technology*, *11*, pp. 596–598, (May 11, 1993).

McCormac, A.C., et al., "The use of visual marker genes as cell–specific reporters of Agrobacterium–mediated T–DNA delivery to wheat (*Triticum aestivum* L.) and barley (*Hordeum vulgare* L.)", *Euphytica*, *99*, pp. 17–25, (1998).

Murakami, T., et al., "The Bialaphos Biosynthetic Genes of *Streptomyces hygroscopicus*: Molecular Cloning and Characterization of the Gene Cluster", *Mol. Gen. Genet., 205*, pp. 42–50, (1986).

Niedz, R.P., et al., "Gren fluorescent protein: an in vivo reporter of plant gene expression", *Plant Cell Reports, 14*, pp. 403–406, (1995).

Omirulleh, S., et al., "Activity of a chimeric promoter with the doubled CaMV 35S enhancer element in protoplast-–derived cells and transgenic in maize", *Plant Molecular Biology, 21*, pp. 415–428, (1993).

Ow, D.W., et al., "Transient and Stable Expression of the Firefly Luciferase Gene in Plant Cells and Transgenic Plants", *Science 234*, pp. 856–859, (Nov. 14, 1986).

Peterhans, A., et al., "Intrachromosomal recombination in plants", *The EMBO J., 9 (11)*, pp. 3437–3445, (1990).

Phi–Van, L., et al., "The Chicken Lysozyme 5' matrix Attachment Region Increases Transcription from a Heterologous Promoter in Heterologous Cells and Dampens Position Effects on the Expression of Transfected Genes", *Molecular and Cellular Biology, 10 (5)*, pp. 2302–2307, (May 1990).

Potrykus, I., et al., "Direct Gene Transfer to Cells of a Graminaceous Monocot", *Mol. Gen. Genet., 199*, pp. 183–188, (1985).

Prasher, D., et al., "Cloning and Expression of the cDNA Coding for Aequorin, A Bioluminescent Calcium–Binding Protein", *Biochem. Biophys. Res. Commun., 126 (3)*, pp. 1259–1268, (1985).

Reiss, B., et al., "RecA protein stimulates homologous recombination in plants", *PNAS, 93*, pp. 3094–3098, (Apr. 1996).

Rhodes, C.A., et al., "Chapter 9: Transformation of Maize by Electroporation of Embryos", *In: Methods in Molecular Biology: Plant Cell Electroporation and Electrofusion Protocols*, J.A. Nickoloff, (Ed.): Humana Press, Totowa, New Jersey, pp. 121–131, (1995).

Ritala, A., et al., "Fertile transgenic barley by particle bombardment of immature embryos", *Plant Molecular Biology, 24*, pp. 317–325, (1994).

Robbins, T.P., et al., "Meiotic Instability of the R–r Complex Arising From Displaced Intragenic Exchange and Intrachromosomal Rearrangement", *Genetics, 129*, pp. 271–283, (Sep. 1991).

Rogers, S.G., et al., "Chapter 15: Improved Vectors for Plant Transformation: Expression Cassette Vectors and New Selectable Markers", *In: Methods in Enzymology, V.153: Recombinant DNA, Part D*, Academic Press, Inc.: Ray Wu, et al., (Eds.), pp. 253–277, (1987).

Shalev, G., et al., "Stimulation of homologous recombination in plants by expression of the bacterial resolvase RuvC", *PNAS USA, 96*, pp. 7398–7402, (Jun. 1999).

Singsit, C., et al., "Expression of a *Bacillus thuringiensis* crylA(c) gene in transgenic peanut plants and its efficacy against lesser cornstalk borer", *Transgenic Research, 6*, pp. 169–176, (1997).

Spencer, T.M., et al., "Segregation of Transgenes in Maize", *Plant Molecular Biology, 18*, pp. 201–210, (1992).

Stalker, D.M., et al., "Herbicide Resistance in Transgenic Plants Expressing a Bacterial Detoxification Gene", *Science, 242*, pp. 419–422, (Oct. 21, 1988).

Sternberg, N., et al., "Site–specific Recombination and Its Role in the Life Cycle of Bateriophage P1", *In: Cold Spring Harbor Symposia on Quantitative Biology, vol. XLV—Movable Genetic Elements*, Cold Spring Harbor Laboratory, New York, pp. 297–309, (1981).

Stougaard, J., "Substrate–Dependent Negative Selection in Plants Using a Bacterial Cytosine Deaminase Gene", *The Plant Journal, 3 (5)*, pp. 755–761, (1993).

Sutcliffe, J.G., "Nucleotide sequence of the ampicillin resistance gene of *Escherichia coli* plasmid pBR322", *PNAS USA, 75 (8)*, pp. 3737–3741, (Aug. 1978).

Swoboda, P., et al., "Intrachromosomal homologous recombination in whole plants", *The EMBO J., 13 (2)*, pp. 484–489, (1994).

Swoboda, P., et al., "Somatic homologous recombination in planta: The recombination frequency is dependent on the allelic state of recombining sequences and may be influenced by genomic position effects", *Mol. Gen. Genet., 237*, pp. 33–40, (1993).

Szostak, J.W., et al., "The Double–Stand–Break Repair Model for Recombination", *Cell, 33*, pp. 25–35, (May 1983).

Thillet, J., et al., "Site–directed Mutagenesis of Mouse Dihydrofolate Reductase", *The Journal of Biological Chemistry, 263 (25)*, pp. 12500–12508, (Sep. 1988).

Thompson, C.J., et al., "Characterization of the Herbicide–Resistance Gene bar from *Streptomyces hygroscopicus*", *EMBO Journal, 6 (9)*, pp. 2519–2523, (1987).

Tingay, S., et al., "*Agrobacterium tumefaciens*–mediated barley transformation", *The Plant Journal, 11 (6)*, pp. 1369–1376, (1997).

Tomes, D.T., et al., "Transgenic Tobacco Plants and Their Progeny Derived by Microprojectile Bombardment of Tobacco Leaves", *Plant Mol. Biol., 14*, pp. 261–268, (Feb. 1990).

Torbert, K.A., et al., "Transformation of Oat Using Mature Embryo–Derived Tissue Cultures", *Crop Science, 38 (1)*, pp. 226–231, (1998).

Torbert, K.A., et al., "Use of Paromomycin as a Selective Agent for Oat Transformation", *Plant Cell Reports, 14*, pp. 635–640, (1995).

Toriyama, K., et al., "Haploid and diploid plant regeneration from protoplasts of another callus in rice", *Theor. Appl. Genet., 73*, pp. 16–19, (1986).

Tovar, J., et al., "Somatic and Meiotic Chromosomal Recombination between Inverted Duplications in Transgenic Tobacco Plants", *The Plant Cell, 4*, pp. 319–332, (Mar. 1992).

Tsukada, M., et al., "Introduction of Foreign Genes into Tomato Protoplasts by Electroporation", *Plant Cell Physiol., 30 (4)*, pp. 599–603, (1989).

Uchimiya, H., et al., "Expression of a foreign gene in callus derived from DNA–treated protoplasts of rice (*Oryza sativa* L.)", *Mol. Gen. Genet., 204*, pp. 204–207, (1986).

Van Eck, J.M., et al., "Stable transformation of tomato cell cultures after bombardment with plasmid and YAC DNA", *Plant Cell Reports, 14*, pp. 299–304, (1995).

Vasil, V., et al., "Increased Gene Expression by the First Intron of Maize Shrunken–1 Locus in Grass Species", *Plant Physiol., 91*, pp. 1575–1579, (1989).

Yamada, Y., et al., "Plant regeneration from protoplast–derived callus of rice (*Oryza sativa* L.)", *Plant Cell Reports, 5*, pp. 85–88, (1986).

Zhang, J., et al., "Agrobacterium–Mediated Transformation of Elite Indica and Japonica Rice Cultivars", *Molecular Biotechnology, 8*, pp. 223–231, (1997).

Zheng, Y., et al., "Expression of resistance to barley stripe mosaic virus in barley and oat protoplasts", *Journal of General Virology, 71*, pp. 1865–1868, (1990).

Zhou, H., et al., "Stably transformed callus of wheat by electroporation–induced direct gene transfer", *Plant Cell Reports, 12*, pp. 612–616, (1993).

Zubko, E., et al., "Intrachromosomal recombination between attP regions as a tool to remove selectable marker genes from tobacco transgenes", *Nature Biotechnology, 18*, pp. 442–445, (Apr. 2000).

Zukowski, M.M., et al., "Chromogenic identification of genetic regulatory signals in *Bacillus subtilis* based on expression of a cloned Pseudomonas gene", *PNAS USA, 80*, pp. 1101–1105, (Feb. 1983).

* cited by examiner

Figure 1. Three pathways for obtaining "deletion derivatives"
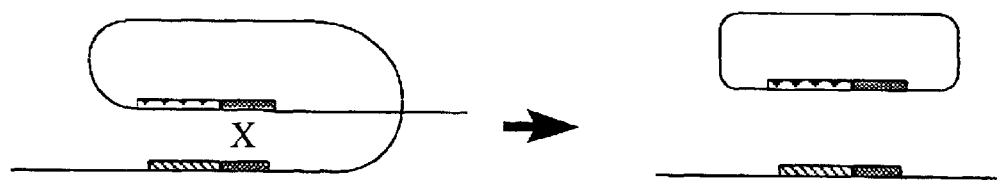
A. Loop-out
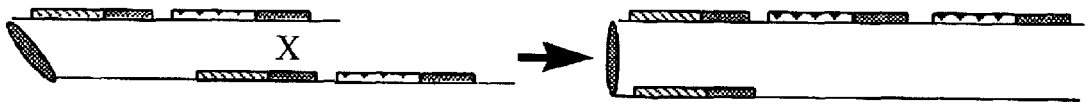
B. Unequal sister chromatid crossover
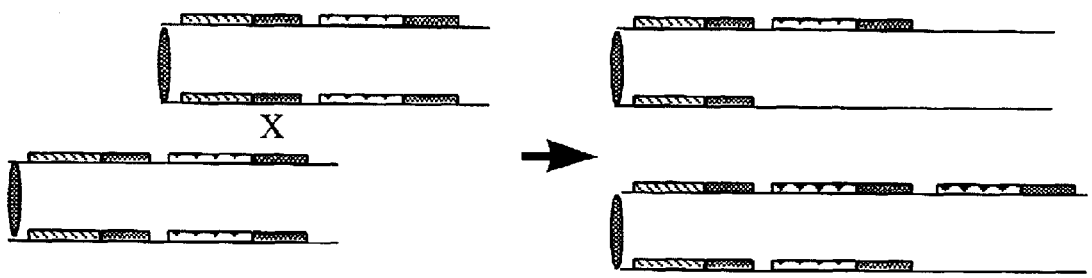
C. Unequal interhomologue crossover

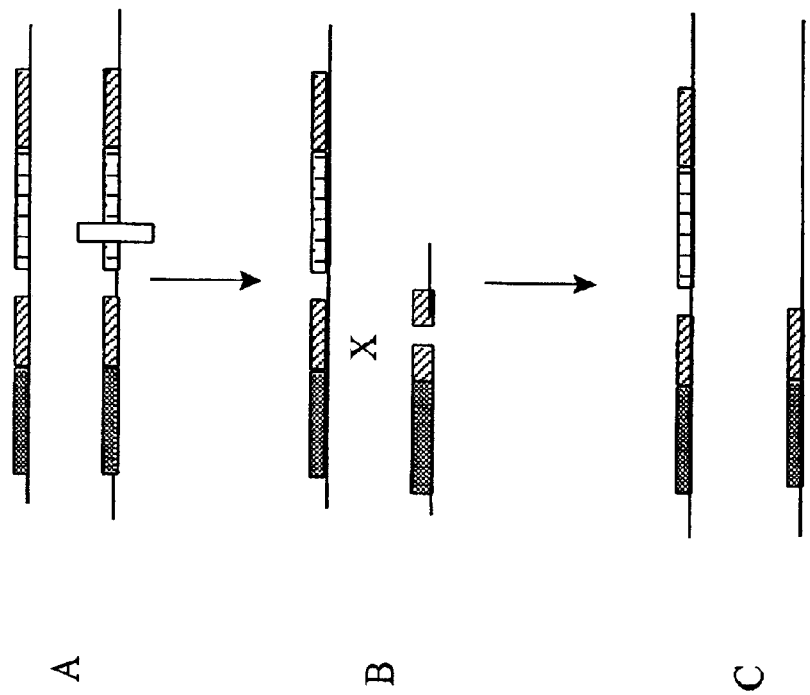
Figure 2. Gene conversion pathway (nonreciprocal recombination) for obtaining "deletion derivatives"

Figure 3. Single strand annealing model
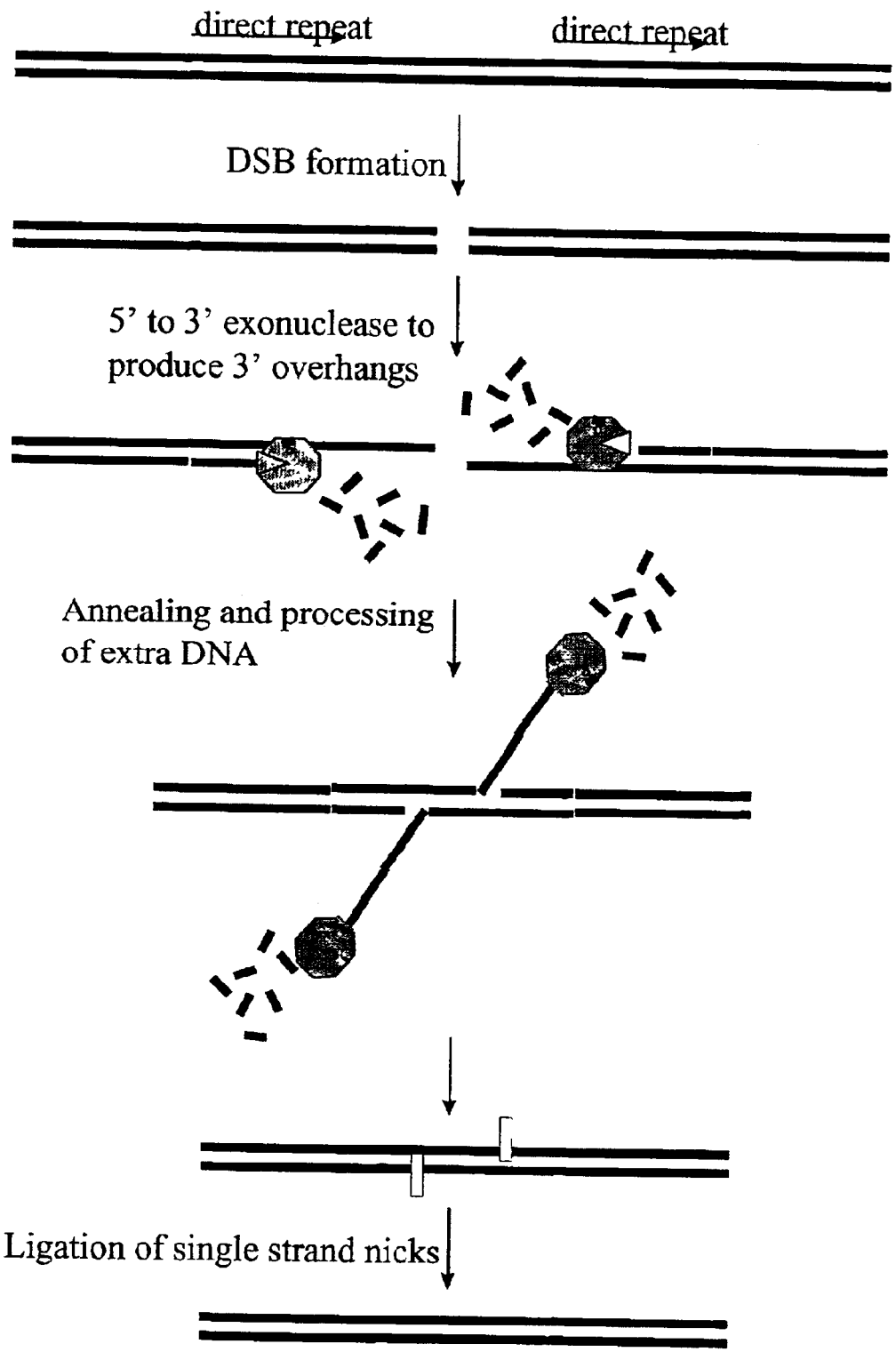

Direct Repeat Induced, Non-Reciprocal Recombination-Mediated Transgene Deletion

I. Hemizygous R₁ Transgenic Plant

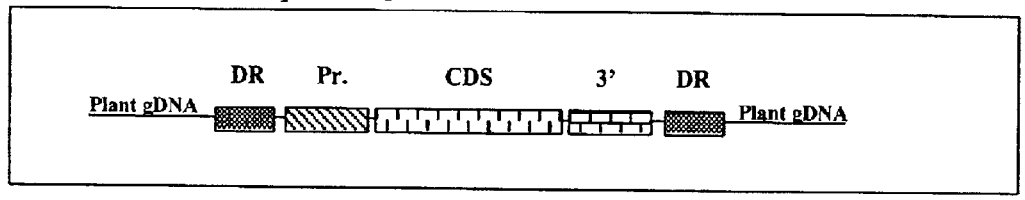

II. Homozygous S₁ Transgenic Plant at Meiosis

A. Reciprocal Recombination

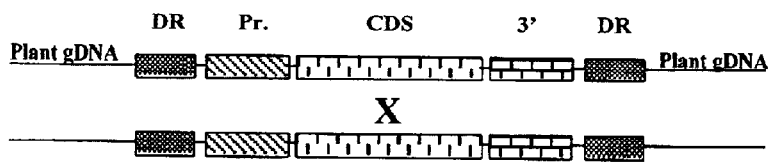

B. Non-Reciprocal Recombination

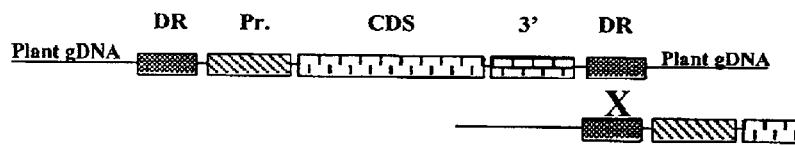

III. F₁ Recombinant Progeny Plants

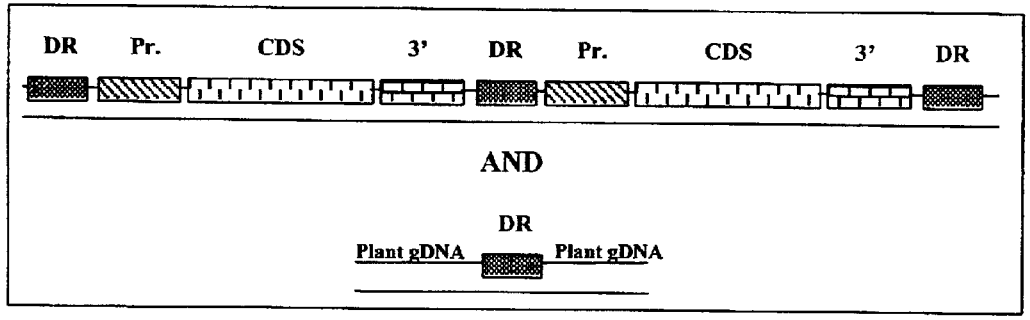

In the graphic illustration:

| | | |
|---|---|---|
| Plant gDNA | = | plant genomic DNA flanking the site of transgene integration |
| DR | = | Direct Repeat |
| Pr. | = | "Promoter" |
| CDS | = | coding sequence |
| 3' | = | transcription terminator |

Figure 5.

DBT418 Altered Transgene Insertions
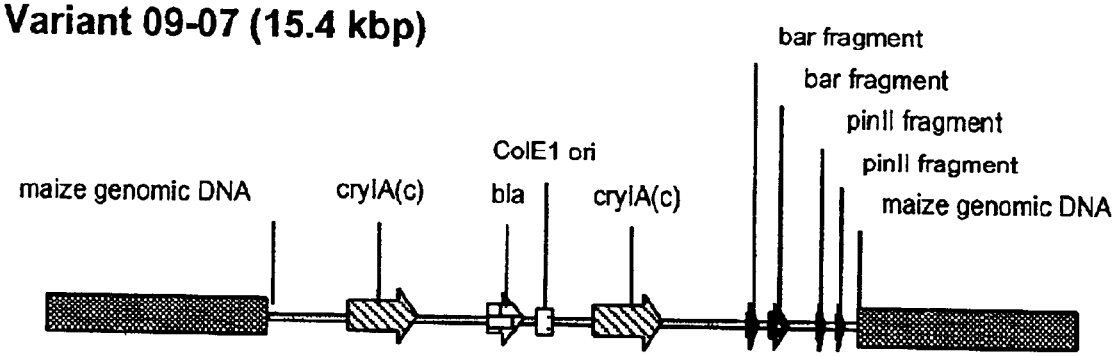
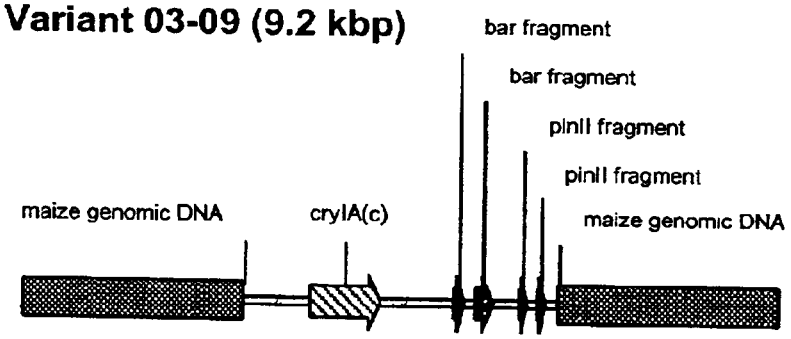
Figure 10.

Non-Reciprocal Recombination-Mediated Transgene Deletion in MON849
I. Hemizygous BC$_n$ Transgenic Plant
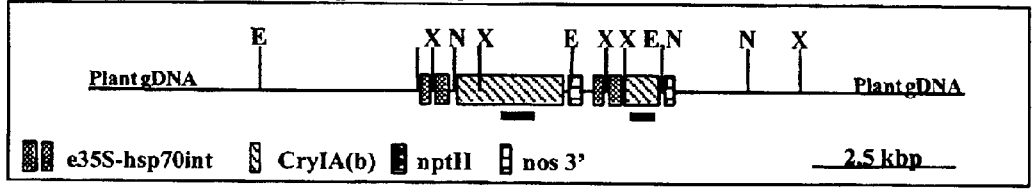
II. Homozygous S$_1$ Transgenic Plant at Meiosis
A. Reciprocal Recombination
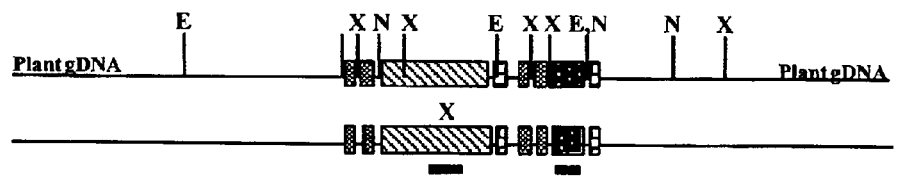
B. Non-Reciprocal Recombination
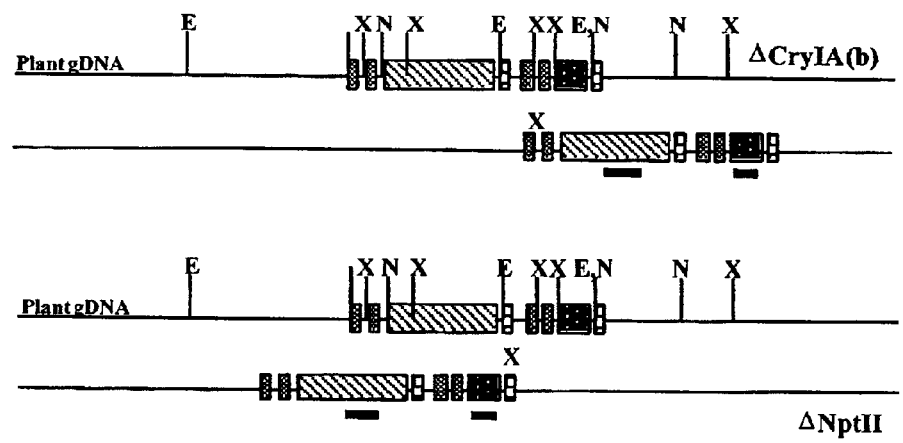
Figure 11.

HOMOLOGOUS RECOMBINATION-MEDIATED TRANSGENE ALTERATIONS IN PLANTS

This application is a continuation-in-part of application Ser. No. 09/521,557 filed Mar. 9, 2000 now U.S. Pat. No. 6,580,019.

BACKGROUND OF THE INVENTION

1. Field of the Invention

The present invention relates to methods for producing transgenic cells, preferably plant cells, and transgenic plants in which the transgene insertion has been altered by homologous recombination. Alterations include deletions, modifications, or duplications of transgene sequences. The invention further relates to a method for deleting ancillary sequences, such as selectable marker or reporter genes, from transgenic cells, preferably plant cells, and transgenic plants.

2. Description of the Related Art

Genetically modified (GM) crops offer many advantages to the farmer in terms of inputs to crop production, e.g. weed and insect control, and improved usage of water and nutrient inputs. GM plants also provide a means for improving nutritional value, e.g. improved amino acid or protein composition, improved starch and oil quantities and qualities, increased vitamin levels, or bioavailability of nutrients, or can be the source of pharmaceuticals or "nutraceuticals." Methods have been developed for conferring tolerance or resistance to water or salt stress in monocots (U.S. Pat. No. 5,780,709), for example, and a single gene has been used to improve tolerance to drought, salt loading, and freezing in some plants (Kasuga et al., 1999). Insect resistance can be conferred by introducing genes for the production of toxins found in the soil bacterium *Bacillus thuringiensis* (Bt). Lysine content has been increased by incorporating the genes for bacterial enzymes (e.g. Corynebacterium dihydropicolinic acid synthase and *E. coli* aspartokinase) into GM plants. The comparable plant enzymes are subject to lysine feedback inhibition, while the bacterial enzymes show little or no feedback inhibition.

Until technology made genetic modification of plants possible, production of plants with desirable characteristics was dependent upon selective breeding and the variability naturally present in a crop and closely related sexually compatible species. Genetic modification through transformation provides an efficient and controlled method for producing plants with one or more desired characteristics, including characteristics that are normally not found in those crops, such as resistance to herbicides or pests, or nutritionally balanced food or feed products.

Genetic modification of crops by transformation sometimes involves transfer of one or more desired genes, along with ancillary sequences such as antibiotic resistance markers or reporter genes, into a plant cell. Antibiotic resistance markers used in plant genetic engineering, for example, include the kanamycin resistance marker (Carrer et al., 1993), streptomycin resistance marker (Moll et al., 1990), lincomycin resistance marker (Jenkins et al., 1991) and the neomycin resistance marker (Beck et al., 1982). The ancillary sequences are necessary for identification or selection of transformed cells, but do not contribute to the trait conferred on the plant. Since ancillary sequences do not contribute to the desired crop improvement, efforts have been made to delete them from the GM progeny. Antibiotic resistance markers have particularly been targeted for deletion.

Furthermore, it has been demonstrated that using direct DNA delivery methods, such as microprojectile bombardment, complex transgene insertions may occur including duplications, deletions, and complex rearrangements of introduced DNA (PCT Publication No. WO 99/32642). Complex transgene insertions may contribute to co-suppression of gene expression or genetic instability of the insertion. Use of the present invention contributes to reducing the complexity of transgene insertions, thereby stabilizing gene expression and preferably removing ancillary sequences.

A number of site-specific recombination-mediated methods have been developed for incorporating target genes into plant genomes, as well as for deleting unwanted genetic elements from plant and animal cells. For example, the cre-lox recombination system of bacteriophage P1, described by Abremski et al. (1983), Sternberg et al. (1981) and others, has been used to promote recombination in a variety of cell types. The cre-lox system utilizes the cre recombinase isolated from bacteriophage P1 in conjunction with the DNA sequences (termed lox sites) it recognizes. This recombination system has been effective for achieving recombination in plant cells (U.S. Pat. No. 5,658,772), animal cells (U.S. Pat. No. 4,959,317 and U.S. Pat. No. 5,801,030), and in viral vectors (Hardy et al., 1997).

Wahl et al. (U.S. Pat. No. 5,654,182) used the site-specific FLP recombinase system of *Saccharomyces cerevisiae* to delete DNA sequences in eukaryotic cells. The deletions were designed to accomplish either inactivation of a gene or activation of a gene by bringing desired DNA fragments into association with one another. Activity of the FLP recombinase in plants has been demonstrated (Lyznik et al, 1996; Luo et al., 2000).

Others have used transposons, or mobile genetic elements that transpose when a transposase gene is present in the same genome, to separate target genes from ancillary sequences. Yoder et al. (U.S. Pat. No. 5,482,852 and U.S. Pat. No. 5,792,924) used constructs containing the sequence of the transposase enzyme and the transposase recognition sequences to provide a method for genetically altering plants that contain a desired gene free of vector and/or marker sequences.

Oliver et al. (U.S. Pat. No. 5,723,765) used site-specific recombination systems in conjunction with a blocking sequence to provide a regulatory mechanism in transgenic plants. In this method, when site-specific recombination results in excision of the blocking sequence, regulatory elements that either induce or repress a particular gene of interest are moved into an appropriate position upstream from the target sequence.

Although each of these methods has been designed specifically to excise unwanted sequences, each also relies upon introduction of ancillary genetic sequences (e.g., recombinase or transposase specific recognition sequences) that ultimately do not contribute to the desired crop improvement.

Thus, there is a need for a method for excising unwanted DNA sequences from transgenic cells without introducing any further ancillary DNA sequences.

The present invention is exemplified herein by alterations of transgenic insertions in plant cells and transgenic plants. It is, however, the belief of the inventors that the methods of the present invention are equally applicable to, and useful in, any organism in which homologous recombinatin of DNA occurs.

SUMMARY OF THE INVENTION

The invention provides a novel method for excision, modification, or amplification of DNA sequences from transgenic cells that does not involve the use of site-specific recombination enzymes, including transposase enzymes, but instead relies upon directly repeated DNA sequences positioned about the target sequence to direct excision or amplification through native cellular recombination mechanisms. The invention provides a method of preparing a recombined transgenic cell having a preselected DNA sequence flanked by directly repeated DNA sequences. Additionally, the transgene insertion may comprise further DNA sequences. In the method of the present invention, the direct repeat may be recognized by a site-specific recombinase enzyme, but a site-specific recombinase is not required for deletion of the desired sequence.

The invention provides a method of preparing a transgenic cell having an altered transgene insertion. A first transgenic cell is obtained, wherein the transgenic insertion DNA sequence comprises a pre-selected DNA sequence flanked by directly repeated DNA sequences. A plurality of progeny cells of any generation are obtained and a second cell is identified from a the progeny cells, wherein the second cell contains a DNA insertion sequence that has been altered by recombination. The first cell can be either homozygous or hemizygous for the second DNA sequence.

The invention further provides methods of using a negative selectable marker gene to identify cells with altered transgene insertions.

The invention provides a novel method of removing undesirable DNA sequences as well as a method for resolving complex transgene insertions to simpler insertions, thereby increasing transgene stability and decreasing the occurrence of co-suppression.

The invention provides a method of preparing a fertile transgenic plant having an altered transgene insertion comprising obtaining a first fertile transgenic plant comprising a transgene insertion DNA sequence, wherein the transgene insertion DNA sequence comprises a pre-selected DNA sequence flanked by directly repeated DNA sequences, obtaining a plurality of progeny of any generation of the first transgenic plant, and selecting a progeny fertile transgenic plant wherein the transgene insertion is altered as compared to the first fertile transgenic plant. Methods are provided wherein the pre-selected DNA sequence comprises a selectable marker gene or a reporter gene, such as a bar, nptII or a gene encoding a glyphosate resistant EPSPS enzyme. Furthermore, methods are provided wherein the plurality of progeny plants are obtained by either self-pollination or outcrossing. The resultant progeny plants may be either inbreds or hybrids. The plants may be monocot plants, such as a maize, sorghum, barley, wheat rye or rice or dicot plants such as soybean, canola, sunflower, or cotton.

The invention provides a method of preparing a recombined fertile transgenic plant, by obtaining a first fertile transgenic plant having a preselected DNA sequence flanked by directly repeated DNA sequences. Additionally, the transgene insertion may comprise further DNA sequences. In the method of the present invention, the direct repeat may be recognized by a site-specific recombinase enzyme, but a site-specific recombinase is not required for deletion of the desired sequence. The first fertile transgenic plants are crossed to produce either hybrid or inbred progeny plants, and from those progeny plants one or more second fertile transgenic plants are selected that contain a second DNA sequence that has been altered by recombination. The first fertile transgenic plant can be either homozygous or hemizygous for the second DNA sequence.

Also provided by the present invention is a transgenic cell or plant produced by the method, wherein the transgene insertion is altered as compared to the first fertile transgenic cell or plant.

The invention also provides a seed for producing a recombinant transgenic plant, wherein the transgene insertion is altered as compared to a first fertile transgenic plant.

Also provided is a fertile transgenic plant wherein a transgene insertion is altered from a parent transgene insertion. The plant may be hybrid or inbred. The transgene insertion may be altered in that it has been deleted, amplified, or rearranged.

Further provided is a progeny cell or plant of any generation comprising an altered transgene insertion, wherein the transgene insertion is altered from the transgene insertion in a parental $R_0$ plant.

The present invention also provides an altered transgene insertion DNA sequence preparable by the method comprising obtaining a first fertile transgenic plant comprising a transgene insertion DNA sequence, wherein the transgene DNA sequence comprises a pre-selected DNA sequence flanked by directly repeated DNA sequences; obtaining a plurality of progeny of any generation of the first transgenic plant; and selecting a progeny fertile transgenic plant wherein the transgene insertion is altered as compared to the first fertile transgenic plant. The transgene insertion may be altered in that it has been deleted, amplified, or rearranged. Alteration of the transgene insertion may result in a change in expression of a transgene contained within the parental transgene insertion. The alteration of the transgene may be identified by DNA analysis, such as by PCR or Southern blot analysis. The altered transgene insertion may be in a monocot plant, such as a maize, sorghum, barley, wheat, rye or rice plant or a dicot plant such as cotton, soybean, sunflower or canola.

BRIEF DESCRIPTION OF THE DRAWINGS

FIG. 1. Pathways for obtaining deletion derivatives

FIG. 2. Gene conversion pathway (non-reciprocal recombination) for obtaining deletion derivatives.

FIG. 3. Single strand annealing model.

FIG. 5. Direct repeat induced homologous recombination-mediated alteration of a transgene insertion.

FIG. 10. Altered transgene insertions recovered following homologous recombination in DBT418.

FIG. 11. MON849 transgene insertion and altered insertions recovered following homologous recombination.

DETAILED DESCRIPTION OF THE INVENTION

Figure 4:
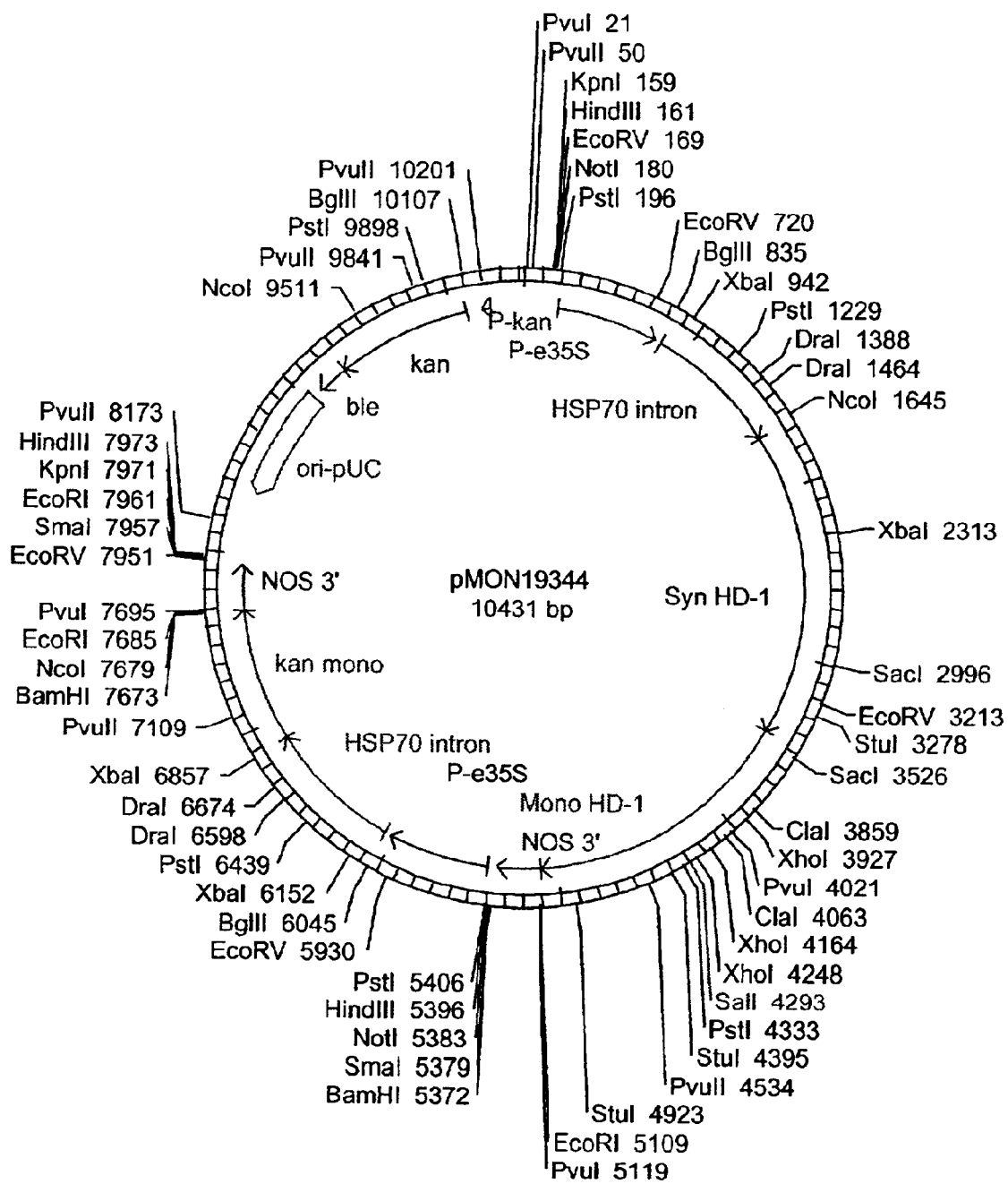
FIG. 4. Plasmid vector pMON19344

The invention provides a novel method for production of transgenic cells and plants lacking ancillary DNA sequences that do not contribute to the desired phenotypic trait. The inventors have discovered that homologous recombination occurs in the plant cells at a rate sufficient to provide recombined transgenic progeny without added recombinase enzymes. In the method provided, directly repeated DNA sequences are located 5' and 3' to a target sequence, to be amplified within, modified, or excised from the plant genome. The inventors have determined that gene deletion frequency, for example, is approximately 0.1% per 287±19 base pairs of homologous direct repeat sequence. The method described herein can be used to delete selectable marker genes, to delete partial or rearranged gene copies, to reduce overall transgene copy number, or to increase overall transgene copy number.

In direct repeat-mediated homologous recombination, which can be used particularly to produce transgene deletions, direct repeats that are present in the introduced DNA sequence, or produce a DNA alignment, result in amplification of the number of copies of a particular gene sequence or excision of either one or more ancillary DNA sequences or target DNA sequences. This method can be used to delete ancillary sequences or to remove regulatory sequences, for example, in order to activate or deactivate a target gene.

It is known that homologous recombination results in genetic rearrangements of transgenes in plants. Repeated DNA sequences have been shown to lead to deletion of a flanked sequence in various dicot species, e.g. *Arabidopsis thaliana* (Swoboda et al., 1994); Jelesko et al., 1999), *Brassica napus* (Gal et al., 1991; Swoboda et al, 1993) and *Nicotiana tabacum* (Peterhans et al., 1990; Zubko et al., 2000). In most instances alteration of transgene sequences was attributed to recombination in somatic cells and occurred at low frequencies generally ranging from $10^{-6}$ to $10^{-7}$. Meiotic recombination of a native plant sequence transgene was observed in Arabidopsis at a frequency of $3 \times 10^{-6}$ and in tobacco at a frequency of $3 \times 10^{-5}$ to $1 \times 10^{-6}$ (Tovar and Lichtenstein, 1992). In tobacco the more frequent recombinants were recovered from homozygous parents (Tovar and Lichtenstein, 1992), but only at a frequency of about $3 \times 10^{-5}$. While it is possible to screen millions of seeds to identify alterations of transgene sequences in species such as *Arabidopsis thaliana* or *Nicotiana tabacum*, in agronomic crops such as corn screening of millions of plants for loss of expression of a transgene would be difficult. For example, a field screen of 1,000,000 corn plants would require about 40 acres of plants to be screened to identify a single recombinant at a frequency of $10^{-6}$. In the method of the present invention, homologous recombination of transgenes was observed at frequencies greater than 0.1% and, therefore, a screen of recombinants could be conducted on as few as 1000 plants requiring only about 0.04 acres in the field.

One of the most widely held models for homologous recombination is the double-strand break repair (DSBR) model (Szostak et al, 1983). In the context of the DSBR model, there are three reciprocal recombination pathways for generating a deletion by recombination between direct repeats. These are shown in FIG. 1. Directly repeated DNA is represented by the small dotted rectangles in FIG. 1. In the first pathway (FIG. 1A), commonly referred to as a "loop out", the chromatid loops back on itself and a reciprocal exchange in the region of the homology results in excision of a circle bearing one of the two repeats. Loop outs have been widely observed in a variety of systems, and can occur between repeats that are very closely linked, i.e. less than 1 Kb apart. Thus, there is no steric hindrance to loop outs between most transgene repeats. The next two pathways, unequal sister chromatid crossover (FIG. 1B) and unequal inter-homologue crossover (FIG. 1C) are identical except that in the former recombination occurs between sister chromatids and in the latter it occurs between chromosomes pairs. In both cases the reciprocality results in a deletion on one chromatid and an increase in copy number on the other. In the case of unequal inter-homologue crossovers (FIG. 1C), flanking alleles will be recombined. All pathways are examples of reciprocal recombination. Even in the example of the loop outs, it is clear that this process is reciprocal, although one of the two products (the excised circle) will be lost in subsequent cell divisions.

The DSBR model can give rise to reciprocal recombination events such as those shown above, as well as nonreciprocal recombination events known as gene conversions. Gene conversion can occur frequently between transgene repeats. Evidence for gene conversion between inverted repeats in plants was obtained by Tovar and Lichtenstein (1992). Deletion by reciprocal recombination was not possible in this system (since the repeats were inverted, not direct), but it may be possible to obtain a deletion by a gene conversion pathway. An example of this is shown in FIG. 2. For convenience the example uses the context of the DSBR model, although other models may apply. If a double strand break occurs in or between two repeated elements on one chromatid (FIG. 2A), the DSB can be expanded into a gap reaching the sequences of the two direct repeats (FIG. 2B), deleting the intervening sequence. The gap can then be repaired using one of the two repeats on another chromatid as a template. The repair product will have deleted one of the repeats on the chromatid on which the DSB initiated (FIG. 2C), without a concomitant increase in copy number on the other chromatid, i.e. the event was nonreciprocal.

Both types of recombination described above, reciprocal and nonreciprocal, are conservative recombination pathways, i.e. there is no physical loss of DNA sequence in the final products relative to the parental molecules. Genetic information may have changed, but the chromosomes still have the same general physical structure. Evidence for a nonconservative pathway exists. Experiments in yeast have led to the proposal of a model to account for nonconservative recombination between closely linked direct repeats. This model, called the single-strand annealing (SSA) model, is shown in FIG. 3.

In the SSA model, recombination between closely linked direct repeats initiates with a DSB between the two regions of homology (as shown in FIG. 3) or within one of the two repeats. As in the DSBR model, the ends are processed by an exonuclease to generate long single-stranded tails. As the tails extend into the regions of homology complementary DNA is revealed, allowing the two tails to anneal to each other. Any sequences that were between the two repeats would be left as single stranded tails and would be removed, perhaps by a second nuclease. After ligation of nicks the final product has deleted the DNA between the two repeats in a nonconservative manner, i.e. the intervening DNA is lost in the process. As with the DSBR repair model, significant experimental evidence, primarily from yeast, exists to support the SSA model.

There are important distinctions between the DSBR model and the SSA model. First, the SSA model will work only with direct repeats of homology, whereas the DSBR model will work with either inverted or direct repeats, although only in the latter will a deletion occur. Second, the DSBR mechanism can occur within a chromatid (i.e. shown below in FIG. 1A) or between two chromatids (i.e. shown below in FIGS. 1B and 1C). With the SSA mechanism, recombination is likely to involve only one chromatid. In order for recombination to take place between two chromatids both chromatids would have to sustain a DSB in approximately the same position at approximately the same time In summary, there are at least five pathways by which deletions can be formed by homologous recombination between direct repeats. Three pathways involve reciprocal recombination (FIG. 1), one pathway involves nonreciprocal recombination (gene conversion, FIG. 2), and one pathway is nonconservative, the SSA model (FIG. 3). Table 1 summarizes these pathways and their characteristics.

TABLE 1

Pathways for obtaining deletion derivatives in plants

| Pathway | effect of zygosity | other distinguishing properties |
|---|---|---|
| loop out | deletion can occur in hemi- or homozygotes | extrachromosomal circle is produced, no increase in copy number |
| unequal sister chromatid exchange | deletion can occur in hemi- or homozygotes | increase in copy number on sister chromatid |
| unequal inter-homologue exchange | homozygosity is required for deletions to occur | increase in copy number on homologue, flanking markers recombined, may be elevated in meiosis |
| gene conversion | deletion can occur in hemi- or homozygotes | no increase in copy number, flanking markers are not recombined, may be elevated in meiosis in homozygotes |
| single strand annealing | deletion can occur in hemi- or homozygotes | may be distance dependent, i.e. closer repeats recombine more |

By producing a transgene construct that incorporates DNA sequence homologies at desired locations, it is possible to enhance the frequency of such homologous recombination events in transgenic plant cells, resulting in targeted deletion or amplification of desired DNA sequences in progeny cells.

The method of the present invention can be used with a variety of plants, and is especially useful for development of transgenic monocot plants, such as maize, sorghum, barley, wheat, rye or rice and dicot plants such as soybean, cotton, canola and potato.

II. Definitions

The following words and phrases have the meanings set forth below.

Chimeric gene: A gene or DNA sequence or segment comprising at least two DNA sequences or segments from species that do not combine DNA under natural conditions, or DNA sequences or segments that are positioned or linked in a manner that does not normally occur in the native genome of an untransformed plant, such as maize or another monocot.

Exogenous gene: A gene that is not normally present in a given host genome in the present form. In this respect, the gene itself may be native to the host genome, however the exogenous gene will comprise the native gene altered by the addition or deletion of one or more different regulatory elements.

Expression: An intracellular process undergone by a coding DNA molecule, such as a structural gene, to produce at least an RNA molecule. Usually a polypeptide is produced through the combined processes of transcription and translation.

Expression cassette: A nucleic acid segment comprising at least a first gene that one desires to have expressed in a host cell and the necessary regulatory elements for expressing the gene in the host cell. Preferred regulatory elements for use with the invention include promoters, enhancers and terminators. It also may be desirable to include on the expression cassette a nucleic acid segment encoding an appropriate transit peptide, as is described below. The expression cassette may be contained and propagated in any suitable cloning vector, for example, a plasmid, cosmid, bacterial artificial chromosome, or yeast artificial chromosome. The whole vector DNA may be used to transform a host cell, or alternatively, the expression cassette may be isolated from the vector and then used for transformation.

Expression vector: A vector comprising at least one expression cassette.

Heterologous DNA: DNA from a source different from that of the recipient cell.

Homologous DNA: DNA from the same source as that of the recipient cell.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant.

Progeny: Any subsequent generation, including the seeds and plants therefrom, which is derived from a particular parental plant or set of parental plants.

Promoter: A recognition site on a DNA sequence or group of DNA sequences that provide an expression control element for a structural gene and to which RNA polymerase specifically binds and initiates RNA synthesis (transcription) of that gene.

$R_0$ Transgenic Plant: A plant that has been directly transformed with selected DNA or has been regenerated from a cell or cell cluster that has been transformed with a selected DNA.

Recombined transgenic: A transgenic plant cell, plant part, plant tissue or plant, the transgenic DNA sequences or genes of which are altered by non-reciprocal homologous recombination. Altered includes deleted, amplified, or any other modification of the preselected DNA sequence as originally integrated into the host genome.

Regeneration: The process of growing a plant from a plant cell (e.g., plant protoplast, callus or explant).

Selected DNA: A DNA segment that one desires to introduce into a plant genome by genetic transformation.

Selected gene: A gene that one desires to have expressed in a transformed plant, plant cell or plant part. A selected gene may be native or foreign to a host genome, but where the selected gene is native to the host genome, will include one or more regulatory or functional elements that differ from native copies of the gene.

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformation construct: A chimeric DNA molecule that is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell wherein its DNA has been altered by the introduction of an exogenous DNA molecule into that cell.

Transgene: A segment of DNA that has been incorporated into a host genome or is capable of autonomous replication in a host cell and is capable of causing the expression of one or more cellular products. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation that was transformed with the DNA segment.

Transgene insertion: A segment of DNA incorporated into a host genome. A transgene insertion comprises all of the DNA sequences that were introduced by transformation and are present at a single genetic locus in a transformed cell or plant. DNA sequences within the transgene insertion may arise from one or more plasmid vectors. Furthermore, DNA sequences may be rearranged in a transgene insertion when compared to the arrangement of DNA sequences in the parent plasmid vector or vectors. A transgene insertion may be altered using the methods of this invention, resulting in deletion, duplication, or rearrangement of DNA sequences. A parent transgene insertion is the original transgene insertion in a parent plant. The parent transgene insertion may be altered by non-reciprocal recombination during a cycle of meiosis and then transmitted to the progeny as an altered transgene insertion.

Transgenic cell: Any cell derived or regenerated from a transformed cell or derived from a transgenic cell. Exemplary transgenic cells include plant calli derived from a transformed plant cell and particular somatic cells such as leaf, root, stem, or reproductive (germ) cells obtained from a transgenic plant.

Transit peptide: A polypeptide sequence that is capable of directing a polypeptide to a particular organelle or other location within a cell.

Vector: A DNA molecule capable of replication in a host cell and/or to which another DNA segment can be operatively linked so as to bring about replication of the attached segment. A plasmid is an exemplary vector.

Wild type: An untransformed plant cell, plant part, plant tissue or plant wherein the genome has not been altered by the presence of a preselected DNA sequence.

II. DNA Constructs of the Invention

Virtually any DNA may be used for delivery to recipient cells to ultimately produce fertile transgenic plants in accordance with the present invention. For example, an isolated and purified DNA segment in the form of vectors and plasmids encoding a desired gene product or linear DNA fragments, in some instances containing only the DNA element to be expressed in the plant, and the like, may be employed.

DNA useful for introduction into plant cells includes that which has been derived or isolated from any source, that may be subsequently characterized as to structure, size and/or function, chemically altered, and later introduced into a plant. An example of DNA "derived" from a source, would be a DNA sequence or segment that is identified as a useful fragment within a given organism, and is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering. Such DNA is commonly referred to as "recombinant DNA."

Therefore, useful DNA includes completely synthetic DNA, semi-synthetic DNA, DNA isolated from biological sources, and DNA derived from RNA. It is within the scope of the invention to isolate and purify a DNA segment from a given genotype, and to subsequently introduce multiple copies of the isolated and purified DNA segment into the same genotype, e.g., to enhance production of a given gene product.

The introduced DNA includes, but is not limited to, DNA from plant genes and non-plant genes, such as those from bacteria, yeasts, animals or viruses. The introduced DNA can include modified genes, portions of genes, or chimeric genes, including genes from the same or different genotype.

An isolated and purified DNA segment, molecule or sequence can be identified and isolated by standard methods, as described by Sambrook et al. (1989). The isolated and purified DNA segment can be identified by screening of a DNA or cDNA library generated from nucleic acid derived from a particular cell type, cell line, primary cells, or tissue. Screening for DNA fragments that encode all or a portion of the isolated and purified DNA segment can be accomplished by screening plaques from a genomic or cDNA library for hybridization to a probe of the DNA from other organisms or by screening plaques from a cDNA expression library for binding to antibodies that specifically recognize the protein encoded by the isolated and purified DNA segment. DNA fragments that hybridize to an isolated and purified DNA segment probe from other organisms and/or plaques carrying DNA fragments that are immunoreactive with antibodies to the protein encoded by the isolated and purified DNA segment can be subcloned into a vector and sequenced and/or used as probes to identify other cDNA or genomic sequences encoding all or a portion of the isolated and purified DNA segment.

Portions of the genomic copy or copies of the isolated and purified DNA segment can be sequenced and the 5' end of the DNA identified by standard methods including either DNA sequence homology to other homologous genes or by RNAase protection analysis, as described by Sambrook et al. (1989). Once portions of the 5' end of the isolated and purified DNA segment are identified, complete copies of the isolated and purified DNA segment can be obtained by standard methods, including cloning or polymerase chain reaction (PCR) synthesis using oligonucleotide primers complementary to the isolated and purified DNA segment at the 5' end of the DNA. The presence of an isolated full-length copy of the isolated and purified DNA can be verified by hybridization, partial sequence analysis, or by expression of the isolated and purified DNA segment.

The DNA may be circular or linear, double-stranded or single-stranded. Generally, the DNA is in the form of chimeric DNA that can also contain coding regions flanked by regulatory sequences that promote the expression of the recombinant DNA present in the resultant plant (an "expression cassette"). For example, the DNA may itself comprise or consist of a promoter that is active in which is derived from a non-source, or may utilize a promoter already present in the genotype.

Ultimately, the most desirable DNA segments for introduction into a monocot genome may be homologous genes or gene families that encode a desired trait (e.g., increased yield per acre) and that are introduced under the control of novel promoters or enhancers, etc., or perhaps even homologous or tissue-specific (e.g., root-, collar/sheath-, whorl-, stalk-, ear shank-, kernel- or leaf-specific) promoters or control elements. Indeed, it is envisioned that a particular use of the present invention may be the targeting of an isolated and purified DNA segment in a tissue- or organelle-specific manner.

The construction of vectors that may be employed in conjunction with the present invention will be known to those of skill in the art in light of the present disclosure (see, e.g., Sambrook et al., 1989; Gelvin et al., 1990).

Generally, the introduced DNA will be relatively small, i.e., less than about 30 kb to minimize any susceptibility to physical, chemical, or enzymatic degradation that is known to increase as the size of the DNA increases. The number of proteins, RNA transcripts or mixtures thereof that is introduced into the genome is preferably isolated and purified and defined, e.g., from one to about 5–10 such products of the introduced DNA may be formed.

A. Expression Cassettes

1. Promoters, Enhancers and Other Non-3¢ Transcription Regulatory Sequences

Preferably, the expression cassette of the invention is operably linked to a promoter, which provides for expression of a linked DNA sequence. The DNA sequence is operably linked to the promoter when it is located downstream from the promoter, to form an expression cassette. An isolated promoter sequence that is a strong promoter for heterologous DNAs is advantageous because it provides for a sufficient level of gene expression to allow for easy detection and selection of transformed cells and provides for a high level of gene expression when desired.

Most endogenous genes have regions of DNA that are known as promoters, which regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. Promoters can also provide for tissue specific or developmental regulation.

Preferred expression cassettes will generally include, but are not limited to, a plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang et al., 1990), α-tubulin, ubiquitin, actin (Wang et al., 1992), cab (Sullivan et al., 1989), PEPCase (Hudspeth et al., 1989) or those associated with the R gene complex (Chandler et al., 1989). Further suitable promoters include inducible promoters, such as the light inducible promoter derived from the pea rbcS gene (Coruzzi et al., 1971), the actin promoter from rice (McElroy et al., 1990), and water-stress-, ABA-and turgor-inducible promoters (Skriver et al., 1990; Guerrero et al., 1990), tissue-specific promoters, such as root-cell promoters (Conkling et al., 1990), and developmentally-specific promoters such as seed specific promoters, e.g., the phaseolin promoter from beans (Sengupta-Gopalan, 1985), and the Z10 and Z27 promoters from maize. For example, expression of zein storage proteins is initiated in the endosperm about 15 days after pollination. Tissue specific expression may also be functionally accomplished by introducing a constitutively expressed gene (all tissues) in combination with an antisense gene that is expressed only in those tissues where the gene product is not desired.

Promoters that direct specific or enhanced expression in certain plant tissues will be known to those of skill in the art in light of the present disclosure. These include, for example, the rbcS promoter, specific for green tissue; the ocs, nos and mas promoters that have higher activity in roots or wounded leaf tissue; a truncated (−90 to +8) 35S promoter that directs enhanced expression in roots, an α-tubulin gene that directs expression in roots and promoters derived from zein storage protein genes that direct expression in endosperm. Transcription enhancers or duplications of enhancers can be used to increase expression from a particular promoter (see, for example, Fromm et al., 1989). Examples of such enhancers include, but are not limited to, elements from the CaMV 35S promoter and octopine synthase genes (U.S. Pat. No. 5,290,924). It is particularly contemplated that one may advantageously use the 16 bp ocs enhancer element from the octopine synthase (ocs) gene (Ellis et al., 1987; Bouchez et al., 1989), especially when present in multiple copies, to achieve enhanced expression in roots. Other promoters useful in the practice of the invention are known to those of skill in the art. For example, see Van Ooijen et al. (U.S. Pat. No. 5,593,963) and Walsh et al. (U.S. Pat. No. 5,743,477).

Alternatively, novel tissue-specific promoter sequences may be employed in the practice of the present invention. cDNA clones from a particular tissue are isolated and those clones that are expressed specifically in that tissue are identified, for example, using Northern blotting. Preferably, the gene isolated is not present in a high copy number, but is expressed in specific tissues. The promoter and control elements of corresponding genomic clones can then be localized using techniques well known to those of skill in the art.

As the DNA sequence inserted between the transcription initiation site and the start of the coding sequence, i.e., the untranslated leader sequence, can influence gene expression, one can also employ a particular leader sequence. Preferred leader sequence include those that comprise sequences selected to direct optimum expression of the attached gene, i.e., to include a preferred consensus leader sequence that can increase or maintain mRNA stability and prevent inappropriate initiation of translation (Joshi, 1987). Such sequences are known to those of skill in the art. Sequences that are derived from genes that are highly expressed in plants and in maize, in particular, will be most preferred.

Regulatory elements such as Adh intron 1 (Callis et al., 1987), sucrose synthase intron (Vasil et al., 1989), rice actin 1 intron 1 (McElroy et al., 1991) or TMV omega element (Gallie et al., 1989) can also be included where desired. Other such regulatory elements useful in the practice of the invention are known to those of skill in the art.

An isolated and purified DNA segment can be combined with the transcriptional regulatory sequences by standard methods as described in Sambrook et al., cited supra, to yield an expression cassette. Briefly, a plasmid containing a promoter such as the 35S CaMV promoter can be constructed as described in Jefferson (1987) or obtained from Clontech Lab in Palo Alto, Calif. (e.g., pBI121 or pBI221). Typically, these plasmids are constructed to provide for multiple cloning sites having specificity for different restriction enzymes downstream from the promoter. The isolated and purified DNA segment can be subcloned downstream from the promoter using restriction enzymes to ensure that the DNA is inserted in proper orientation with respect to the promoter so that the DNA can be expressed. Once the isolated and purified DNA segment is operably linked to a promoter, the expression cassette so formed can be subcloned into a plasmid or other vectors.

2. Targeting Sequences

Additionally, expression cassettes can be constructed and employed to target the product of the isolated and purified DNA sequence or segment to an intracellular compartment within plant cells or to direct a protein to the extracellular environment. This can generally be achieved by joining a DNA sequence encoding a transit or signal peptide sequence to the coding sequence of the isolated and purified DNA sequence. The resultant transit, or signal, peptide will transport the protein to a particular intracellular, or extracellular destination, respectively, and can then be post-translationally removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. Nos. 5,258,300 and 5,593,963.

The isolated and purified DNA segment can be directed to a particular organelle, such as the chloroplast rather than to the cytoplasm. Thus, the expression cassette can further be comprised of a chloroplast transit peptide encoding DNA sequence operably linked between a promoter and the isolated and purified DNA segment (for a review of plastid targeting peptides, see Heijne et al. (1989); Keegstra et al. (1989). This is exemplified by the use of the rbcS (RuBISCO) transit peptide that targets proteins specifically to plastids.

A chloroplast transit peptide can be used. A chloroplast transit peptide is typically 40 to 70 amino acids in length and functions post-translationally to direct a protein to the chloroplast. The transit peptide is cleaved either during or just after import into the chloroplast to yield the mature protein. The complete copy of the isolated and purified DNA segment may contain a chloroplast transit peptide sequence. In that case, it may not be necessary to combine an exogenously obtained chloroplast transit peptide sequence into the expression cassette.

Chloroplast transit peptide encoding sequences can be obtained from a variety of plant nuclear genes, so long as the products of the genes are expressed as preproteins comprising an amino terminal transit peptide and transported into chloroplast. Examples of plant gene products known to include such transit peptide sequences include, but are not limited to, the small subunit of ribulose biphosphate carboxylase, ferredoxin, chlorophyll a/b binding protein, chloroplast ribosomal proteins encoded by nuclear genes, certain heat shock proteins, amino acid biosynthetic enzymes such as acetolactate acid synthase, 3-enolpyruvylphosphoshikimate synthase, dihydrodipicolinate synthase, and the like. Alternatively, the DNA fragment coding for the transit peptide may be chemically synthesized either wholly or in part from the known sequences of transit peptides such as those listed above. Furthermore, the transit peptide may compromise sequences derived from transit peptides from more than one source and may include a peptide sequence derived from the amino-terminal region of the mature protein that in its native state is linked to a transit peptide, e.g., see U.S. Pat. No. 5,510,471.

Regardless of the source of the DNA fragment coding for the transit peptide, it should include a translation initiation codon and an amino acid sequence that is recognized by and will function properly to facilitate import of a polypeptide into chloroplasts of the host plant. Attention should also be given to the amino acid sequence at the junction between the transit peptide and the protein encoded by the isolated and purified DNA segment where it is cleaved to yield the mature enzyme. Certain conserved amino acid sequences have been identified and may serve as a guideline. Precise fusion of the transit peptide coding sequence with the isolated and purified DNA segment coding sequence may require manipulation of one or both DNA sequences to introduce, for example, a convenient restriction site. This may be accomplished by methods including site-directed mutagenesis, insertion of chemically synthesized oligonucleotide linkers, and the like.

Once obtained, the chloroplast transit peptide sequence can be appropriately linked to the promoter and the isolated and purified DNA segment in an expression cassette using standard methods. Briefly, a plasmid containing a promoter functional in plant cells and having multiple cloning sites downstream can be constructed as described in Jefferson, cited supra. The chloroplast transit peptide sequence can be inserted downstream from the promoter using restriction enzymes. The isolated and purified DNA segment can then be inserted immediately downstream from and in frame with the 3¢ terminus of the chloroplast transit peptide sequence so that the chloroplast transit peptide is linked to the amino terminus of the protein encoded by the isolated and purified DNA segment. Once formed, the expression cassette can be subcloned into other plasmids or vectors.

Alternatively, targeting of the gene product to an intracellular compartment within plant cells may also be achieved by direct delivery of an isolated and purified DNA segment to the intracellular compartment. For example, an expression cassette encoding a protein, the presence of which is desired in the chloroplast, may be directly introduced into the chloroplast genome using the method described in U.S. Pat. No. 5,451,513.

It may be useful to target DNA itself within a cell. For example, it may be useful to target an introduced isolated and purified DNA to the nucleus, as this may increase the frequency of transformation. Nuclear targeting sequences that function in plants are known, e.g., the Agrobacterium virD protein is known to target DNA sequences to the nucleus of a plant cell (Herrera-Estrella et al., 1990). Within the nucleus itself, it would be useful to target a gene in order to achieve site-specific integration. For example, it would be useful to have a gene introduced through transformation replace an existing gene in the cell.

3. 3' Sequences

When the expression cassette is to be introduced into a plant cell, the expression cassette can also optionally include plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences.

Preferred 3' elements are derived from those from the nopaline synthase gene of *Agrobacterium tumefaciens* (Bevan et al., 1983), the terminator for the T7 transcript from the *Agrobacterium tumefaciens*, T-DNA and the 3' end of the protease inhibitor I or II genes from potato or tomato, although other 3' elements known to those of skill in the art can also be employed. These 3' nontranslated regulatory sequences can be obtained as described in *Methods in Enzymology* (1987) or are already present in plasmids available from commercial sources such as Clontech (Palo Alto, Calif.). The 3' nontranslated regulatory sequences can be operably linked to the 3' terminus of the isolated and purified DNA segment by standard methods.

4. Marker Genes

In order to improve the ability to identify transformants, one may desire to employ one or more selectable marker genes or reporter genes as, or in addition to, the expressible isolated and purified DNA segment(s). "Marker genes" or "reporter genes" are genes that impart a distinct phenotype to cells expressing the marker gene and thus allow such transformed cells to be distinguished from cells that do not have the gene. Such genes may encode either a selectable or screenable marker, depending on whether the marker confers a trait that one can "select" for by chemical means, i.e., through the use of a selective agent (e.g., a herbicide, antibiotic, or the like), or whether it is simply a "reporter" trait that one can identify through observation or testing, i.e., by "screening" (e.g., the R-locus trait). Of course, many examples of suitable marker genes or reporter genes are known to the art and can be employed in the practice of the invention.

Included within the terms selectable or screenable marker genes are also genes that encode a "secretable marker" whose secretion can be detected as a means of identifying or selecting for transformed cells. Examples include markers that encode a secretable antigen that can be identified by antibody interaction, or even secretable enzymes that can be detected by their catalytic activity. Secretable proteins fall into a number of classes, including small, diffusible proteins detectable, e.g., by ELISA, and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). The use of the HPRG (Stiefel et al., 1990) is preferred as this molecule is well characterized in terms of molecular biology, expression, and protein structure. However, any one of a variety of extensins and/or glycine-rich wall proteins (Keller et al., 1989) could be modified by the addition of an antigenic site to create a screenable marker.

Elements of the present disclosure are exemplified in detail through the use of particular marker genes. However in light of this disclosure, numerous other possible selectable and/or screenable marker genes will be apparent to those of skill in the art in addition to the one set forth hereinbelow. Therefore, it will be understood that the following discussion is exemplary rather than exhaustive. In light of the techniques disclosed herein and the general recombinant techniques that are known in the art, the present invention renders possible the introduction of any gene, including marker genes, into a recipient cell to generate a transformed monocot.

a. Selectable Markers

Possible selectable markers for use in connection with the present invention include, but are not limited to, a neo gene (Potrykus et al., 1985) that codes for kanamycin resistance and can be selected for using kanamycin, G418, and the like; a bar gene that codes for bialaphos resistance; a gene that encodes an altered EPSP synthase protein (Hinchee et al., 1988) thus conferring glyphosate resistance; a nitrilase gene such as bxn from *Klebsiella ozaenae* that confers resistance to bromoxynil (Stalker et al., 1988); a mutant acetolactate synthase gene (ALS) or acetohydroxyacid synthase gene (AHAS) that confers resistance to imidazolinone, sulfonylurea or other ALS-inhibiting chemicals (European Patent Application 154,204); a methotrexate-resistant DHFR gene (Thillet et al., 1988); a dalapon dehalogenase gene that confers resistance to the herbicide dalapon (U.S. Pat. No. 5,780,708); or a mutated anthranilate synthase gene that confers resistance to 5-methyl tryptophan (PCT Publication No. WO 97/26366). Where a mutant EPSP synthase gene is employed, additional benefit may be realized through the incorporation of a suitable chloroplast transit peptide, CTP (U.S. Pat. No. 4,940,835). See also, Lundquist et al., U.S. Pat. No. 5,508,468.

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes* (U.S. Pat. No. 5,550,318, which is incorporated by reference herein). The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death. The success in using this selective system in conjunction with monocots was particularly surprising because of the major difficulties that have been reported in transformation of cereals (Potrykus, 1989).

b. Screenable Markers or Reporter Genes

Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xyle gene (Zukowsky et al., 1983), which encodes a catechol dioxygenase that can convert chromogenic catechols; an α-amylase gene (Ikuta et al., 1990); a tyrosinase gene (Katz et al., 1983), which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., 1986), which allows for bioluminescence detection; or even an aequorin gene (Prasher et al., 1985), which may be employed in calcium-sensitive bioluminescence detection, or a green fluorescent protein gene (Niedz et al., 1995).

Genes from the R gene complex are contemplated to be particularly useful as screenable markers. The R gene complex encodes a protein that acts to regulate the production of anthocyanin pigments in most seed and plant tissue. Maize lines can have one, or as many as four, R alleles that combine to regulate pigmentation in a developmental and tissue specific manner. Thus, an R gene introduced into such cells will cause the expression of a red pigment and, if stably incorporated, can be visually scored as a red sector. If a line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TR112, a K55 derivative that is r–g, b, P1. Alternatively any genotype of maize can be utilized if the C1 and R alleles are introduced together.

It is further proposed that R gene regulatory regions may be employed in chimeric constructs in order to provide mechanisms for controlling the expression of chimeric genes. More diversity of phenotypic expression is known at the R locus than at any other locus (Coe et al., 1988). It is contemplated that regulatory regions obtained from regions 5' to the structural R gene would be valuable in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

5. Transgenes for Modification

The present invention provides methods and compositions for the transformation of plant cells with genes in addition to, or other than, marker genes. Such transgenes will often be genes that direct the expression of a particular protein or polypeptide product, but they may also be DNA segments that are not expressed, e.g., transposons such as Ds that do not direct their own tranposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to the recipient cells will often depend on the purpose of the transformation. One of the major purposes of transformation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food or feed content and makeup; physical appearance; male sterility; dry down; standability; prolificacy; starch properties; oil quantity and quality; and the like. One may desire to incorporate one or more genes conferring any such desirable trait or traits, such as, for example, a gene or genes encoding herbicide resistance.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. For example, plasmids bearing the bar and aroA expression units in either convergent, divergent, colinear orientation, are considered to be particularly useful. Further preferred combinations are those of an insect resistance gene, such as a Bt gene, along with a protease inhibitor gene such as pinII, or the use of bar or another selectable marker gene in combination with either of the above genes. Of course, any two or more transgenes of any description, such as those conferring herbicide, insect, disease (viral, bacterial, fungal, nematode) or drought resistance, male sterility, dry down, standability, prolificacy, starch properties, oil quantity and quality, or those increasing yield or nutritional quality may be employed as desired.

a. Herbicide Resistance

The DNA segments encoding phosphinothricin acetyltransferase (bar and pat), EPSP synthase encoding genes conferring resistance to glyphosate, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP Synthase), is normally inhibited by the herbicide N-(phosphonomethyl)glycine (glyphosate) in plants and most microorganisms. However, genes are known that encode glyphosate-resistant EPSP synthase enzymes, including mutated EPSPS genes, e.g., the *Salmonella typhimurium* aroA CT7 mutant (Comai et al., 1985) and the naturally occurring glyphosate resistant EPSPS from Agrobacterium, CP4 (U.S. Pat. No. 5,627,061). These genes are particularly contemplated for use in plant transformation. The deh gene encodes the enzyme dalapon dehalogenase and confers resistance to the herbicide dalapon (U.S. Pat. No. 5,780,708). The bxn gene codes for a specific nitrilase enzyme that converts bromoxynil to a non-herbicidal degradation product.

b. Insect Resistance

Potential insect resistance genes that can be introduced include *Bacillus thuringiensis* crystal toxin genes or Bt genes (Watrud et al., 1985). Bt genes may provide resistance to economically important lepidopteran or coleopteran pests such as European Corn Borer (ECB) and Western Corn Rootworm, respectively. It is contemplated that preferred Bt genes for use in the transformation protocols disclosed herein will be those in which the coding sequence has been modified to effect increased expression in plants, and more particularly, in maize. Means for preparing synthetic genes are well known in the art and are disclosed in, for example, U.S. Pat. No. 5,500,365 and U.S. Pat. No. 5,689,052, each of the disclosures of which are specifically incorporated herein by reference in their entirety. Examples of such modified Bt toxin genes include a synthetic Bt CryIA(b) gene (Perlak et al., 1991), and the synthetic CryIAC gene termed 1800b (U.S. Pat. No. 5,590,390). Some examples of other Bt toxin genes known to those of skill in the art are given in Table 2 below.

TABLE 2

Bacillus thuringiensis δ-Endotoxin Genes[a]

| New Nomenclature | Old Nomenclature | GenBank Accession |
|---|---|---|
| Cry1Aa | CryIA(a) | M11250 |
| Cry1Ab | CryIA(b) | M13898 |
| Cry1Ac | CryIA(c) | M11068 |
| Cry1Ad | CryIA(d) | M73250 |
| Cry1Ae | CryIA(e) | M65252 |
| Cry1Ba | CryIB | X06711 |
| Cry1Bb | ET5 | L32020 |
| Cry1Bc | PEG5 | Z46442 |
| Cry1Bd | CryE1 | U70726 |
| Cry1Ca | CryIC | X07518 |
| Cry1Cb | CryIC(b) | M97880 |
| Cry1Da | CryID | X54160 |
| Cry1Db | PrtB | Z22511 |
| Cry1Ea | CryIE | X53985 |
| Cry1Eb | CryIE(b) | M73253 |
| Cry1Fa | CryIF | M63897 |
| Cry1Fb | PrtD | Z22512 |
| Cry1Ga | PrtA | Z22510 |
| Cry1Gb | CryH2 | U70725 |
| Cry1Ha | PrtC | Z22513 |
| Cry1Hb |  | U35780 |
| Cry1Ia | CryV | X62821 |
| Cry1Ib | CryV | U07642 |
| Cry1Ja | ET4 | L32019 |
| Cry1Ib | ET1 | U31527 |
| Cry1K |  | U28801 |
| Cry2Aa | CRyIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry6A | CryVIA | L07022 |
| Cry6B | CryVIB | L07024 |
| Cry7Aa | CryIIIC | M64478 |
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | CryIG | X58120 |
| Cry9B | CryIX | X75019 |
| Cry9C | CryIH | Z37527 |
| Cry10A | CryIVC | M12662 |
| Cry11A | CryIVD | M31737 |
| Cry11B | Jeg80 | X86902 |
| Cry12A | CryVB | L07027 |
| Cry13A | CryVC | L07023 |
| Cry14A | CryVD | U13955 |

TABLE 2-continued

Bacillus thuringiensis δ-Endotoxin Genes[a]

| New Nomenclature | Old Nomenclature | GenBank Accession |
|---|---|---|
| Cry15A | 34kDa | M76442 |
| Cry16A | cbm71 | X94146 |
| Cry17A | cbm71 | X99478 |
| Cry18A | CryBP1 | X99049 |
| Cry19A | Jeg65 | Y08920 |
| Cyt1Aa | CytA | X03182 |
| Cyt1Ab | CytM | X98793 |
| Cyt2A | CytB | Z14147 |
| Cyt2B | CytB | U52043 |

[a]Adapted from: http://epunix.biols.susx.ac.uk/Home/Neil_Crickmore/Bt/index.html Protease inhibitors also may provide insect resistance (Johnson et al., 1989), and thus will have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered to produce synergistic insecticidal activity. Other genes that encode inhibitors of the insect's digestive system, or those that encode enzymes or co-factors that facilitate the production of inhibitors, also may be useful. This group may be exemplified by oryzacystatin and amylase inhibitors such as those from wheat and barley.

Also, genes encoding lectins may confer additional or alternative insecticide properties. Lectins (originally termed phytohemagglutinins) are multivalent carbohydrate-binding proteins that have the ability to agglutinate red blood cells from a range of species. Lectins have been identified recently as insecticidal agents with activity against weevils, ECB and rootworm (Murdock et al., 1990; Czapla & Lang, 1990). Lectin genes contemplated to be useful include, for example, barley and wheat germ agglutinin (WGA) and rice lectins (Gatehouse et a., 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, also may result in insecticidal activity, or perhaps cause cessation of metamorphosis (Hammock et al., 1990).

Transgenic plants expressing genes that encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant plants. Genes that code for activities that affect insect molting, such as those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests also are encompassed by the present invention. It may be possible, for instance, to confer insecticidal activity on a plant by altering its sterol composition. Sterols are obtained by insects from their diet and are used for hormone synthesis and membrane stability. Therefore, alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity that may be resistant to insect feeding.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from Tripsacum and that these novel genes will be useful in conferring resistance to insects. It is known that the basis of insect resistance in Tripsacum is genetic, because said resistance has been transferred to *Zea mays* via sexual crosses (Branson and Guss, 1972). It further is anticipated that other cereal, monocot or dicot plant species may have genes encoding proteins that are toxic to insects that would be useful for producing insect resistant plants.

Further genes encoding proteins characterized as having potential insecticidal activity also may be used as transgenes in accordance herewith. Such genes include, for example, the cowpea trypsin inhibitor (CpTI; Hilder et al., 1987), which may be used as a rootworm deterrent; genes encoding avermectin (Avermectin and Abamectin., Campbell, 1989; Ikeda et al., 1987), which may prove particularly useful as a corn rootworm deterrent; ribosome inactivating protein genes; and even genes that regulate plant structures. Transgenic including anti-insect antibody genes and genes that code for enzymes that can convert a non-toxic insecticide (pro-insecticide) applied to the outside of the plant into an insecticide inside the plant also are contemplated.

c. Environment or Stress Resistance

Improvement of a plants ability to tolerate various environmental stresses such as, but not limited to, drought, excess moisture, chilling, freezing, high temperature, salt, and oxidative stress, also can be effected through expression of novel genes. As the ZMGRP promoter of the instant invention can be induced by such environmental stresses, genes conferring resistance to these conditions may find particular use with this promoter.

It is proposed that benefits may be realized in terms of increased resistance to freezing temperatures through the introduction of an "antifreeze" protein such as that of the Winter Flounder (Cutler et al., 1989) or synthetic gene derivatives thereof. Improved chilling tolerance also may be conferred through increased expression of glycerol-3-phosphate acetyltransferase in chloroplasts (Wolter et al., 1992). Resistance to oxidative stress (often exacerbated by conditions such as chilling temperatures in combination with high light intensities) can be conferred by expression of superoxide dismutase (Gupta et al., 1993), and may be improved by glutathione reductase (Bowler et al., 1992). Such strategies may allow for tolerance to freezing in newly emerged fields as well as extending later maturity higher yielding varieties to earlier relative maturity zones.

It is proposed that expression of a gene encoding hemoglobin may enhance a plant's ability to assimilate and utilize oxygen, resulting in quicker germination, faster growing or maturing crops, or higher crop yields (Holmberg et al. 1997).

It is contemplated that the expression of novel genes that favorably effect plant water content, total water potential, osmotic potential, and turgor will enhance the ability of the plant to tolerate drought. As used herein, the terms "drought resistance" and "drought tolerance" are used to confer on a plants increased resistance or tolerance to stress induced by a reduction in water availability, as compared to normal circumstances, and the ability of the plant to function and survive in lower-water environments. In this aspect of the invention it is proposed, for example, that the expression of genes encoding for the biosynthesis of osmotically-active solutes, such as polyol compounds, may impart protection against drought. Within this class are genes encoding for mannitol-L-phosphate dehydrogenase (Lee and Saier, 1983), trehalose-6-phosphate synthase (Kaasen et al., 1992), and myo-inositol O-methyl transferase (U.S. Pat. No. 5,563, 324). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., 1992, 1993). Altered water utilization in transgenic corn producing mannitol also has been demonstrated (U.S. Pat. No. 5,780,709).

Similarly, the efficacy of other metabolites in protecting either enzyme function (e.g., alanopine or propionic acid) or membrane integrity (e.g., alanopine) has been documented (Loomis et al., 1989), and therefore expression of genes encoding for the biosynthesis of these compounds might confer drought resistance in a manner similar to or complimentary to mannitol. Other examples of naturally occurring metabolites that are osmotically active and/or provide some direct protective effect during drought and/or desiccation include fructose, erythritol (Coxson et al., 1992), sorbitol, dulcitol (Karsten et al., 1992), glucosylglycerol (Reed et al., 1984; Erdmann et al., 1992), sucrose, stachyose (Koster and Leopold, 1988; Blackman et al., 1992), raffinose (Bernal-Lugo and Leopold, 1992), proline (Rensburg et al., 1993), glycine betaine, ononitol and pinitol (Vernon and Bohnert, 1992). Continued canopy growth and increased reproductive fitness during times of stress will be augmented by introduction and expression of genes such as those controlling the osmotically active compounds discussed above and other such compounds. Currently preferred genes that promote the synthesis of an osmotically active polyol compound are genes that encode the enzymes mannitol-1-phosphate dehydrogenase, trehalose-6-phosphate synthase and myo-inositol 0-methyltransferase.

It is contemplated that the expression of specific proteins also may increase drought tolerance. Three classes of late embryogenic proteins (LEP) have been assigned based on structural similarities (see Dure et al., 1989). All three classes of LEAs have been demonstrated in maturing (i.e., desiccating) seeds. Within these 3 types of LEA proteins, the Type-II (dehydrin-type) have generally been implicated in drought and/or desiccation tolerance in vegetative plant parts (i.e., Mundy and Chua, 1988; Piatkowski et al., 1990; Yamaguchi-Shinozaki et al., 1992). Recently, expression of a Type-III LEA (HVA-1) in tobacco was found to influence plant height, maturity and drought tolerance (Fitzpatrick, 1993). In rice, expression of the HVA-1 gene influenced tolerance to water deficit and salinity (Xu et al., 1996). Expression of structural genes from all three LEA groups may therefore confer drought tolerance. Other types of proteins induced during water stress include thiol proteases, aldolases and transmembrane transporters (Guerrero et al., 1990), which may confer various protective and/or repair-type functions during drought stress. It also is contemplated that genes that effect lipid biosynthesis and hence membrane composition might also be useful in conferring drought resistance on the plant.

Many of these genes for improving drought resistance have complementary modes of action. Thus, it is envisaged that combinations of these genes might have additive and/or synergistic effects in improving drought resistance in crop plants such as, for example, corn, soybean, cotton, or wheat. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor-induced promoter (such as the promoters for the turgor-induced genes described in Guerrero et al., 1990 and Shagan et al., 1993, which are incorporated herein by reference Inducible, spatial and temporal expression patterns of these genes may enable plants to better withstand stress.

It is proposed that expression of genes that are involved with specific morphological traits that allow for increased water extractions from drying soil would be of benefit. For example, introduction and expression of genes that alter root characteristics may enhance water uptake. It also is contemplated that expression of genes that enhance reproductive fitness during times of stress would be of significant value. For example, expression of genes that improve the synchrony of pollen shed and receptiveness of the female flower parts, i.e., silks, would be of benefit. In addition it is proposed that expression of genes that minimize kernel abortion during times of stress would increase the amount of grain to be harvested and hence be of value.

Given the overall role of water in determining yield, it is contemplated that enabling corn and other crop plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

d. Disease Resistance

It is proposed that increased resistance to diseases may be realized through introduction of genes into plants, for example, into monocotyledonous plants such as maize. It is possible to produce resistance to diseases caused by viruses, bacteria, fungi and nematodes. It also is contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo et al., 1988, Hemenway et al., 1988, Abel et al., 1986). It is contemplated that expression of antisense genes targeted at essential viral functions also may impart resistance to viruses. For example, an antisense gene targeted at the gene responsible for replication of viral nucleic acid may inhibit replication and lead to resistance to the virus. It is believed that interference with other viral functions through the use of antisense genes also may increase resistance to viruses. Similarly, ribozymes could be used in this context. Further, it is proposed that it may be possible to achieve resistance to viruses through other approaches, including, but not limited to the use of satellite viruses. Examples of viral and viral-like diseases, for which one could introduce resistance to in a transgenic plant in accordance with the instant invention, are listed below, in Table 3.

TABLE 3

Plant Virus and Virus-like Diseases

| DISEASE | CAUSATIVE AGENT |
| --- | --- |
| American wheat striate (wheat striate mosaic) | American wheat striate mosaic virus mosaic (AWSMV) |
| Barley stripe mosaic | Barley stripe mosaic virus (BSMV) |
| Barley yellow dwarf | Barley yellow dwarf virus (BYDV) |
| Brome mosaic | Brome mosaic virus (BMV) |
| Cereal chlorotic mottle* | Cereal chlorotic mottle virus (CCMV) |
| Corn chlorotic vein banding (Brazilian mosaic)[1] | Corn chlorotic vein banding virus (CCVBV) |
| Corn lethal necrosis | Virus complex (chlorotic mottle virus (MCMV) and dwarf mosaic virus (MDMV) A or B or Wheat streak mosaic virus (WSMV)) |
| Cucumber mosaic | Cucumber mosaic virus (CMV) |
| Cynodon chlorotic streak*,[1] | Cynodon chlorotic streak virus (CCSV) |
| Johnsongrass mosaic | Johnsongrass mosaic virus (JGMV) |
| bushy stunt | Mycoplasma-like organism (MLO) associated |
| chlorotic dwarf | chlorotic dwarf virus (MCDV) |
| chlorotic mottle | chlorotic mottle virus (MCMV) |
| dwarf mosaic | dwarf mosaic virus (MDMV) strains A, D, E and F |
| leaf fleck | leaf fleck virus (MLFV) |
| line* | line virus (MLV) |
| mosaic (corn leaf stripe, enanismo rayado) | mosaic virus (MMV) |
| mottle and chlorotic stunt[1] | mottle and chlorotic stunt virus* |
| pellucid ringspot* | pellucid ringspot virus (MPRV) |
| raya gruesa*,[1] | raya gruesa virus (MRGV) |
| rayado fino* (fine striping disease) | rayado fino virus (MRFV) |
| red leaf and red stripe* | Mollicute |
| red stripe* | red stripe virus (MRSV) |
| ring mottle* | ring mottle virus (MRMV) |
| rio IV* | rio cuarto virus (MRCV) |
| rough dwarf* (nanismo ruvido) | rough dwarf virus (MRDV) (= Cereal tillering disease virus*) |
| sterile stunt* | sterile stunt virus (strains of barley yellow striate virus) |
| streak* | streak virus (MSV) |
| stripe (chlorotic stripe, hoja blanca) | stripe virus |
| stunting*,[1] | Stunting virus |
| tassel abortion* | tassel abortion virus (MTAV) |
| vein enation* | vein enation virus (MVEV) |
| wallaby ear* | wallaby ear virus (MWEV) |
| white leaf* | white leaf virus |
| white line mosaic | white line mosaic virus (MWLMV) |
| Millet red leaf* | Millet red leaf virus (MRLV) |
| Northern cereal mosaic* | Northern cereal mosaic virus (NCMV) |
| Oat pseudorosette* (zakuklivanie) | Oat pseudorosette virus |
| Oat sterile dwarf* | Oat sterile dwarf virus (OSDV) |
| Rice black-streaked dwarf* | Rice black-streaked dwarf virus (RBSDV) |
| Rice stripe* | Rice stripe virus (RSV) |
| Sorghum mosaic | Sorghum mosaic virus (SrMV), formerly sugarcane mosaic virus (SCMV) strains H, I and M |
| Sugarcane Fiji disease* | Sugarcane Fiji disease virus (FDV) |
| Sugarcane mosaic | Sugarcane mosaic virus (SCMV) strains A, B, D, E, SC, BC, Sabi and MB (formerly MDMV-B) |
| Vein enation*,[1] | Virus? |
| Wheat spot mosaic[1] | Wheat spot mosaic virus (WSMV) |

*Not known to occur naturally on corn in the United States.
[1]Minor viral disease.

It is proposed that increased resistance to diseases caused by bacteria and fungi also may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences that are inhibitory to growth of bacteria and other microorganisms. For example, the classes of peptides referred to as cecropins and magainins inhibit growth of many species of bacteria and fungi. It is proposed that expression of PR proteins in monocotyledonous plants may be useful in conferring resistance to bacterial disease. These genes are induced following pathogen attack on a host plant and have been divided into at least five classes of proteins (Bol et al., 1990). Included amongst the PR proteins are $\beta$-1,3-glucanases, chitinases, and osmotin and other proteins that are believed to function in plant resistance to disease organisms. Other genes have been identified that have antiflimgal properties, e.g., UDA (stinging nettle lectin), hevein (Broakaert et al., 1989; Barkai-Golan et al., 1978), and sor1 conferring resistance to photosensitizing toxins (Ehrenshaft et al., 1999). It is known that certain plant diseases are caused by the production of phytotoxins. It is proposed that resistance to these diseases would be achieved through expression of a novel gene that encodes an enzyme capable of degrading or otherwise inactivating the phytotoxin. It also is contemplated that expression of novel genes that alter the interactions between the host plant and pathogen may be useful in reducing the ability of the disease organism to invade the tissues of the host plant, e.g., an increase in the waxiness of the leaf cuticle or other morphological characteristics. Examples of bacterial and fungal diseases, including downy mildews, for which one could introduce resistance to in a transgenic plant in accordance with the instant invention, are listed below, in Tables 4, 5 and 6.

TABLE 4

Plant Bacterial Diseases

| DISEASE | CAUSATIVE AGENT |
|---|---|
| Bacterial leaf blight and stalk rot | *Pseudomonas avenae* subsp. *avenae* |
| Bacterial leaf spot | *Xanthomonas campestris* pv. *holcicola* |
| Bacterial stalk rot | *Enterobacter dissolvens* = *Erwinia dissolvens* |
| Bacterial stalk and top rot | *Erwinia carotovora* subsp. *carotovora, Erwinia chrysanthemi* pv. *zeae* |
| Bacterial stripe | *Pseudomonas andropogonis* |
| Chocolate spot | *Pseudomonas syringae* pv. *coronafaciens* |
| Goss's bacterial wilt and blight (leaf freckles and wilt) | *Clavibacter michiganensis* subsp. *nebraskensis* = *Corynebacterium michiganense* pv. *nebraskense* |
| Holcus spot | *Pseudomonas syringae* pv. *syringae* |
| Purple leaf sheath | Hemiparasitic bacteria + (See under Fungi) |
| Seed rot-seedling blight | *Bacillus subtilis* |
| Stewart's disease (bacterial wilt) | *Pantoea stewartii* = *Erwinia stewartii* |
| Corn stunt (achapparramiento, stunt, Mesa Central or Rio Grande stunt) | *Spiroplasma kunkelii* |

TABLE 5

Plant Fungal Diseases

| DISEASE | PATHOGEN |
|---|---|
| Anthracnose leaf blight and anthracnose stalk rot | *Colletotrichum graminicola* (teleomorph: *Glomerella graminicola* Politis), *Glomerella tucumanensis* (anamorph: *Glomerella falcatum* Went) |
| Aspergillus ear and kernel rot | *Aspergillus flavus* Link:Fr. |
| Banded leaf and sheath spot* | *Rhizoctonia solani* Kühn = *Rhizoctonia microsclerotia* J. Matz (teleomorph: *Thanatephorus cucumeris*) |
| Black bundle disease | *Acremonium strictum* W. Gams = *Cephalosporium acremonium* Auct. non Corda |
| Black kernel rot* | *Lasiodiplodia theobromae* = *Botryodiplodia theobromae* |
| Borde blanco* | *Marasmiellus* sp. |
| Brown spot (black spot, stalk rot) | *Physoderma maydis* |
| Cephalosporium kernel rot | *Acremonium strictum* = *Cephalosporium acremonium* |
| Charcoal rot | *Macrophomina phaseolina* |
| Corticium ear rot* | *Thanatephorus cucumeris* = *Corticium sasakii* |
| Curvularia leaf spot | *Curvularia clavata, C. eragrostidis,* = *C. maculans* (teleomorph: *Cochliobolus eragrostidis*), *Curvularia inaequalis, C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis, C. tuberculata* (teleomorph: *Cochliobolus tuberculatus*) |
| Didymella leaf spot* | *Didymella exitalis* |
| Diplodia ear rot and stalk rot | *Diplodia frumenti* (teleomorph: *Botryosphaeria festucae*) |
| Diplodia ear rot, stalk rot, seed rot and seedling blight | *Diplodia maydis* = *Stenocarpella maydis* |
| Diplodia leaf spot or leaf streak | *Stenocarpella macrospora* = *Diplodia macrospora* |

*Not known to occur naturally on corn in the United States.

TABLE 6

Plant Downy Mildews

| DISEASE | CAUSATIVE AGENT |
|---|---|
| Brown stripe downy mildew* | *Sclerophthora rayssiae* var. *zeae* |
| Crazy top downy mildew | *Sclerophthora macrospora* = *Sclerospora macrospora* |
| Green ear downy mildew (graminicola downy mildew) | *Sclerospora graminicola* |
| Java downy mildew* | *Peronosclerospora maydis* = *Sclerospora maydis* |
| Philippine downy mildew* | *Peronosclerospora philippinensis* = *Sclerospora philippinensis* |
| Sorghum downy mildew | *Peronosclerospora sorghi* = *Sclerospora sorghi* |
| Spontaneum downy mildew* | *Peronosclerospora spontanea* = *Sclerospora spontanea* |
| Sugarcane downy mildew* | *Peronosclerospora sacchari* = *Sclerospora sacchari* |
| Dry ear rot (cob, kernel and stalk rot) | *Nigrospora oryzae* (teleomorph: *Khuskia oryzae*) |
| Ear rots, minor | *Alternaria alternata* = *A. tenuis, Aspergillus glaucus, A. niger, Aspergillus* spp., |

TABLE 6-continued

Plant Downy Mildews

| DISEASE | CAUSATIVE AGENT |
|---|---|
| | *Botrytis cinerea* (teleomorph: *Botryotinia fuckeliana*), Cunninghamella sp., *Curvularia pallescens*, *Doratomyces stemonitis* = *Cephalotrichum stemonitis*, *Fusarium culmorum*, *Gonatobotrys simplex*, *Pithomyces maydicus*, *Rhizopus microsporus* Tiegh., *R. stolonifer* = *R. nigricans*, *Scopulariopsis brumptii*. |
| Ergot* (horse's tooth, diente de caballo) | *Claviceps gigantea* (anamorph: Sphacelia sp.) |
| Eyespot | *Aureobasidium zeae* = *Kabatiella zeae* |
| Fusarium ear and stalk rot | *Fusarium subglutinans* = *F. moniliforme* var. *subglutinans* |
| Fusarium kernel, root and stalk rot, seed rot and seedling blight | *Fusarium moniliforme* (teleomorph: *Gibberella fujikuroi*) |
| Fusarium stalk rot, seedling root rot | *Fusarium avenaceum* (teleomorph: *Gibberella avenacea*) |
| Gibberella ear and stalk rot | *Gibberella zeae* (anamorph: *Fusarium graminearum*) |
| Gray ear rot | *Botryosphaeria zeae* = *Physalospora zeae* (anamorph: *Macrophoma zeae*) |
| Gray leaf spot (Cercospora leaf spot) | *Cercospora sorghi* = *C. sorghi* var. *maydis*, *C. zeae-maydis* |
| Helminthosporium root rot | *Exserohilum pedicellatum* = *Helminthosporium pedicellatum* (teleomorph: *Setosphaeria pedicellata*) |
| Hormodendrum ear rot (Cladosporium rot) | *Cladosporium cladosporioides* = *Hormodendrum cladosporioides*, *C. herbarum* (teleomorph: *Mycosphaerella tassiana*) |
| Hyalothyridium leaf spot* | *Hyalothyridium maydis* |
| Late wilt* | *Cephalosporium maydis* |
| Leaf spots, minor | *Alternaria alternata*, *Ascochyta maydis*, *A. tritici*, *A. zeicola*, *Bipolaris victoriae* = *Helminthosporium victoriae* (teleomorph: *Cochliobolus victoriae*), *C. sativus* (anamorph: *Bipolaris sorokiniana* = *H. sorokinianum* = *H. sativum*), *Epicoccum nigrum*, *Exserohilum prolatum* = *Drechslera prolata* (teleomorph: *Setosphaeria prolata*) *Graphium penicillioides*, *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anamorph: *Exserohilum turcicum* = *Helminthosporium turcicum*) |
| Northern corn leaf spot, Helminthosporium ear rot (race 1) | *Cochliobolus carbonum* (anamorph: *Bipolaris zeicola* = *Helminthosporium carbonum*) |
| Penicillium ear rot (blue eye, blue mold) | *Penicillium* spp., *P. chrysogenum*, *P. expansum*, *P. oxalicum* |
| Phaeocytostroma stalk rot and root rot | *Phaeocytostroma ambiguum*, *Phaeocytosporella zeae* |
| Phaeosphaeria leaf spot* | *Phaeosphaeria maydis* |
| Physalospora ear rot (Botryosphaeria ear rot) | *Sphaerulina maydis* *Botryosphaeria festucae* = *Physalospora zeicola* (anamorph: *Diplodia frumenti*) |
| Purple leaf sheath | Hemiparasitic bacteria and fungi |
| Pyrenochaeta stalk rot and root rot | *Phoma terrestris* = *Pyrenochaeta terrestris* |
| Pythium root rot | *Pythium* spp., *P. arrhenomanes*, *P. graminicola* |
| Pythium stalk rot | *Pythium aphanidermatum* = *P. butleri* L. |
| Red kernel disease (ear mold, leaf and seed rot) | *Epicoccum nigrum* |
| Rhizoctonia ear rot (sclerotial rot) | *Rhizoctonia zeae* (teleomorph: *Waitea circinata*) |
| Rhizoctonia root rot and stalk rot | *Rhizoctonia solani*, *Rhizoctonia zeae* |
| Root rots, minor | *Alternaria alternata*, *Cercospora sorghi*, *Dictochaeta fertilis*, *Fusarium acuminatum* (teleomorph: *Gibberella acuminata*), *F. equiseti* (teleomorph: *G. intricans*), *F. oxysporum*, *F. pallidoroseum*, *F. poae*, *F. roseum*, *G. cyanogena*, (anamorph: *F. sulphureum*), *Microdochium bolleyi*, *Mucor* sp., *Periconia circinata*, *Phytophthora cactorum*, *P. drechsleri*, *P. nicotianae* var. *parasitica*, *Rhizopus arrhizus* |
| Rostratum leaf spot (Helminthosporium leaf disease, ear and stalk rot) | *Setosphaeria rostrata*, (anamorph: *Exserohilum rostratum* = *Helminthosporium rostratum*) |
| Rust, common corn | *Puccinia sorghi* |
| Rust, southern corn | *Puccinia polysora* |
| Rust, tropical corn | *Physopella pallescens*, *P. zeae* = *Angiopsora zeae* |
| Sclerotium ear rot* (southern blight) | *Sclerotium rolfsii* Sacc. (teleomorph: *Athelia rolfsii*) |
| Seed rot-seedling blight | *Bipolaris sorokiniana*, *B. zeicola* = *Helminthosporium carbonum*, *Diplodia maydis*, *Exserohilum pedicillatum*, *Exserohilum turcicum* = *Helminthosporium turcicum*, *Fusarium avenaceum*, *F. culmorum*, *F. moniliforme*, *Gibberella zeae* (anamorph: *F. graminearum*), *Macrophomina phaseolina*, *Penicillium* spp., *Phomopsis* sp., *Pythium* spp., *Rhizoctonia solani*, *R. zeae*, *Sclerotium rolfsii*, *Spicaria* sp. |
| Selenophoma leaf spot* | *Selenophoma* sp. |
| Sheath rot | *Gaeumannomyces graminis* |
| Shuck rot | *Myrothecium gramineum* |
| Silage mold | *Monascus purpureus*, *M. ruber* |
| Smut, common | *Ustilago zeae* = *U. maydis* |
| Smut, false | *Ustilaginoidea virens* |
| Smut, head | *Sphacelotheca reiliana* = *Sporisorium holci-sorghi* |
| Southern corn leaf blight and stalk rot | *Cochliobolus heterostrophus* (anamorph: *Bipolaris maydis* = *Helminthosporium maydis*) |
| Southern leaf spot | *Stenocarpella macrospora* = *Diplodia macrospora* |
| Stalk rots, minor | *Cercospora sorghi*, *Fusarium epiphaeria*, *F. merismoides*, *F. oxysporum* Schlechtend, *F. poae*, *F. roseum*, *F. solani* (teleomorph: *Nectria haematococca*), *F. tricinctum*, *Mariannaea elegans*, *Mucor* |

TABLE 6-continued

Plant Downy Mildews

| DISEASE | CAUSATIVE AGENT |
|---|---|
|  | sp., *Rhopographus zeae*, *Spicaria* sp. |
| Storage rots | *Aspergillus* spp., *Penicillium* spp. and other fungi |
| Tar spot* | *Phyllachora maydis* |
| Trichoderma ear rot and root rot | *Trichoderma viride* = *T. lignorum* teleomorph: *Hypocrea* sp. |
| White ear rot, root and stalk rot | *Stenocarpella maydis* = *Diplodia zeae* |
| Yellow leaf blight | *Ascochyta ischaemi*, *Phyllosticta maydis* (teleomorph: *Mycosphaerella zeae-maydis*) |
| Zonate leaf spot | *Gloeccercospora sorghi* |

*Not known to occur naturally on corn in the United States.

Plant parasitic nematodes are a cause of disease in many plants, including cereal plants such as maize, barley, wheat, rye and rice. It is proposed that it would be possible to make plants resistant to these organisms through the expression of novel gene products. It is anticipated that control of nematode infestations would be accomplished by altering the ability of the nematode to recognize or attach to a host plant and/or enabling the plant to produce nematicidal compounds, including but not limited to proteins. It is known that certain endotoxins derived from *Bacillus thuringiensis* are nematicidal (Bottjer et al., 1985; U.S. Pat. No. 5,831,011). Examples of nematode-associated plant diseases, for which one could introduce resistance to in a transgenic plant in accordance with the invention are given below, in Table 7.

TABLE 7

Parasitic Nematodes

| DISEASE | PATHOGEN |
|---|---|
| Awl | *Dolichodorus* spp., *D. heterocephalus* |
| Bulb and stem (Europe) | *Ditylenchus dipsaci* |
| Burrowing | *Radopholus similis* |
| Cyst | *Heterodera avenae*, *H. zeae*, *Punctodera chalcoensis* |
| Dagger | *Xiphinema* spp., *X. americanum*, *X. mediterraneum* |
| False root-knot | *Nacobbus dorsalis* |
| Lance, Columbia | *Hoplolaimus columbus* |
| Lance | *Hoplolaimus* spp., *H. galeatus* |
| Lesion | *Pratylenchus* spp., *P. brachyurus*, *P. crenatus*, *P. hexincisus*, *P. neglectus*, *P. penetrans*, *P. scribneri*, *P. thornei*, *P. zeae* |
| Needle | *Longidorus* spp., *L. breviannulatus* |
| Ring | *Criconemella* spp., *C. ornata* |
| Root-knot | *Meloidogyne* spp., *M. chitwoodi*, *M. incognita*, *M. javanica* |
| Spiral | *Helicotylenchus* spp. |
| Sting | *Belonolaimus* spp., *B. longicaudatus* |
| Stubby-root | *Paratrichodorus* spp., *P. christiei*, *P. minor*, *Quinisulcius acutus*, *Trichodorus* spp. |
| Stunt | *Tylenchorhynchus dubius* | e. Mycotoxin Reduction/Elimination

Production of mycotoxins, including aflatoxin and fumonisin, by fungi associated with monocotyledonous plants such as cereal plants, including maize, barley, wheat, rye or rice, is a significant factor in rendering the grain not useful. These fungal organisms do not cause disease symptoms and/or interfere with the growth of the plant, but they produce chemicals (mycotoxins) that are toxic to animals. It is contemplated that inhibition of the growth of these fungi would reduce the synthesis of these toxic substances and therefore reduce grain losses due to mycotoxin contamination. It also is proposed that it may be possible to introduce novel genes into monocotyledonous plants such as that would inhibit synthesis of the mycotoxin. Further, it is contemplated that expression of a novel gene that encodes an enzyme capable of rendering the mycotoxin nontoxic would be useful in order to achieve reduced mycotoxin contamination of grain. The result of any of the above mechanisms would be a reduced presence of mycotoxins on grain.

f. Grain Composition or Quality

Genes may be introduced into monocotyledonous plants, particularly commercially important cereals, such as maize, barley, wheat, rye or rice, to improve the grain for which the cereal is primarily grown. A wide range of novel transgenic plants produced in this manner may be envisioned depending on the particular end use of the grain.

The largest use of grain is for feed or food. Introduction of genes that alter the composition of the grain may greatly enhance the feed or food value. The primary components of grain are starch, protein, and oil. Each of these primary components of grain may be improved by altering its level or composition. Several examples may be mentioned for illustrative purposes, but in no way provide an exhaustive list of possibilities.

The protein of cereal grains including maize, barley, wheat, rye and rice is suboptimal for feed and food purposes especially when fed to monogastric animals such as pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after corn is supplemented with other inputs for feed formulations. For example, when corn is supplemented with soybean meal to meet lysine requirements methionine becomes limiting. The levels of these essential amino acids in seeds and grain may be elevated by mechanisms that include, but are not limited to, the introduction of genes to increase the biosynthesis of the amino acids, decrease the degradation of the amino acids, increase the storage of the amino acids in proteins, direct the storage of amino acids in proteins comprising a nutritionally enhanced balance of amino acids, or increase transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway that are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyze steps in the catabolic pathways such as the enzyme lysine-ketoglutarate reductase. It is anticipated that it may be desirable to target expression of genes relating to amino acid biosynthesis to the endosperm or embryo of the seed. More preferably, the gene will be targeted to the embryo. It will also be preferable for genes encoding proteins involved in amino acid biosynthesis to target the protein to a plastid using a plastid transit peptide sequence.

The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. Examples may include the introduction of DNA that decreases the expression of members of the zein family of storage proteins. This DNA may encode ribozymes or antisense sequences directed to impairing expression of zein proteins or expression of regulators of zein expression such as the opaque-2 gene product. It also is proposed that the protein composition of the grain may be modified through the phenomenon of co-suppression, i.e., inhibition of expression of an endogenous gene through the expression of an identical structural gene or gene fragment introduced through transformation (Goring et al., 1991; PCT Publication No. WO 98/26064). Additionally, the introduced DNA may encode enzymes that degrade zeins. The decreases in zein expression that are achieved may be accompanied by increases in proteins with more desirable amino acid composition or increases in other major seed constituents such as starch. Alternatively, a chimeric gene may be introduced that comprises a coding sequence for a native protein of adequate amino acid composition such as for one of the globulin proteins or 10 kD delta zein or 20 kD delta zein or 27 kD gamma zein of and a promoter or other regulatory sequence designed to elevate expression of said protein. The coding sequence of the gene may include additional or replacement codons for essential amino acids. Further, a coding sequence obtained from another species, or, a partially or completely synthetic sequence encoding a completely unique peptide sequence designed to enhance the amino acid composition of the seed may be employed. It is anticipated that it may be preferable to target expression of these transgenes encoding proteins with superior composition to the endosperm of the seed.

The introduction of genes that alter the oil content of the grain may be of value. Increases in oil content may result in increases in metabolizable-energy-content and density of the seeds for use in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, β-ketoacyl-ACP synthase, plus other well known fatty acid biosynthetic activities. Other possibilities are genes that encode proteins that do not possess enzymatic activity such as acyl carrier protein. Genes may be introduced that alter the balance of fatty acids present in the oil providing a more healthful or nutritive feed stuff. The introduced DNA also may encode sequences that block expression of enzymes involved in fatty acid biosynthesis, altering the proportions of fatty acids present in the grain such as described below. Some other examples of genes specifically contemplated by the inventors for use in creating transgenic plants with altered oil composition traits include 2-acetyltransferase, oleosin, pyruvate dehydrogenase complex, acetyl CoA synthetase, ATP citrate lyase, ADP-glucose pyrophosphorylase and genes of the carnitine-CoA-acetyl-CoA shuttles. It is anticipated that expression of genes related to oil biosynthesis will be targeted to the plastid, using a plastid transit peptide sequence and preferably expressed in the seed embryo.

Genes may be introduced that enhance the nutritive value of the starch component of the grain, for example by increasing the degree of branching, resulting in improved utilization of the starch, for example, in cows by delaying its metabolism. It is contemplated that alteration of starch structure may improve the wet milling properties of grain or may produce a starch composition with improved qualities for industrial utilization. It is anticipated that expression of genes related to starch biosynthesis will preferably be targeted to the endosperm of the seed.

Besides affecting the major constituents of the grain, genes may be introduced that affect a variety of other nutritive, processing, or other quality aspects of the grain as used for feed or food. For example, pigmentation of the grain may be increased or decreased. Enhancement and stability of yellow pigmentation is desirable in some animal feeds and may be achieved by introduction of genes that result in enhanced production of xanthophylls and carotenes by eliminating rate-limiting steps in their production. Such genes may encode altered forms of the enzymes phytoene synthase, phytoene desaturase, or lycopene synthase. Alternatively, unpigmented white corn is desirable for production of many food products and may be produced by the introduction of DNA that blocks or eliminates steps in pigment production pathways.

Most of the phosphorous content of the grain is in the form of phytate, a form of phosphate storage that is not metabolized by monogastric animals. Therefore, in order to increase the availability of seed phosphate, it is anticipated that one will desire to decrease the amount of phytate in seed and increase the amount of free phosphorous. It is anticipated that one can decrease the expression or activity of one of the enzymes involved in the synthesis of phytate. For example, suppression of expression of the gene encoding inositol phosphate synthetase (INOPS) may lead to an overall reduction in phytate accumulation. It is anticipated that antisense or sense suppression of gene expression may be used. Alternatively, one may express a gene in seed that will be activated, e.g., by pH, in the gastric system of a monogastric animal and will release phosphate from phytate, e.g., phytase. It is further contemplated that one may provide an alternate storage form for phosphate in the grain, wherein the storage form is more readily utilized by a monogastric animal.

Feed or food comprising primarily maize or other cereal grains possesses insufficient quantities of vitamins and must be supplemented to provide adequate nutritive value. Introduction of genes that enhance vitamin biosynthesis in seeds may be envisioned including, for example, vitamins A, E, $B_{12}$, choline, and the like. Maize grain also does not possess sufficient mineral content for optimal nutritive value. Genes that affect the accumulation or availability of compounds containing phosphorus, sulfur, calcium, manganese, zinc, and iron among others would be valuable. An example may be the introduction of a gene that reduced phytic acid production or encoded the enzyme phytase that enhances phytic acid breakdown. These genes would increase levels of available phosphate in the diet, reducing the need for supplementation with mineral phosphate.

Numerous other examples of improvement of other plants for feed and food purposes might be described. The improvements may not even necessarily involve the grain, but may, for example, improve the value of the plants for silage. Introduction of DNA to accomplish this might include sequences that alter lignin production such as those that result in the "brown midrib" phenotype associated with superior feed value for cattle.

In addition to direct improvements in feed or food value, genes also may be introduced that improve the processing of plant material and improve the value of the products resulting from the processing. For example, the primary method of processing maize is via wetmilling that may be improved though the expression of novel genes that increase the efficiency and reduce the cost of processing such as by decreasing steeping time.

Improving the value of wetmilling products may include altering the quantity or quality of starch, oil, corn gluten meal, or the components of corn gluten feed. Elevation of starch may be achieved through the identification and elimination of rate limiting steps in starch biosynthesis or by decreasing levels of the other components of the grain resulting in proportional increases in starch. An example of the former may be the introduction of genes encoding ADP-glucose pyrophosphorylase enzymes with altered regulatory activity or that are expressed at higher level. Examples of the latter may include selective inhibitors of, for example, protein or oil biosynthesis expressed during later stages of kernel development.

The properties of starch may be beneficially altered by changing the ratio of amylose to amylopectin, the size of the starch molecules, or their branching pattern. Through these changes a broad range of properties may be modified that include, but are not limited to, changes in gelatinization temperature, heat of gelatinization, clarity of films and pastes, rheological properties, and the like. To accomplish these changes in properties, genes that encode granule-bound or soluble starch synthase activity or branching enzyme activity may be introduced alone or combination. DNA such as antisense constructs also may be used to decrease levels of endogenous activity of these enzymes. The introduced genes or constructs may possess regulatory sequences that time their expression to specific intervals in starch biosynthesis and starch granule development. Furthermore, it may be worthwhile to introduce and express genes that result in the in vivo derivatization, or other modification, of the glucose moieties of the starch molecule. The covalent attachment of any molecule may be envisioned, limited only by the existence of enzymes that catalyze the derivatizations and the accessibility of appropriate substrates in the starch granule. Examples of important derivations may include the addition of functional groups such as amines, carboxyls, or phosphate groups that provide sites for subsequent in vitro derivatizations or affect starch properties through the introduction of ionic charges. Examples of other modifications may include direct changes of the glucose units such as loss of hydroxyl groups or their oxidation to aldehyde or carboxyl groups.

Oil is another product of wetmilling of corn, the value of which may be improved by introduction and expression of genes. The quantity of oil that can be extracted by wetmilling may be elevated by approaches as described for feed and food above. Oil properties also may be altered to improve its performance in the production and use of cooking oil, shortenings, lubricants or other oil-derived products or improvement of its health attributes when used in the food-related applications. Novel fatty acids also may be synthesized that upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively, DNA sequences may be introduced that slow or block steps in fatty acid biosynthesis resulting in the increase in precursor fatty acid intermediates. Genes that might be added include desaturases, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic and oleic acids. Another example is the blockage of elongation steps resulting in the accumulation of $C_8$ to $C_{12}$ saturated fatty acids.

Improvements in the other major corn wetmilling products, corn gluten meal and corn gluten feed, also may be achieved by the introduction of genes to obtain novel corn plants. Representative possibilities include but are not limited to those described above for improvement of food and feed value.

In addition, it may further be considered that a plant, such as maize or other monocots, may be used for the production or manufacturing of useful biological compounds that were either not produced at all, or not produced at the same level, in the plant previously. The novel plants producing these compounds are made possible by the introduction and expression of genes by transformation methods. The vast array of possibilities include but are not limited to any biological compound that is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, and industrial enzymes to name a few.

Further possibilities to exemplify the range of grain traits or properties potentially encoded by introduced genes in transgenic plants include grain with less breakage susceptibility for export purposes or larger grit size when processed by dry milling through introduction of genes that enhance γ-zein synthesis, popcorn with improved popping quality and expansion volume through genes that increase pericarp thickness, corn with whiter grain for food uses though introduction of genes that effectively block expression of enzymes involved in pigment production pathways, and improved quality of alcoholic beverages or sweet corn through introduction of genes that affect flavor such as the shrunken 1 gene (encoding sucrose synthase) or shrunken 2 gene (encoding ADPG pyrophosphorylase) for sweet corn.

g. Plant Agronomic Characteristics

Two of the factors determining where crop plants can be grown are the average daily temperature during the growing season and the length of time between frosts. Within the areas where it is possible to grow a particular crop, there are varying limitations on the maximal time the crop has available to grow to maturity and be harvested. For example, to be grown in a particular area is selected for its ability to mature and dry down to harvestable moisture content within the required period of time with maximum possible yield. Therefore, plants, including maize or other cereals, of varying maturities are developed for different growing locations. Apart from the need to dry down sufficiently to permit harvest, it is desirable to have maximal drying take place in the field to minimize the amount of energy required for additional post-harvest drying. Also, the more readily the grain can dry down, the more time there is available for growth and seed maturation. It is considered that genes that influence maturity and/or dry down can be identified and introduced into corn or other plants using transformation techniques to create new varieties adapted to different growing locations or the same growing location, but having improved yield to moisture ratio at harvest. Expression of genes that are involved in regulation of plant development may be especially useful, e.g., the liguleless and rough sheath genes that have been identified in corn.

It is contemplated that genes may be introduced into plants that would improve standability and other plant growth characteristics. Expression of novel genes that confer stronger stalks, improved root systems, or prevent or reduce ear droppage would be of great value to the farmer. It is proposed that introduction and expression of genes that increase the total amount of photoassimilate available by, for example, increasing light distribution and/or interception would be advantageous. In addition, the expression of genes that increase the efficiency of photosynthesis and/or the leaf canopy would further increase gains in productivity. It is contemplated that expression of a phytochrome gene in plants, including maize, may be advantageous. Expression of such a gene may reduce apical dominance, confer semi-dwarfism on a plant, and increase shade tolerance (U.S. Pat. No. 5,268,526). Such approaches would allow for increased plant populations in the field.

Delay of late season vegetative senescence would increase the flow of assimilate into the grain and thus increase yield. It is proposed that overexpression of genes within a plant such as maize that are associated with "stay green" or the expression of any gene that delays senescence would be advantageous. For example, a nonyellowing mutant has been identified in *Festuca pratensis* (Davies et al., 1990). Expression of this gene as well as others may prevent premature breakdown of chlorophyll and thus maintain canopy function.

h. Nutrient Utilization

The ability to utilize available nutrients may be a limiting factor in growth of monocotyledonous plants such as maize, barley, wheat, rye or rice. It is proposed that it would be possible to alter nutrient uptake, tolerate pH extremes, mobilization through the plant, storage pools, and availability for metabolic activities by the introduction of novel genes. These modifications would allow a plant such as maize, barley, wheat, rye or rice to more efficiently utilize available nutrients. It is contemplated that an increase in the activity of, for example, an enzyme that is normally present in the plant and involved in nutrient utilization would increase the availability of a nutrient. An example of such an enzyme would be phytase. It further is contemplated that enhanced nitrogen utilization by a plant is desirable. Expression of a glutamate dehydrogenase gene in plants such as maize, e.g., *E. coli* gdhA genes, may lead to increased fixation of nitrogen in organic compounds. Furthermore, expression of gdhA in a plant may lead to enhanced resistance to the herbicide glufosinate by incorporation of excess ammonia into glutamate, thereby detoxifying the ammonia. It also is contemplated that expression of a novel gene may make a nutrient source available that was previously not accessible, e.g., an enzyme that releases a component of nutrient value from a more complex molecule, perhaps a macromolecule.

i. Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani et al., 1990).

A number of mutations were discovered in maize that confer cytoplasmic male sterility. One mutation in particular, referred to as T cytoplasm, also correlates with sensitivity to Southern corn leaf blight. A DNA sequence, designated TURF-13 (Levings, 1990), was identified that correlates with T cytoplasm. It is proposed that it would be possible through the introduction of TURF-13 via transformation, to separate male sterility from disease sensitivity. As it is necessary to be able to restore male fertility for breeding purposes and for grain production, it is proposed that genes encoding restoration of male fertility also may be introduced.

j. Negative Selectable Markers

Introduction of genes encoding traits that can be selected against may be useful for eliminating undesirable linked genes. It is contemplated that when two or more genes are introduced together by cotransformation that the genes will be linked together on the host chromosome. For example, a gene encoding Bt that confers insect resistance to the plant may be introduced into a plant together with a bar gene that is useful as a selectable marker and confers resistance to the herbicide LIBERTY® on the plant. However, it may not be desirable to have an insect resistant plant that also is resistant to the herbicide LIBERTY®. It is proposed that one also could introduce an antisense bar coding region that is expressed in those tissues where one does not want expression of the bar gene product, e.g., in whole plant parts. Hence, although the bar gene is expressed and is useful as a selectable marker, it is not useful to confer herbicide resistance on the whole plant. The bar antisense gene is a negative selectable marker.

It also is contemplated that negative selection is necessary in order to screen a population of transformants for rare homologous recombinants generated through gene targeting. For example, a homologous recombinant may be identified through the inactivation of a gene that was previously expressed in that cell. The antisense construct for neomycin phosphotransferase II (NPT II) has been investigated as a negative selectable marker in tobacco (*Nicotiana tabacum*) and *Arabidopsis thaliana* (Xiang and Guerra, 1993). In this example, both sense and antisense NPT II genes are introduced into a plant through transformation and the resultant plants are sensitive to the antibiotic kanamycin. An introduced gene that integrates into the host cell chromosome at the site of the antisense NPT II gene, and inactivates the antisense gene, will make the plant resistant to kanamycin and other aminoglycoside antibiotics. Therefore, rare, site-specific recombinants may be identified by screening for antibiotic resistance. Similarly, any gene, native to the plant or introduced through transformation, that when inactivated confers resistance to a compound, may be useful as a negative selectable marker.

It is contemplated that negative selectable markers also may be useful in other ways. One application is to construct transgenic lines in which one could select for transposition to unlinked sites. In the process of tagging it is most common for the transposable element to move to a genetically linked site on the same chromosome. A selectable marker for recovery of rare plants in which transposition has occurred to an unlinked locus would be useful. For example, the enzyme cytosine deaminase may be useful for this purpose. In the presence of this enzyme the non-phytotoxic compound 5-fluorocytosine is converted to 5-fluorouracil, which is toxic to plant and animal cells. If a transposable element is linked to the gene for the enzyme cytosine deaminase, one may select for transposition to unlinked sites by selecting for transposition events in which the resultant plant is now resistant to 5-fluorocytosine. The parental plants and plants containing transpositions to linked sites will remain sensitive to 5-fluorocytosine. Resistance to 5-fluorocytosine is due to loss of the cytosine deaminase gene through genetic segregation of the transposable element and the cytosine deaminase gene. Other genes that encode proteins that render the plant sensitive to a certain compound will also be useful in this context. For example, T-DNA gene 2 from *Agrobacterium tumefaciens* encodes a protein that catalyzes the conversion of α-naphthalene acetamide (NAM) to α-naphthalene acetic acid (NAA) which renders plant cells sensitive to high concentrations of NAM (Depicker et al., 1988).

It also is contemplated that negative selectable markers may be useful in the construction of transposon tagging lines. For example, by marking an autonomous transposable element such as Ac, Master Mu, or En/Spn with a negative selectable marker, one could select for transformants in which the autonomous element is not stably integrated into the genome. It is proposed that this would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

It is also contemplated that a negative selectable marker may be useful for identifying rare homologous recombination events between direct repeats. For example, some of the pathways for obtaining a deletion of a transgene (FIG. 1) can occur in hemizygous plant cells, including callus or other regenerative somatic cells during the tissue culture process (Zubko et al, 2000). The recovery of such rare events may be enhanced by screening for the loss (deletion) of a negative selectable marker gene.

k. Non-Protein-Expressing Sequences

DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes. However, as detailed below, DNA need not be expressed to effect the phenotype of a plant.

1. Antisense RNA

Genes may be constructed or isolated, which when transcribed, produce antisense RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction that include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

2. Ribozymes

Genes also may be constructed or isolated, which when transcribed, produce RNA enzymes (ribozymes) that can act as endoribonucleases and catalyze the cleavage of RNA molecules with selected sequences. The cleavage of selected messenger RNAs can result in the reduced production of their encoded polypeptide products. These genes may be used to prepare novel transgenic plants that possess them. The transgenic plants may possess reduced levels of polypeptides including, but not limited to, the polypeptides cited above.

Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence (IGS) of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes.

Several different ribozyme motifs have been described with RNA cleavage activity (Symons, 1992). Examples include sequences from the Group I self-splicing introns including Tobacco Ringspot Virus (Prody et al., 1986), Avocado Sunblotch Viroid (Palukaitis et al., 1979; Symons, 1981), and Lucerne Transient Streak Virus (Forster and Symons, 1987). Sequences from these and related viruses are referred to as hammerhead ribozymes based on a predicted folded secondary structure.

Other suitable ribozymes include sequences from RNase P with RNA cleavage activity (Yuan et al., 1992, Yuan and Altman, 1994, U.S. Pat. Nos. 5,168,053 and 5,624,824), hairpin ribozyme structures (Berzal-Herranz et al., 1992; Chowrira et al., 1993) and Hepatitis Delta virus based ribozymes (U.S. Pat. No. 5,625,047). The general design and optimization of ribozyme directed RNA cleavage activity has been discussed in detail (Haseloff and Gerlach, 1988, Symons, 1992, Chowrira et al., 1994; Thompson et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence that is the cleavage site. For a hammerhead ribozyme, the cleavage site is a dinucleotide sequence on the target RNA, a uracil (U) followed by either an adenine, cytosine or uracil (A, C or U) (Perriman et al., 1992; Thompson et al., 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. The identification of operative and preferred sequences for use in down regulating a given gene is simply a matter of preparing and testing a given sequence, and is a routinely practiced "screening" method known to those of skill in the art.

3. Induction of Gene Silencing

It also is possible that genes may be introduced to produce novel transgenic plants that have reduced expression of a native gene product by the mechanism of co-suppression. It has been demonstrated in tobacco, tomato, petunia, and corn (Goring et al., 1991; Smith et al., 1990; Napoli et al., 1990; van der Krol et al., 1990; PCT Publication No. WO 98/26064) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

4. Non-RNA-Expressing Sequences

DNA elements including those of transposable elements such as Ds, Ac, or Mu, may be inserted into a gene to cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer target sequence together with PCR gene cloning techniques (Shapiro, 1983; Dellaporta et al., 1988). Once identified, the entire gene(s) for the particular trait, including control or regulatory regions where desired, may be isolated, cloned and manipulated as desired. The utility of DNA elements introduced into an organism for purposes of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences, could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Another possible element that may be introduced is a matrix attachment region element (MAR), such as the chicken lysozyme A element (Stief, 1989), which can be positioned around an expressible gene of interest to effect an increase in overall expression of the gene and diminish position dependent effects upon incorporation into the plant genome (Stief et al., 1989; Phi-Van et al., 1990).

5. Other sequences

An expression cassette of the invention can also be further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the expression cassette, and sequences that enhance transformation of prokaryotic and eukaryotic cells.

Another vector that is useful for expression in both plant and prokaryotic cells is the binary Ti plasmid (as disclosed in U.S. Pat. No. 4,940,838) as exemplified by vector pGA582. This binary Ti plasmid vector has been previously characterized by An (1989) and is available from Dr. An. This binary Ti vector can be replicated in prokaryotic bacteria such as E. coli and Agrobacterium. The Agrobacterium plasmid vectors can be used to transfer the expression cassette to plant cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform plant cells.

In certain embodiments, it is contemplated that one may wish to employ replication-competent viral vectors in monocot transformation. Such vectors include, for example, wheat dwarf virus (WDV) "shuttle" vectors, such as pW1–11 and PW1-GUS (Ugaki et al., 1991). These vectors are capable of autonomous replication in cells as well as E. coli, and as such may provide increased sensitivity for detecting DNA delivered to transgenic cells. A replicating vector may also be useful for delivery of genes flanked by DNA sequences from transposable elements such as Ac, Ds, or Mu. It has been proposed (Laufs et al., 1990) that transposition of these elements within the genome requires DNA replication. It is also contemplated that transposable elements would be useful for introducing DNA fragments lacking elements necessary for selection and maintenance of the plasmid vector in bacteria, e.g., antibiotic resistance genes and origins of DNA replication. It is also proposed that use of a transposable element such as Ac, Ds, or Mu would actively promote integration of the desired DNA and hence increase the frequency of stably transformed cells.

Vectors, plasmids, cosmids, YACs (yeast artificial chromosomes) and DNA segments for use in transforming such cells will, of course, generally comprise the isolated and purified cDNA(s), isolated and purified DNA(s) or genes that one desires to introduce into the cells. These DNA constructs can further include structures such as promoters, enhancers, polylinkers, or even regulatory genes as desired.

The DNA segment or gene chosen for cellular introduction will often encode a protein that will be expressed in the resultant recombinant cells, such as will result in a screenable or selectable trait and/or that will impart an improved phenotype to the regenerated plant. However, this may not always be the case, and the present invention also encompasses transgenic plants incorporating non-expressed transgenes.

III. Methods for Plant Transformation

Suitable methods for plant transformation for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), Through the application of techniques such as these, maize cells as well as those of virtually any other plant species may be stably transformed, and these cells developed into transgenic plants. In certain embodiments, acceleration methods are preferred and include, for example, microprojectile bombardment and the like.

A. Electroporation

Where one wishes to introduce DNA by means of electroporation, it is contemplated that the method of Krzyzek et al. (U.S. Pat. No. 5,384,253, incorporated herein by reference in its entirety) will be particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation by mechanical wounding.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species that have been transformed by electroporation of intact cells include (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in PCT Publication No. WO 92/17598 (specifically incorporated herein by reference). Other examples of species for which protoplast transformation has been described include barley (Lazerri, 1995), sorghum (Battraw et al., 1991), (Bhattacharjee et al., 1997), wheat (He et al., 1994) and tomato (Tsukada, 1989).

B. Microprojectile Bombardment

A preferred method for delivering transforming DNA segments to plant cells in accordance with the invention is microprojectile bombardment (U.S. Pat. No. 5,550,318; U.S. Pat. No. 5,538,880; U.S. Pat. No. 5,610,042; and U.S. Pat. No. 5,590,390; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. Examples of species for which have been transformed by microprojectile bombardment include monocot species such as maize (U.S. Pat. No. 5,590,390), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (Van Eck et al. 1995), and legumes in general (U.S. Pat. No. 5,563,055, specifically incorporated herein by reference in its entirety).

C. Agrobacterium-mediated Transformation

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

Agrobacterium-mediated transformation is most efficient in dicotyledonous plants and is the preferable method for transformation of dicots, including Arabidopsis, tobacco, tomato, and potato. Indeed, while Agrobacterium-mediated transformation has been routinely used with dicotyledonous plants for a number of years, it has only recently become applicable to monocotyledonous plants. Advances in Agrobacterium-mediated transformation techniques have now made the technique applicable to nearly all monocotyledonous plants. For example, Agrobacterium-mediated transformation techniques have now been applied to rice (Hiei et al., 1997; Zhang et al., 1997; U.S. Pat. No. 5,591,616, specifically incorporated herein by reference in its entirety), wheat (McCormac et al., 1998), barley (Tingay et al., 1997; McCormac et al., 1998), and rice (Ishida et al., 1996).

Modern Agrobacterium transformation vectors are capable of replication in E. coli as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cell is punctured. This technique has been used successfully with, for example, the monocot cereals (U.S. Pat. No. 5,590,390, specifically incorporated herein by reference in its entirety; Thompson, 1995) and rice (Nagatani, 1997).

IV. Optimization of Microprojectile Bombardment

For microprojectile bombardment transformation in accordance with the current invention, both physical and biological parameters may be optimized. Physical factors are those that involve manipulating the DNA/microprojectile precipitate or those that affect the flight and velocity of either the macro- or microprojectiles. Biological factors include all steps involved in manipulation of cells before and immediately after bombardment, such as the osmotic adjustment of target cells to help alleviate the trauma associated with bombardment, the orientation of an immature embryo or other target tissue relative to the particle trajectory, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as DNA concentration, gap distance, flight distance, tissue distance, and helium pressure. It further is contemplated that the grade of helium may affect transformation efficiency. For example, differences in transformation efficiencies may be witnessed between bombardments using industrial grade (99.99% pure) or ultra pure helium (99.999% pure), although it is not currently clear that is more advantageous for use in bombardment. One also may optimize the trauma reduction factors (TRFs) by modifying conditions that influence the physiological state of the recipient cells and that may therefore influence transformation and integration efficiencies. For example, the osmotic state, tissue hydration and the subculture stage or cell cycle of the recipient cells may be adjusted for optimum transformation.

A. Physical Parameters

1. Gap Distance

The variable nest (macro holder) can be adjusted to vary the distance between the rupture disk and the macroprojectile, i.e., the gap distance. This distance can be varied from 0 to 2 cm. The predicted effects of a shorter gap are an increase of velocity of both the macro- and microprojectiles, an increased shock wave (which leads to tissue splattering and increased tissue trauma), and deeper penetration of microprojectiles. Longer gap distances would have the opposite effects but may increase viability and therefore the total number of recovered stable transformants.

2. Flight Distance

The fixed nest (contained within the variable nest) can be varied between 0.5 and 2.25 cm in predetermined 0.5 cm increments by the placement of spacer rings to adjust the flight path traversed by the macroprojectile. Short flight paths allow for greater stability of the macroprojectile in flight but reduce the overall velocity of the microprojectiles. Increased stability in flight increases, for example, the number of centered GUS foci. Greater flight distances (up to a point) increase velocity but also increase instability in flight. Based on observations, it is recommended that bombardments typically be done with a flight path length of about 1.0 cm to 1.5 cm.

3. Tissue Distance

Placement of tissue within the gun chamber can have significant effects on microprojectile penetration. Increasing the flight path of the microprojectiles will decrease velocity and trauma associated with the shock wave. A decrease in velocity also will result in shallower penetration of the microprojectiles.

4. Helium Pressure

By manipulation of the type and number of rupture disks, pressure can be varied between 400 and 2000 psi within the gas acceleration tube. Optimum pressure for stable transformation has been determined to be between 1000 and 1200 psi.

5. Coating of Microprojectiles.

For microprojectile bombardment, one will attach (i.e., "coat") DNA to the microprojectiles such that it is delivered to recipient cells in a form suitable for transformation thereof. In this respect, at least some of the transforming DNA must be available to the target cell for transformation to occur, while at the same time during delivery the DNA must be attached to the microprojectile. Therefore, availability of the transforming DNA from the microprojectile may comprise the physical reversal of bonds between transforming DNA and the microprojectile following delivery of the microprojectile to the target cell. This need not be the case, however, as availability to a target cell may occur as a result of breakage of unbound segments of DNA or of other molecules that comprise the physical attachment to the microprojectile. Availability may further occur as a result of breakage of bonds between the transforming DNA and other molecules, which are either directly or indirectly attached to the microprojectile. It further is contemplated that transformation of a target cell may occur by way of direct recombination between the transforming DNA and the genomic DNA of the recipient cell. Therefore, as used herein, a "coated" microprojectile will be one that is capable of being used to transform a target cell, in that the transforming DNA will be delivered to the target cell, yet will be accessible to the target cell such that transformation may occur.

Any technique for coating microprojectiles that allows for delivery of transforming DNA to the target cells may be used. Methods for coating microprojectiles that have been demonstrated to work well with the current invention have been specifically disclosed herein. DNA may be bound to microprojectile particles using alternative techniques, however. For example, particles may be coated with streptavidin and DNA end labeled with long chain thiol-cleavable biotinylated nucleotide chains. The DNA adheres to the particles due to the streptavidin-biotin interaction, but is released in the cell by reduction of the thiol linkage through reducing agents present in the cell.

Alternatively, particles may be prepared by functionalizing the surface of a gold oxide particle, providing free amine groups. DNA, having a strong negative charge, binds to the functionalized particles. Furthermore, charged particles may be deposited in controlled arrays on the surface of mylar flyer disks used in the PDS-1000 Biolistics device, thereby facilitating controlled distribution of particles delivered to target tissue.

As disclosed above, it further is proposed that the concentration of DNA used to coat microprojectiles may influence the recovery of transformants containing a single copy of the transgene. For example, a lower concentration of DNA may not necessarily change the efficiency of the transformation, but may instead increase the proportion of single copy insertion events. In this regard, approximately 1 ng to 2000 ng of transforming DNA may be used per each 1.8 mg of starting microprojectiles. In other embodiments of the invention, approximately 2.5 ng to 1000 ng, 2.5 ng to 750 ng, 2.5 ng to 500 ng, 2.5 ng to 250 ng, 2.5 ng to 100 ng, or 2.5 ng to 50 ng of transforming DNA may be used per each 1.8 mg of starting microprojectiles.

Various other methods also may be used to increase transformation efficiency and/or increase the relative proportion of low-copy transformation events. For example, the inventors contemplate end-modifying transforming DNA with alkaline phosphatase or an agent that will blunt DNA ends prior to transformation. Still further, an inert carrier DNA may be included with the transforming DNA, thereby lowering the effective transforming DNA concentration without lowering the overall amount of DNA used. These techniques are further described in U.S. patent application Ser. No. 08/995,451, filed Dec. 22, 1997, the disclosure of which is specifically incorporated herein by reference in its entirety.

B. Biological Parameters

Culturing conditions and other factors can influence the physiological state of the target cells and may have profound effects on transformation and integration efficiencies. First, the act of bombardment could stimulate the production of ethylene, which could lead to senescence of the tissue. The addition of antiethylene compounds could increase transformation efficiencies. Second, it is proposed that certain points in the cell cycle may be more appropriate for integration of introduced DNA. Hence synchronization of cell cultures may enhance the frequency of production of transformants. For example, synchronization may be achieved using cold treatment, amino acid starvation, or other cell cycle-arresting agents. Third, the degree of tissue hydration also may contribute to the amount of trauma associated with bombardment as well as the ability of the microprojectiles to penetrate cell walls.

The position and orientation of an embryo or other target tissue relative to the particle trajectory also may be important. For example, the PDS-1000 Biolistics device does not produce a uniform spread of particles over the surface of a target petri dish. The velocity of particles in the center of the plate is higher than the particle velocity at further distances from the center of the petri dish. Therefore, it is advantageous to situate target tissue on the petri dish such as to avoid the center of the dish, referred to by some as the "zone of death." Furthermore, orientation of the target tissue with regard to the trajectory of targets also can be important. It is contemplated that it is desirable to orient the tissue most likely to regenerate a plant toward the particle stream. For example, the scutellum of an immature embryo comprises the cells of greatest embryogenic potential and therefore should be oriented toward the particle stream.

It also has been reported that slightly plasmolyzed yeast cells allow increased transformation efficiencies (Armaleo et al., 1990). It was hypothesized that the altered osmotic state of the cells helped to reduce trauma associated with the penetration of the microprojectile. Additionally, the growth and cell cycle stage may be important with respect to transformation.

1. Osmotic Adjustment

It has been suggested that osmotic pre-treatment could potentially reduce bombardment associated injury as a result of the decreased turgor pressure of the plasmolyzed cell. In a previous study, the number of cells transiently expressing GUS increased following subculture into both fresh medium and osmotically adjusted medium (U.S. Pat. No. 5,590,390, specifically incorporated herein by reference in its entirety). Pretreatment times of 90 minutes showed higher numbers of GUS expressing foci than shorter times. Cells incubated in 500 mOSM/kg medium for 90 minutes showed an approximately 3.5 fold increase in transient GUS foci than the control. Preferably, immature embryos are precultured for 4–5 hours prior to bombardment on culture medium containing 12% sucrose. A second culture on 12% sucrose is performed for 16–24 hours following bombardment.

Alternatively, type II cells are pretreated on 0.2M mannitol for 3–4 hours prior to bombardment. It is contemplated that pretreatment of cells with other osmotically active solutes for a period of 1–6 hours also may be desirable.

2. Plasmid Configuration

In some instances, it will be desirable to deliver DNA to cells that does not contain DNA sequences necessary for maintenance of the plasmid vector in the bacterial host, e.g., *E. coli*, such as antibiotic resistance genes, including but not limited to ampicillin, kanamycin, and tetracycline resistance, and prokaryotic origins of DNA replication. In such case, a DNA fragment containing the transforming DNA may be purified prior to transformation. An exemplary method of purification is gel electrophoresis on a 1.2% low melting temperature agarose gel, followed by recovery from the agarose gel by melting gel slices in a 6–10 fold excess of Tris-EDTA buffer (10 mM Tris-HCl pH 8.0, 1 mM EDTA, 70° C.–72° C.); frozen and thawed (37° C.); and the agarose pelleted by centrifugation. A Qiagen Q-100 column then may be used for purification of DNA. For efficient recovery of DNA, the flow rate of the column may be adjusted to 40 ml/hr.

Isolated DNA fragments can be recovered from agarose gels using a variety of electroelution techniques, enzyme digestion of the agarose, or binding of DNA to glass beads (e.g., Gene Clean). In addition, HPLC and/or use of magnetic particles may be used to isolate DNA fragments. As an alternative to isolation of DNA fragments, a plasmid vector can be digested with a restriction enzyme and this DNA delivered to cells without prior purification of the expression cassette fragment.

V. Recipient Cells for Transformation

Tissue culture requires media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid. Table 8 illustrates the composition of various media useful for creation of recipient cells and for plant regeneration.

Recipient cell targets include, but are not limited to, meristem cells, Type I, Type II, and Type III callus, immature embryos and gametic cells such as microspores, pollen, sperm and egg cells. It is contemplated that any cell from which a fertile plant may be regenerated is useful as a recipient cell. Type I, Type II, and Type III callus may be initiated from tissue sources including, but not limited to, immature embryos, immature inflorescenses, seedling apical meristems, microspores and the like. Those cells that are capable of proliferating as callus also are recipient cells for genetic transformation. The present invention provides techniques for transforming immature embryos and subsequent regeneration of fertile transgenic plants. Transformation of immature embryos obviates the need for long term development of recipient cell cultures. Pollen, as well as its precursor cells, microspores, may be capable of functioning as recipient cells for genetic transformation, or as vectors to carry foreign DNA for incorporation during fertilization. Direct pollen transformation would obviate the need for cell culture. Meristematic cells (i.e., plant cells capable of continual cell division and characterized by an undifferentiated cytological appearance, normally found at growing points or tissues in plants such as root tips, stem apices, lateral buds, etc.) may represent another type of recipient plant cell. Because of their undifferentiated growth and capacity for organ differentiation and totipotency, a single transformed meristematic cell could be recovered as a whole transformed plant. In fact, it is proposed that embryogenic suspension cultures may be an in vitro meristematic cell system, retaining an ability for continued cell division in an undifferentiated state, controlled by the media environment.

Cultured plant cells that can serve as recipient cells for transforming with desired DNA segments may be any plant cells including maize cells, and more specifically, cells from *Zea mays* L. Somatic cells are of various types. Embryogenic cells are one example of somatic cells that may be induced to regenerate a plant through embryo formation. Non-embryogenic cells are those that typically will not respond in such a fashion. An example of non-embryogenic cells are certain Black Mexican Sweet (BMS) corn cells.

The development of embryogenic calli and suspension cultures useful in the context of the present invention, e.g., as recipient cells for transformation, has been described in U.S. Pat. No. 5,134,074; U.S. Pat. No. 5,489,520 and U.S. Pat. No. 5,990,390; each of which is incorporated herein by reference in its entirety.

Certain techniques may be used that enrich recipient cells within a cell population. For example, Type II callus development, followed by manual selection and culture of friable, embryogenic tissue, generally results in an enrichment of recipient cells for use in microprojectile transformation. Suspension culturing, particularly using the media disclosed herein, may improve the ratio of recipient to non-recipient cells in any given population. Manual selection techniques that can be employed to select recipient cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for recipient cells prior to culturing (whether cultured on solid media or in suspension). The preferred cells may be those located at the surface of a cell cluster, and may further be identifiable by their lack of differentiation, their size and dense cytoplasm. The preferred cells will generally be those cells that are less differentiated, or not yet committed to differentiation. Thus, one may wish to identify and select those cells that are cytoplasmically dense, relatively unvacuolated with a high nucleus to cytoplasm ratio (e.g., determined by cytological observations), small in size (e.g., 10–20 μm), and capable of sustained divisions and somatic proembryo formation.

It is proposed that other means for identifying such cells also may be employed. For example, through the use of dyes, such as Evan's blue, which are excluded by cells with relatively non-permeable membranes, such as embryogenic cells, and taken up by relatively differentiated cells such as root-like cells and snake cells (so-called due to their snake-like appearance).

Other possible means of identifying recipient cells include the use of isozyme markers of embryogenic cells, such as glutamate dehydrogenase, which can be detected by cytochemical stains (Fransz et al., 1989). However, it is cautioned that the use of isozyme markers including glutamate dehydrogenase may lead to some degree of false positives from non-embryogenic cells such as rooty cells that nonetheless have a relatively high metabolic activity.

A. Culturing Cells to be Recipients for Transformation

The ability to prepare and cryopreserve cultures of plant cells is important to certain aspects of the present invention, in that it provides a means for reproducibly and successfully preparing cells for transformation. A variety of different types of media have been previously developed and may be employed in carrying out various aspects of the invention. The following table, Table 8, sets forth the composition of the media preferred by the inventor for carrying out these aspects of the invention.

TABLE 8

Tissue Culture Media Used for Type II Callus Development, Development of Suspension Cultures and Regeneration of Plant Cells (Particularly Cells)

| MEDIA NO. | BASAL MEDIUM | SUCROSE | pH | OTHER COMPONENTS** (Amount/L) |
|---|---|---|---|---|
| 7 | MS* | 2% | 6.0 | .25 mg thiamine<br>.5 mg BAP<br>.5 mg NAA<br>Bactoagar |
| 10 | MS | 2% | 6.0 | .25 mg thiamine<br>1 mg BAP<br>1 mg 2,4-D<br>400 mg L-proline<br>Bactoagar |
| 19 | MS | 2% | 6.0 | .25 mg thiamine<br>.25 mg BAP<br>.25 mg NAA<br>Bactoagar |
| 20 | MS | 3% | 6.0 | .25 mg thiamine<br>1 mg BAP<br>1 mg NAA<br>Bactoagar |
| 52 | MS | 2% | 6.0 | .25 mg thiamine<br>1 mg 2,4-D<br>$10^{-7}$ M ABA<br>BACTOAGAR |
| 101 | MS | 3% | 6.0 | MS vitamins<br>100 mg myo-inositol<br>Bactoagar |
| 105 | MS | — | 3.5 | 0.04 mg NAA<br>3 mg BAP<br>1 mg thiamine.HCl<br>0.5 mg niacin<br>0.91 mg L-asparagine monohydrate<br>100 mg myo-inositol<br>100 mg casein hydrolysate<br>1.4 g L-proline<br>20 g sorbitol<br>2.0 g Gelgro |
| 110 | MS | 6% | 5.8 | 1 mg thiamine.HCl<br>1 mg niacin<br>3.6 g Gelgro |
| 142 | MS | 6% | 6.0 | MS vitamins<br>5 mg BAP<br>0.186 mg NAA<br>0.175 mg IAA<br>0.403 mg 2IP<br>Bactoagar |
| 157 | MS | 6% | 6.0 | MS vitamins<br>100 mg myo-inositol<br>Bactoagar |
| 163 | MS | 3% | 6.0 | MS vitamins<br>3.3 mg dicamba<br>100 mg myo-inositol<br>Bactoagar |
| 171 | MS | 3% | 6.0 | MS vitamins<br>.25 mg 2,4-D<br>10 mg BAP<br>100 mg myo-inositol<br>Bactoagar |
| 173 | MS | 6% | 6.0 | MS vitamins<br>5 mg BAP<br>.186 mg NAA<br>.175 mg IAA<br>.403 mg 2IP<br>$10^{-7}$ M ABA<br>200 mg myo-inositol<br>Bactoagar |
| 177 | MS | 3% | 6.0 | MS vitamins<br>.25 mg 2,4-D<br>10 mg BAP<br>$10^{-7}$ M ABA<br>100 mg myo-inositol<br>Bactoagar |
| 185 | MS | — | 5.8 | 3 mg BAP<br>.04 mg NAA<br>RT vitamins<br>1.65 mg thiamine<br>1.38 g L-proline<br>20 g sorbitol<br>Bactoagar |
| 189 | MS | — | 5.8 | 3 mg BAP<br>.04 mg NAA<br>.5 mg niacin<br>800 mg L-asparagine<br>100 mg casamino acids<br>20 g sorbitol<br>1.4 g L-proline<br>100 mg myo-inositol<br>Gelgro |
| 201 | N6 | 2% | 5.8 | N6 vitamins<br>2 mg L-glycine<br>1 mg 2,4-D<br>100 mg casein hydrolysate<br>2.9 g L-proline<br>Gelgro |
| 205 | N6 | 2% | 5.8 | N6 vitamins<br>2 mg L-glycine<br>.5 mg 2,4-D<br>100 mg casein hydrolysate<br>2.9 g L-proline<br>Gelgro |
| 209 | N6 | 6% | 5.8 | N6 vitamins<br>2 mg L-glycine<br>100 mg casein hydrolysate<br>0.69 g L-proline<br>Bactoagar |
| 210 | N6 | 3% | 5.5 | N6 vitamins<br>2 mg 2,4-D<br>250 mg Ca |

TABLE 8-continued

Tissue Culture Media Used for Type II Callus Development, Development of Suspension Cultures and Regeneration of Plant Cells (Particularly Cells)

| MEDIA NO. | BASAL MEDIUM | SUCROSE | pH | OTHER COMPONENTS** (Amount/L) |
|---|---|---|---|---|
| 211 | N6 | 2% | 5.8 | pantothenate<br>100 mg myo-inositol<br>790 mg L-asparagine<br>100 mg casein hydrolysate<br>1.4 g L-proline<br>Hazelton agar****<br>2 mg L-glycine<br>1 mg 2,4-D<br>0.5 mg niacin<br>1.0 mg thiamine<br>0.91 g L-asparagine<br>100 mg myo-inositol<br>0.5 g MES<br>100 mg/L casein hydrolysate<br>1.6 g MgCl$_2$—6H$_2$O<br>0.69 g L-proline<br>2 g Gelgro |
| 212 | N6 | 3% | 5.5 | N6 vitamins<br>2 mg L-glycine<br>2 mg 2,4-D<br>250 mg Ca pantothenate<br>100 mg myo-inositol<br>100 mg casein hydrolysate<br>1.4 g L-proline<br>Hazelton agar**** |
| 227 | N6 | 2% | 5.8 | N6 vitamins<br>2 mg L-glycine<br>13.2 mg dicamba<br>100 mg casein hydrolysate<br>2.9 g L-proline<br>Gelgro |
| 273 (also, 201V, 236S, 201D, 2071, 2366,201SV, 2377, and 201BV) | N6 | 2% | 5.8 | N6 vitamins<br>2 mg L-glycine<br>1 mg 2,4-D<br>16.9 mg AgNO$_3$<br>100 mg casein hydrolysate<br>2.9 g L-proline |
| 279 | N6 | 2% | 5.8 | 3.3 mg dicamba<br>1 mg thiamine<br>.5 mg niacin<br>800 mg L-asparagine<br>100 mg casein hydrolysate<br>100 mg myoinositol<br>1.4 g L-proline<br>Gelgro**** |
| 288 | N6 | 3% | | 3.3 mg dicamba<br>1 mg thiamine<br>.5 mg niacin<br>.8 g L-asparagine<br>100 mg myo-inosital<br>1.4 g L-proline<br>100 mg casein hydrolysate<br>16.9 mg AgNO$_3$<br>Gelgro |
| 401 | MS | 3% | 6.0 | 3.73 mg Na$_2$EDTA<br>.25 mg thiamine<br>1 mg 2,4-D<br>2 mg NAA<br>200 mg casein hydrolysate<br>500 mg K$_2$SO$_4$<br>400 mg KH$_2$PO$_4$<br>100 mg myo-inositol |
| 402 | MS | 3% | 6.0 | 3.73 mg Na$_2$EDTA<br>.25 mg thiamine<br>1 mg 2,4-D<br>200 mg casein hydrolysate<br>2.9 g L-proline<br>500 mg K$_2$SO$_4$<br>400 mg KH$_2$PO$_4$<br>100 mg myo-inositol |
| 409 | MS | 3% | 6.0 | 3.73 mg Na$_2$EDTA<br>.25 mg thiamine<br>9.9 mg dicamba<br>200 mg casein hydrolysate<br>2.9 g L-proline<br>500 mg K$_2$SO$_4$<br>400 mg KH$_2$PO$_4$<br>100 mg myo-inositol |
| 501 | Clark's Medium** | 2% | 5.7 | |
| 607 | ½ × MS | 3% | 5.8 | 1 mg thiamine<br>1 mg niacin<br>Gelrite |
| 615 | MS | 3% | 6.0 | MS vitamins<br>6 mg BAP<br>100 mg myo-mositol<br>Bactoagar |
| 617 | ½ × MS | 1.5% | 6.0 | MS vitamins<br>50 mg myo-inositol<br>Bactoagar |
| 708 | N6 | 2% | 5.8 | N6 vitamins<br>2 mg L-glycine<br>1.5 mg 2,4-D<br>200 mg casein hydrolysate<br>0.69 g L-proline<br>Gelrite |
| 721 | N6 | 2% | 5.8 | 3.3 mg dicamba<br>1 mg thiamine<br>.5 mg niacin<br>800 mg L-asparagine<br>100 mg myo-inositol<br>100 mg casein hydrolysate<br>1.4 g L-proline<br>54.65 g mannitol<br>Gelgro |
| 726 | N6 | 3% | 5.8 | 3.3 mg dicamba<br>.5 mg niacin<br>1 mg thiamine<br>800 mg L-asparagine<br>100 mg myo-inositol<br>100 mg casein hydrolysate<br>1.4 g L-proline |
| 727 | N6 | 3% | 5.8 | N6 vitamins<br>2 mg L-glycine<br>9.9 mg dicamba<br>100 mg casein hydrolysate<br>2.9 g L-proline<br>Gelgro |
| 728 | N6 | 3% | 5.8 | N6 vitamins<br>2 mg L-glycine<br>9.9 mg dicamba<br>16.9 mg AgNO$_3$<br>100 mg casein hydrolysate<br>2.9 g L-proline<br>Gelgro |

| MEDIA NO. | BASAL MEDIUM | SUCROSE | pH | OTHER COMPONENTS** (Amount/L) |
|---|---|---|---|---|
| 734 | N6 | 2% | 5.8 | N6 vitamins<br>2 mg L-glycine<br>1.5 mg 2,4-D<br>14 g Fe sequestreene (replaces Fe-EDTA)<br>200 mg casein hydrolyste<br>0.69 g L-proline<br>Gelrite |
| 735 | N6 | 2% | 5.8 | 1 mg 2,4-D<br>.5 mg niacin<br>.91 g L-asparagine<br>100 mg myo-inositol<br>1 mg thiamine<br>.5 g MES<br>.75 g $MgCl_2$<br>100 mg casein hydrolysate<br>0.69 g L-proline<br>Gelgro |
| 2004 | N6 | 3% | 5.8 | 1 mg thiamine<br>0.5 mg macin<br>3.3 mg dicamba<br>17 mg $AgNO_3$<br>1.4 g L-proline<br>0.8 g L-asparagine<br>100 mg casein hydrolysate<br>100 mg myo-inositol<br>Gelrite |
| 2008 | N6 | 3% | 5.8 | 1 mg thiamine<br>0.5 mg niacin<br>3.3 mg dicamba<br>1.4 g L-proline<br>0.8 g L-asparagine<br>Gelrite |

*Basic MS medium described in Murashige and Skoog (1962). This medium is typically modified by decreasing the $NH_4NO_3$ from 1.64 g/l to 1.55 g/l, and omitting the pyridoxine HCl, nicotinic acid, myo-inositol and glycine.
**NAA = Napthol Acetic Acid
IAA = Indole Acetic Acid
2-IP = 2, isopentyl adenine
2,4-D = 2,4-Dichlorophenoxyacetic Acid
BAY = 6-Benzyl aminopurine
ABA = abscisic acid
***Basic medium described in Clark (1982)
****These media may be made with or without solidifying agent.

A number of exemplary cultures that may be used for transformation have been developed and are disclosed in U.S. Pat. No. 5,590,390, the disclosure of which is specifically incorporated herein by reference.

B. Media

In certain embodiments of the current invention, recipient cells may be selected following growth in culture. Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components (see Table 8), but may differ in the composition and proportions of their ingredients depending on the particular application envisioned. For example, various cell types usually grow in more than one type of media, but will exhibit different growth rates and different morphologies, depending on the growth media. In some media, cells survive but do not divide.

Various types of media suitable for culture of plant cells previously have been described. Examples of these media include, but are not limited to, the N6 medium described by Chu et al. (1975) and MS media (Murashige and Skoog, 1962). It has been discovered that media such as MS that have a high ammonia/nitrate ratio are counterproductive to the generation of recipient cells in that they promote loss of morphogenic capacity. N6 media, on the other hand, has a somewhat lower ammonia/nitrate ratio, and is contemplated to promote the generation of recipient cells by maintaining cells in a proembryonic state capable of sustained divisions.

C. Maintenance

The method of maintenance of cell cultures may contribute to their utility as sources of recipient cells for transformation. Manual selection of cells for transfer to fresh culture medium, frequency of transfer to fresh culture medium, composition of culture medium, and environmental factors including, but not limited to, light quality and quantity and temperature are all important factors in maintaining callus and/or suspension cultures that are useful as sources of recipient cells. It is contemplated that alternating callus between different culture conditions may be beneficial in enriching for recipient cells within a culture. For example, it is proposed that cells may be cultured in suspension culture, but transferred to solid medium at regular intervals. After a period of growth on solid medium cells can be manually selected for return to liquid culture medium. It is proposed that by repeating this sequence of transfers to fresh culture medium it is possible to enrich for recipient cells. It also is contemplated that passing cell cultures through a 1.9 mm sieve is useful in maintaining the friability of a callus or suspension culture and may be beneficial in enriching for transformable cells.

D. Cryopreservation Methods

Cryopreservation is important because it allows one to maintain and preserve a known transformable cell culture for future use, while eliminating the cumulative detrimental effects associated with extended culture periods.

Cell suspensions and callus were cryopreserved using modifications of methods previously reported (Finkle, 1985; Withers & King, 1979). The cryopreservation protocol comprised adding a pre-cooled (0° C.) concentrated cryoprotectant mixture stepwise over a period of one to two hours to pre-cooled (0° C.) cells. The mixture was maintained at 0° C. throughout this period. The volume of added cryoprotectant was equal to the initial volume of the cell suspension (1:1 addition), and the final concentration of cryoprotectant additives was 10% dimethyl sulfoxide, 10% polyethylene glycol (6000 MW), 0.23 M proline and 0.23 M glucose. The mixture was allowed to equilibrate at 0° C. for 30 minutes, during which time the cell suspension/cryoprotectant mixture was divided into 1.5 ml aliquot (0.5 ml packed cell volume) in 2 ml polyethylene cryo-vials. The tubes were cooled at 0.5° C./minute to −8° C. and held at this temperature for ice nucleation.

Once extracellular ice formation had been visually confirmed, the tubes were cooled at 0.5° C./minute from −8° C. to −35° C. They were held at this temperature for 45 minutes (to insure uniform freeze-induced dehydration throughout the cell clusters). At this point, the cells had lost the majority of their osmotic volume (i.e., there is little free water left in the cells), and they could be safely plunged into liquid nitrogen for storage. The paucity of free water remaining in the cells in conjunction with the rapid cooling rates from −35° C. to −196° C. prevented large organized ice crystals from forming in the cells. The cells are stored in liquid nitrogen, which effectively immobilizes the cells and slows metabolic processes to the point where long-term storage should not be detrimental.

Thawing of the extracellular solution was accomplished by removing the cryo-tube from liquid nitrogen and swirling it in sterile 42° C. water for approximately 2 minutes. The tube was removed from the heat immediately after the last ice crystals had melted to prevent heating the tissue. The cell suspension (still in the cryoprotectant mixture) was pipetted onto a filter, resting on a layer of BMS cells (the feeder layer that provided a nurse effect during recovery). The cryoprotectant solution is removed by pipetting. Culture medium comprised a callus proliferation medium with increased osmotic strength. Dilution of the cryoprotectant occurred slowly as the solutes diffused away through the filter and nutrients diffused upward to the recovering cells. Once subsequent growth of the thawed cells was noted, the growing tissue was transferred to fresh culture medium. If initiation of a suspension culture was desired, the cell clusters were transferred back into liquid suspension medium as soon as sufficient cell mass had been regained (usually within 1 to 2 weeks). Alternatively, cells were cultured on solid callus proliferation medium. After the culture was reestablished in liquid (within 1 to 2 additional weeks), it was used for transformation experiments. When desired, previously cryopreserved cultures may be frozen again for storage.

VI. Production and Characterization of Stably Transformed Plants

After effecting delivery of exogenous DNA to recipient cells, the next steps generally concern identifying the transformed cells for further culturing and plant regeneration. As mentioned herein, in order to improve the ability to identify transformants, one may desire to employ a selectable or screenable marker gene as, or in addition to, the expressible gene of interest. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene that confers resistance to some normally inhibitory agent, such as an antibiotic or herbicide. Examples of antibiotics that may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA. Using the techniques disclosed herein, greater than 40% of bombarded embryos may yield transformants.

One herbicide that constitutes a desirable selection agent is the broad spectrum herbicide bialaphos. Bialaphos is a tripeptide antibiotic produced by Streptomyces hygroscopicus and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide LIBERTY® also is effective as a selection agent. Inhibition of GS in plants by PPT causes the rapid accumulation of ammonia and death of the plant cells.

The organism producing bialaphos and other species of the genus Streptomyces also synthesizes an enzyme phosphinothricin acetyl transferase (PAT) that is encoded by the bar gene in *Streptomyces hygroscopicus* and the pat gene in *Streptomyces viridochromogenes*. The use of the herbicide resistance gene encoding phosphinothricin acetyl transferase (PAT) is referred to in U.S. Pat. No. 5,276,268, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) Brassica (De Block et al., 1989) and maize (U.S. Pat. No. 5,550,318). In previous reports, some transgenic plants that expressed the resistance gene were completely resistant to commercial formulations of PPT and bialaphos in greenhouses.

Another example of a herbicide that is useful for selection of transformed cell lines in the practice of the invention is the broad spectrum herbicide glyphosate. Glyphosate inhibits the action of the enzyme EPSPS, which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations that confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, PCT Publication No. WO 97/04103. The best characterized mutant EPSPS gene conferring glyphosate resistance comprises amino acid changes at residues 102 and 106, although it is anticipated that other mutations will also be useful (PCT Publication No. WO97/04103). Furthermore, a naturally occurring glyphosate resistant EPSPS may be used, e.g., the CP4 gene isolated from Agrobacterium encodes a glyphosate resistant EPSPS (U.S. Pat. No. 5,627,061).

To use the nptII-paromomycin selective system, bombarded tissue is cultured for 0–28 days, preferably 0–10 days, most preferably less than 1 day on culture medium lacking paromomycin. Bombarded tissue is transferred to culture medium comprising 25–500 mg/L paromomycin and subculture at 1 to 3 week intervals onto fresh selective medium for 3–15 weeks. Transformants are visually identified as healthy growing callus.

To use the bar-bialaphos or the EPSPS-glyphosate selective system, bombarded tissue is cultured for 0–28 days on nonselective medium and subsequently transferred to medium containing from 1–3 mg/l bialaphos or 1–3 mM glyphosate as appropriate. While ranges of 1–3 mg/l bialaphos or 1–3 mM glyphosate will typically be preferred, it is proposed that ranges of 0.1–50 mg/l bialaphos or 0.1–50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

Although general methods of use of nptII, bar and EPSPS as selectable marker genes are described above, following DNA delivery by microprojectile bombment it is recognized that the described selection methods will work following DNA delivery by any method, including but not limited to, microprojectile bombardment, Agrobacterium mediated transformation, and other methods of DNA delivery to plant cells are known in the art.

It further is contemplated that the herbicide dalapon, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992; U.S. Pat. No. 5,780,708).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468 and PCT Publication No. WO 97/26366.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase may be used as a screenable marker in the context of the present invention. In the presence of the substrate luciferin, cells expressing luciferase emit light that can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells that are expressing luciferase and manipulate those in real time. Another screenable marker that may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and non-transforrnants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified (see Table 8) by including further substances such as growth regulators. A preferred growth regulator for such purposes is dicamba or 2,4-D. However, other growth regulators may be employed, including NAA, NAA+2,4-D or perhaps even picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soiless plant growth mix, and hardened off, e.g., in an environmentally controlled chamber at about 85% relative humidity, 600 ppm $CO_2$, and 25–250 microeinsteins $m^{-2}$ $s^{-1}$ of light, prior to transfer to a greenhouse or growth chamber for maturation. Plants are preferably matured either in a growth chamber or greenhouse. Plants are regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants are preferably grown at about 19 to 28° C. After the regenerating plants have reached the stage of shoot and root development, they may be transferred to a greenhouse for further growth and testing.

Note, however, that seeds on transformed plants may occasionally require embryo rescue due to cessation of seed development and premature senescence of plants. To rescue developing embryos, they are excised from surface-disinfected seeds 10–20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}M$ abscisic acid and then transferred to growth regulator-free medium for germination.

Progeny may be recovered from transformed plants and tested for expression of the exogenous expressible gene by localized application of an appropriate substrate to plant parts such as leaves. In the case of bar transformed plants, it was found that transformed parental plants ($R_O$) and their progeny of any generation tested exhibited no bialaphos-related necrosis after localized application of the herbicide Basta to leaves, if there was functional PAT activity in the plants as assessed by an in vitro enzymatic assay. All PAT positive progeny tested contained bar, confirming that the presence of the enzyme and the resistance to bialaphos were associated with the transmission through the germline of the marker gene.

C. Characterization

To confirm the presence of the isolated and purified DNA segment(s) or "transgene(s)" in the regenerating plants, a variety of assays may be performed. Such assays include, for example, "molecular biological" assays well known to those of skill in the art, such as Southern and Northern blotting, RT-PCR and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced isolated and purified DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the isolated and purified DNA segment in question, they do not provide information as to whether the isolated and purified DNA segment is being expressed. Expression may be evaluated by specifically identifying the protein products of the introduced isolated and purified DNA sequences or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focussing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of isolated and purified DNA segments encoding storage proteins that change amino acid composition and may be detected by amino acid analysis.

1. DNA Integration, RNA Expression and Inheritance

Genomic DNA may be isolated from callus cell lines or any plant parts to determine the presence of the isolated and purified DNA segment through the use of techniques well known to those skilled in the art. Note that intact sequences will not always be present, presumably due to rearrangement or deletion of sequences in the cell.

The presence of DNA elements introduced through the methods of this invention may be determined by polymerase chain reaction (PCR). Using this technique discreet fragments of DNA are amplified and detected by gel electrophoresis or other methods known to the art. This type of analysis permits one to determine whether an isolated and purified DNA segment is present in a stable transformant, but does not prove integration of the introduced isolated and purified DNA segment into the host cell genome. It is contemplated that using PCR techniques it would be possible to clone fragments of the host genomic DNA adjacent to an introduced isolated and purified DNA segment.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced isolated and purified DNA segments in high molecular weight DNA, i.e., confirm that the introduced isolated and purified DNA segment has been integrated into the host cell genome. The technique of Southern hybridization provides information that is obtained using PCR, e.g., the presence of an isolated and purified DNA segment, but also demonstrates integration into the genome and characterizes each individual transformant.

It is contemplated that using the techniques of dot or slot blot hybridization that are modifications of Southern hybridization techniques one could obtain the same information that is derived from PCR, e.g., the presence of an isolated and purified DNA segment. However, it is well known in the art that dot or slot blot hybridization may produce misleading results, as probe may be non-specifically bound by high molecular weight DNA.

Both PCR and Southern hybridization techniques can be used to demonstrate transmission of an isolated and purified DNA segment to progeny. In most instances the characteristic Southern hybridization pattern for a given transformant will segregate in progeny as one or more Mendelian genes (Spencer et al., 1992; Laursen et al., 1994) indicating stable inheritance of the gene. For example, in one study, of 28 progeny ($R_1$) plants tested, 50% (N=14) contained bar, confirming transmission through the germline of the marker gene. The nonchimeric nature of the callus and the parental transforrnants ($R_0$) was suggested by germline transmission and the identical Southern blot hybridization patterns and intensities of the transforming DNA in callus, $R_0$ plants and $R_1$ progeny that segregated for the transformed gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced isolated and purified DNA segments. In this application of PCR it is first necessary to reverse transcribe RNA into DNA, using enzymes such as reverse transcriptase, and then, through the use of conventional PCR techniques, on amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

2. Gene Expression

While Southern blotting and PCR may be used to detect the isolated and purified DNA segment in question, they do not provide information as to whether the isolated and purified DNA segment is being expressed. Expression may be evaluated by specifically identifying the protein products of the introduced isolated and purified DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focussing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radio labeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of isolated and purified DNA segments encoding enzymes or storage proteins which change amino acid composition and may be detected by amino acid analysis, or by enzymes that change starch quantity that may be analyzed by near infrared reflectance spectrometry. Morphological changes may include greater stature or thicker stalks. Most often changes in response of plants or plant parts to imposed treatments are evaluated under carefully controlled conditions termed bioassays.

D. Establishment of the Introduced DNA in Other Plant Varieties

Fertile, transgenic plants may then be used in a conventional breeding program in order to incorporate the isolated and purified DNA segment into the desired lines or varieties. Methods and references for convergent improvement of are given by Hallauer et al. (1988), incorporated herein by reference. Among the approaches that conventional breeding programs employ is a conversion process (backcrossing). Briefly, conversion is performed by crossing the initial transgenic fertile plant to elite inbred lines (which may or may not be transgenic) to yield an $F_1$ hybrid plant. The progeny from this cross will segregate such that some of the plants will carry the isolated and purified DNA segment whereas some will not. The plants that do carry the isolated and purified DNA segment are then crossed again to the elite inbred lines resulting in progeny that segregate once more. This backcrossing process is repeated until the original elite inbred has been converted to a line containing the isolated and purified DNA segment, yet possessing all important attributes originally found in the parent. Generally, this will require about 6–8 generations. Then the resultant $F_n$ hybrid is usually selfed 5–7 times to yield an inbred line. A separate backcrossing program will be generally used for every elite line that is to be converted to a genetically engineered elite line.

Generally, the commercial value of the transformed plants produced herein will be greatest if the isolated and purified DNA segment can be incorporated into many different hybrid combinations. A farmer typically grows several hybrids based on differences in maturity, standability, and other agronomic traits. Also, the farmer must select a hybrid based upon his or her geographic location since hybrids adapted to one region are generally not adapted to another because of differences in such traits as maturity, disease, drought and insect resistance. As such, it is necessary to incorporate the gene into a large number of parental lines so that many hybrid combinations can be produced containing the isolated and purified DNA segment.

Plant breeding and the techniques and skills required to transfer genes from one line or variety to another are well known to those skilled in the art. Thus, introducing an isolated and purified DNA segment, preferably in the form of recombinant DNA, into any other line or variety can be accomplished by these breeding procedures.

E. Alteration of Transgene Insertions

At anytime during the process of incorporation of a transgene into other varieties of the plant species, alterations in the transgene insertion may be identified or selected. Preferably, alterations are induced early in the process of incorporating the transgene insertion into other varieties, so as to minimize the number of further variety conversions, e.g., backcross conversions, that must be made after the altered transgene insertion is selected. The use of homologous recombination to alter a transgene insertion requires the presence of a directly repeated DNA sequence within the transgene insertion. Directly repeated sequences may be present on a plasmid vector when introduced in a plant. For example, plasmid pMON19344 (FIG. 4) comprises a cryIA (b) gene flanked by directly repeated P-e35S and hsp70 intron sequences. Furthermore, the nptII gene in pMON19344 is flanked by directly repeated nopaline synthase (NOS) 3' sequences. Similarly, a single transgene on a plasmid vector may be flanked by directly repeated sequences. Integration of plasmid vectors such as pMON19344 as a linear transgene insertion leads to both the cryIA(b) and nptII genes being flanked by directly repeated sequences.

Alternatively, directly repeated DNA sequences may be generated in the transgene insertion process by rearrangements, duplications and tandem integrations of DNA sequences in the transgene insertion. Therefore, although directly repeated DNA sequences are not present on the plasmid vectors that are introduced into the plants, direct repeats are produced during the DNA integration process. Regardless of the process used, the result is a transgene insertion comprising directly repeated DNA sequences.

In order for recombination between direct repeats to delete a transgene and be passed on to the next generation, the recombination event must occur in the germline, or upstream of the germline and then enter the germline. Although somatic recombination is known in plants (Evans and Paddock, 1979; Peterhans et al., 1990; Gal et el., 1991; Assad and Signer, 1992; Swoboda et al, 1993; Swoboda et al., 1994; Jelesko et al., 1999; Zubko et al., 2000), it is likely that recombination frequencies are elevated in meiosis. However, it is advantageous to screen and select for altered transgene insertions amongst a population of transgenic events which has been previously determined to express a transgene at a level to confer a desired phenotype. Screening and selection for transgene insertion event alteration is, therefore, preferably done in plants and most preferably done in plants for which transgene expression data is known. Since several recombinational pathways can lead to deletion (FIGS. 1–3, Table 2) it is not necessary for the transgene to be homozygous, although passing through a homozygous stage may facilitate screening for loss of a transgene when homozygous plants are outcrossed.

In the normal course of plant transformation a transgene insertion occurs at a single chromosomal locus. Therefore, the transformed cell and directly derived transformed plant contain a single copy of the transgene insertion, i.e., the cell and plant are hemizygous. Plants in which recombination between direct repeats have deleted a transgene may be identified in progeny produced through self-fertilization or outcrossing to a plant lacking the transgene insertion. Preferably, plants comprising homozygous transgenic insertions are crossed to non-transgenic plants in order to simplify identification of recombinants.

During the process of meiotic recombination, many types of recombination are possible, including equal recombination between chromosome alleles, also known as allelic recombination. It is anticipated that allelic recombinants will demonstrate gene expression similar to the parent plant. Selection of progeny plants comprising altered transgene insertions produced through recombination between direct repeats, resulting in the loss of a transgene, is based on identification of progeny plants with altered transgene expression, preferably loss of transgene expression. Altered expression may be detected by a phenotypic assay, e.g., herbicide resistance or insect resistance, or direct assays for enzyme activity or presence of the transgene encoded protein. The presence of an altered transgene insertion is likely in progeny plants in which transgene expression differs from expression in the parent transgenic plant. Alterations in the transgene insertion may be confirmed by PCR or Southern blot analysis.

Alteration of transgene insertion event structure may also be observed in cultured cells, such as callus, following homologous recombination between directly repeated DNA sequences. Therefore, only plants with the desired transgene insertion structure are regenerated. Furthermore, because the insertion alteration occurs in vitro, it is not necessary to segregate unlinked undesirable loci, thereby accelerating the process of generating altered transgene insertion events.

It is possible to enhance the frequency of homologous recombination between directly repeated DNA sequences. For example, expression of the E. coli recA or ruvC genes in plants has been demonstrated to increase ten-fold the frequency of homologous recombination between directly repeated DNA sequences (Reiss et al., 1996; Shalev et al., 1999).

If alteration of transgene insertion events occurs in cultured cells, it is desirable to select for the product of the direct repeat recombination, e.g., deletion of a DNA sequence within the transgene insertion. A preferred method of selecting for a transgene deletion derivative is to include a negative selectable marker gene within the DNA sequence to be deleted. In the presence of a negative selection agent, cells expressing the negative selectable marker gene are killed and, therefore, in the absence of gene expression cells survive. For example, the compound glyceryl glyphosate is not toxic to plant cells. However, the Burkholderia caryophilli PG2982 pehA gene encodes a phosphonate ester hydrolase enzyme that catalyzes the hydrolysis of glyceryl glyphosate to the toxic compound glyphosate (U.S. Pat. No. 5,254,801; Dotson et al., 1996a; Dotson et al. 1996b). Therefore, expression of the pehA gene leads to cell death in the presence of glyceryl glyphosate, but not in the absence of the compound. Other negative selectable markers are known to function in plants. For example, the enzyme cytosine deaminase converts non-toxic 5-fluorocytosine to the toxic compound 5-fluorouracil and has been used as a negative selectable marker in plants (Stouggard,. 1993). In addition, T-DNA gene 2 is useful as a selectable marker in plants (Depicker et al., 1988). The T-DNA gene 2 protein catalyzes the conversion of alpha-napthalene acetamide (NAM) on auxin alpha-napthalene acetic acid (NAA). NAM is not toxic to plant cells, except in the presence of T-DNA gene 2 product and high concentrations of NAM, e.g., 30–300 $\mu$M. Furthermore, the herpes simplex thymidine kinase gene has been used as a negative selectable marker in plants (Czako and Marton, 1994).

Figure 13:
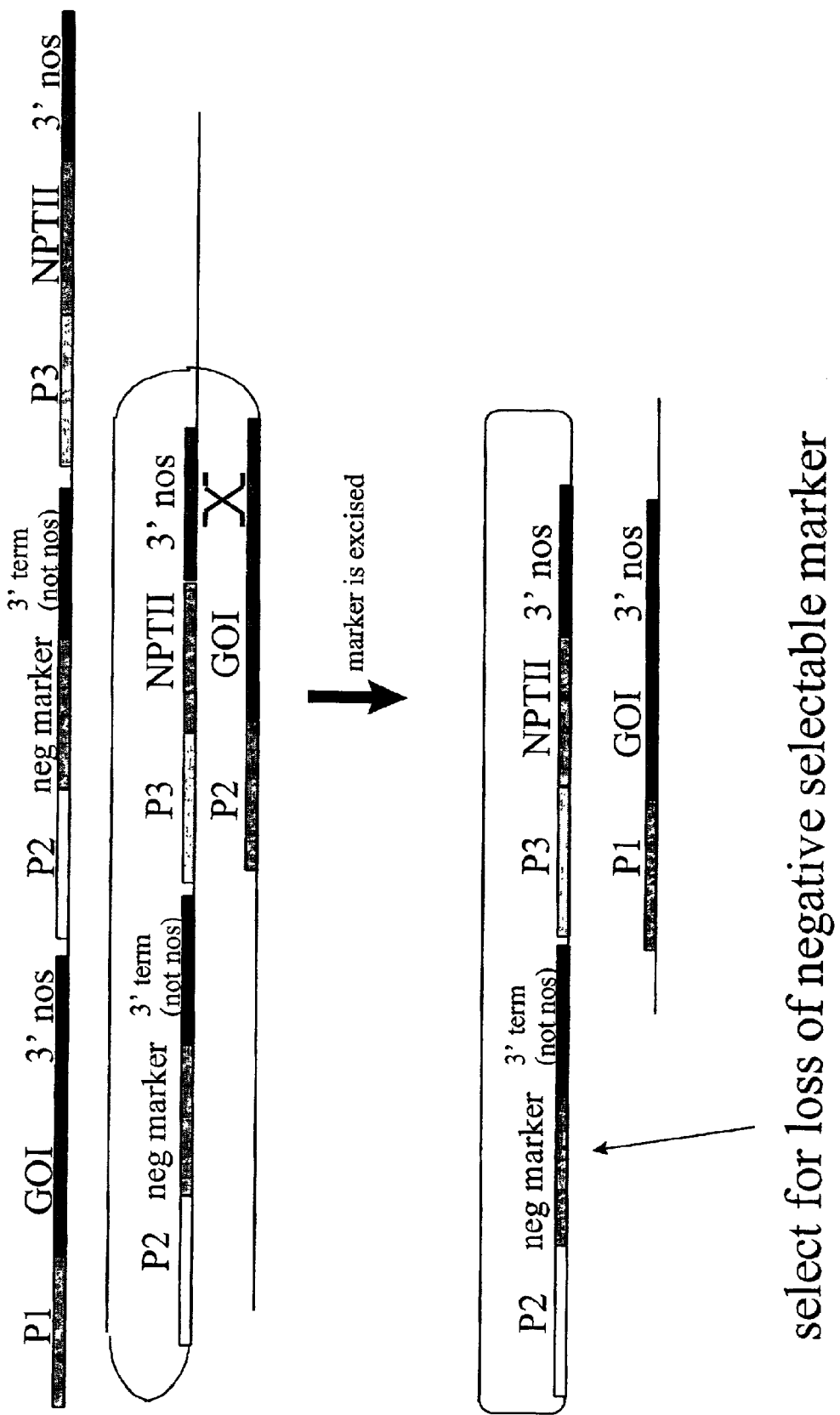
FIG. 13. Use of a negative selectable marker to select for an altered transgene insertion.

A DNA sequence comprising a positive selectable marker gene, e.g., nptII or another positive selectable marker gene, and a negative selectable marker gene, e.g., pehA, T-DNA gene 2, cytosine deaminase gene, flanked by a directly repeated DNA sequence is introduced into a plant. Alternatively, a fusion of the positive and negative selectable marker genes is used. Transformants are identified using an appropriate selective agent-selectable marker gene combination, e.g., kanamycin or paromomycin and the nptII gene. Following identification of transformed cell lines, selection for the negative selectable marker, and therefore deletion of the negative selectable marker gene, is initiated. Resistance to the negative selection agent is indicative of loss of the negative selectable marker gene, i.e., transgene deletion. Transgene deleted cells are also sensitive to the positive selectable marker as both positive and negative selectable markers present between directly repeated DNA sequences are deleted. Selection of transgene deletion derivative events may require removal of the positive selective agent for a period of time prior to imposing negative selection in order to allow for the occurrence of a transgene deletion recombination event. Alternatively, a gradual decrease in positive selection with a concomittant increase in negative selection may be used, or the increase and decrease in positive and negative selection agents may occur simultaneously. FIG. 13 illustrates use of a negative selectable marker to select for cells with altered transgene insertions. Transgene deleted plants are regenerated from cultured cells that are identified following positive and negative selection. Selection of transgene deletions using a negative selectable marker gene was disclosed by Zubko et al., (2000).

F. Uses of Transgenic Plants

The transgenic plants produced herein are expected to be useful for a variety of commercial and research purposes. Transgenic plants can be created for use in traditional agriculture to possess traits beneficial to the grower (e.g., agronomic traits such as resistance to water deficit, pest resistance, herbicide resistance or increased yield), beneficial to the consumer of the grain harvested from the plant (e.g., improved nutritive content in human food or animal feed), or beneficial to the food processor (e.g., improved processing traits). In such uses, the plants are generally grown for the use of their grain in human or animal foods. However, other parts of the plants, including stalks, husks, vegetative parts, and the like, may also have utility, including use as part of animal silage or for ornamental purposes. Often, chemical constituents (e.g., oils or starches) of maize and other crops are extracted for foods or industrial use and transgenic plants may be created that have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the isolated and purified DNA segment may be transferred, e.g., from cells of one species to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences that can be used to identify proprietary lines or varieties.

The following examples are illustrative of the present invention.

EXAMPLE 1

Deletion of the Bar Gene from the Transgenic Event DBT418

Homologous recombination-mediated transgene deletion is a process whereby the structure of a transgene insert can be altered (see FIG. 1). The process is dependent on the presence of direct repeats of DNA sequences in the transgene insertion. Direct repeats may be present in the transgene used for transformation, or they may arise through multi-element integration at the site of transgene insertion. The direct repeats might be, for example, incomplete parts of a transgene that, upon recombination, produce a complete transgene conferring an identifiable phenotype.

Figure 6:
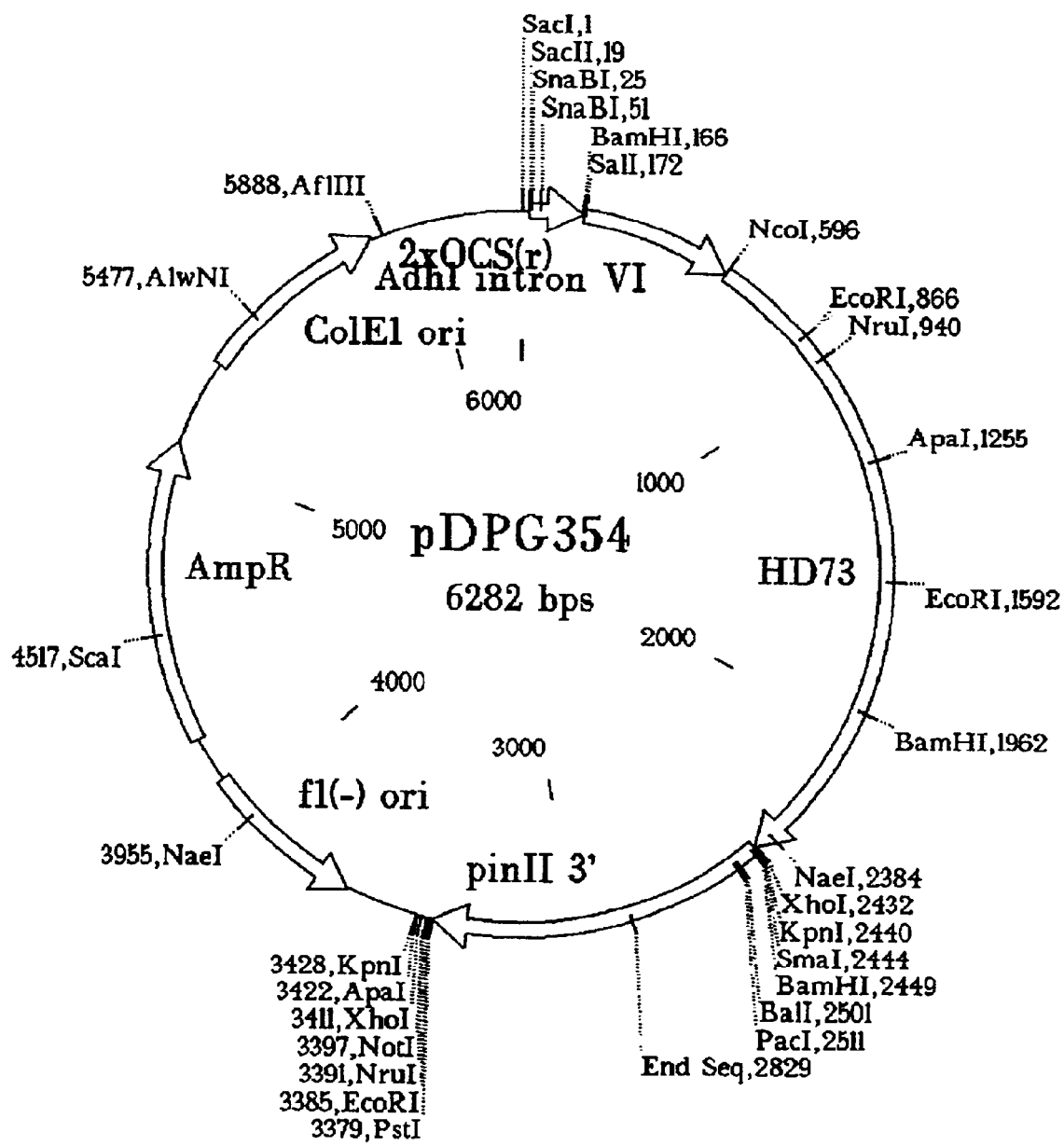
FIG. 6. Plasmid vector pDPG354
Figure 7:
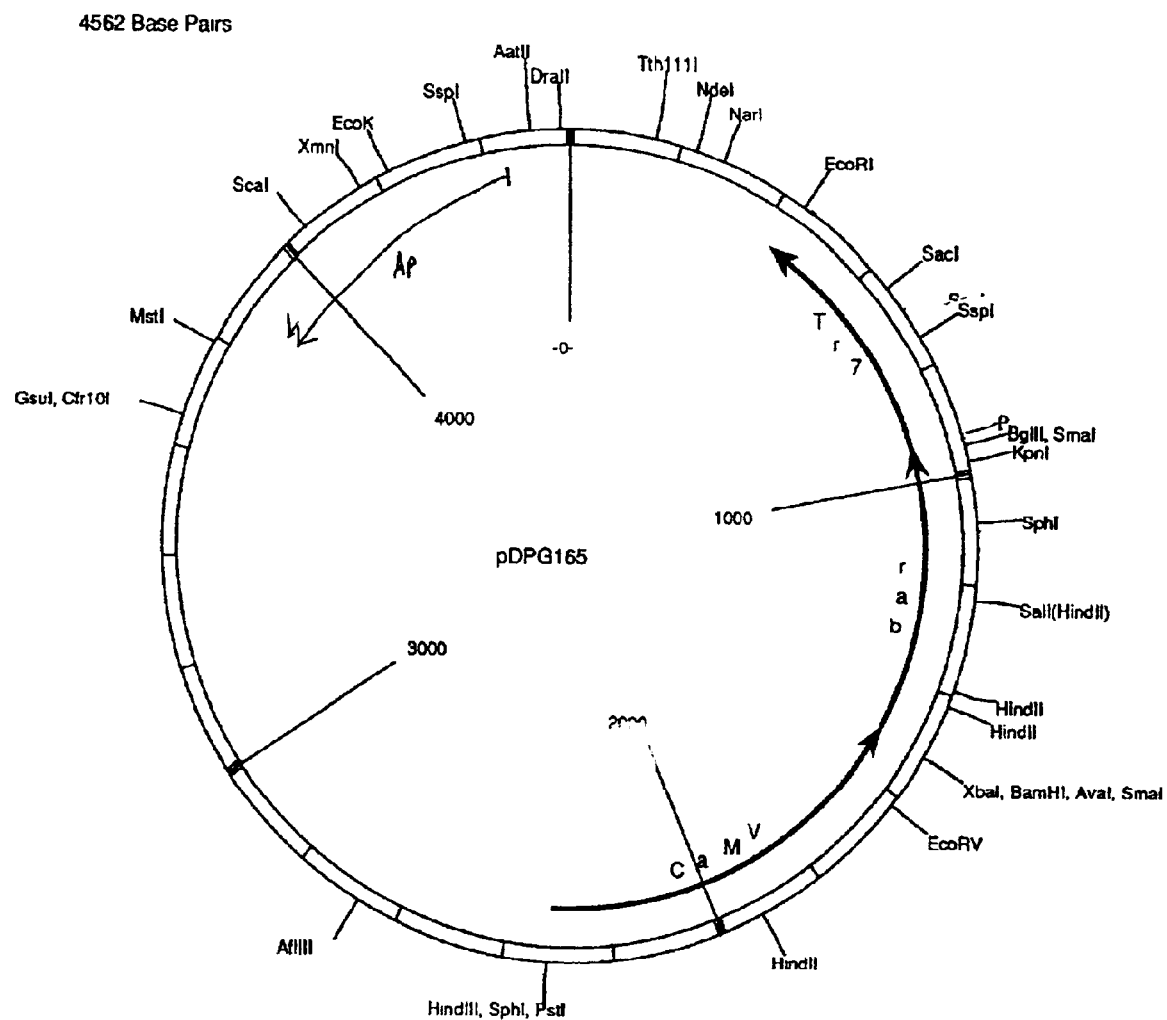
FIG. 7. Plasmid vector pDPG165
Figure 8:
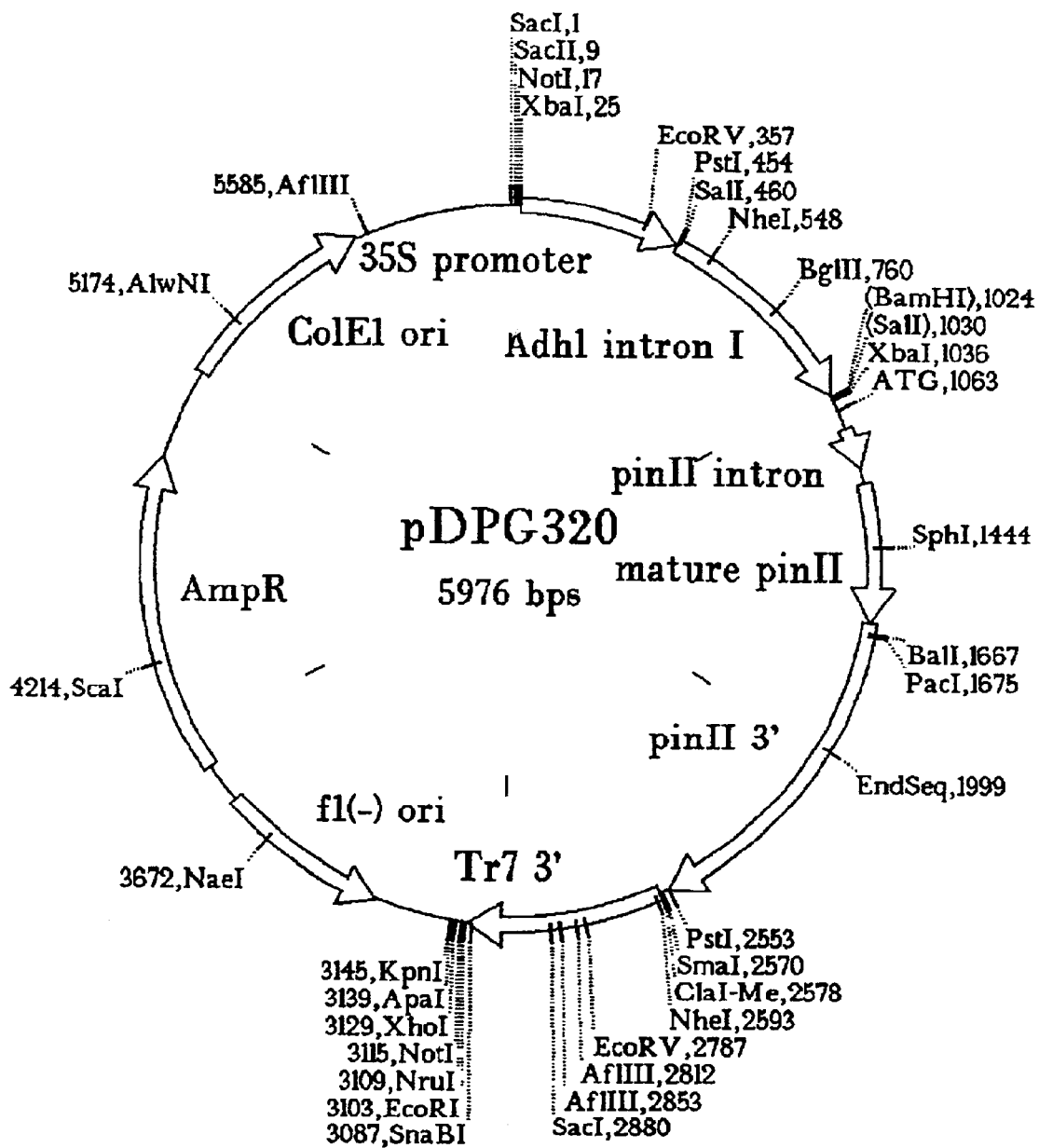
FIG. 8. Plasmid vector pDPG320
Figure 9:
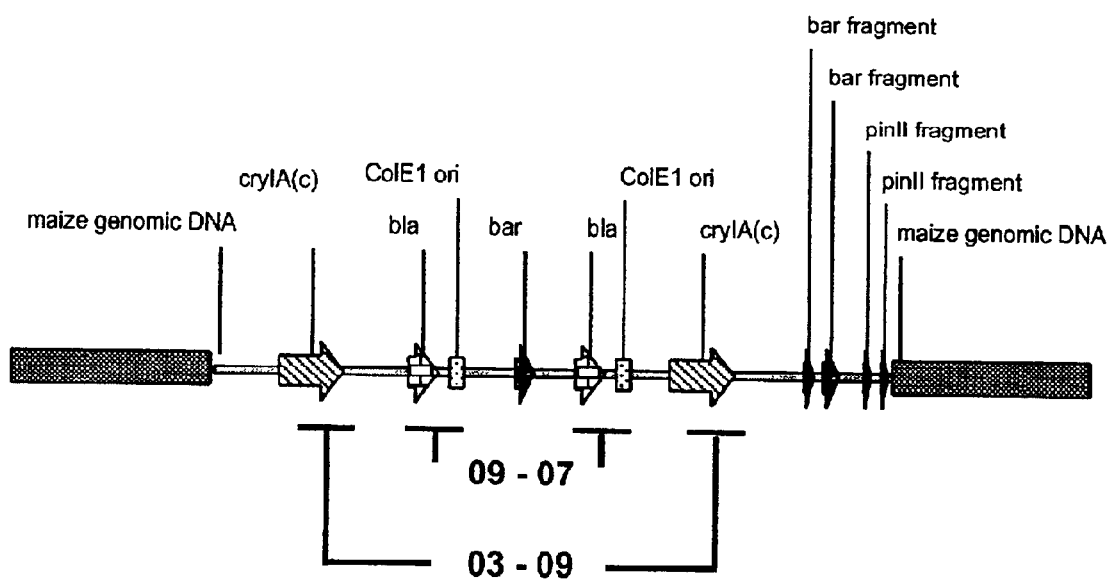
FIG. 9. DBT418 transgene insertion indicating direct repeat sequences that were the substrate for homologous recombination products recovered in the 09–07 and 03–09 altered transgene insertion progeny.

Line DBT418 was produced by microprojectile bombardment of embryogenic cells with plasmid vectors pDPG354 (FIG. 6), pDPG165 (FIG. 7) and pDPG320 (FIG. 8). The structure of the transgene insert in the line DBT418 is diagramed in FIG. 9 and described in detail in U.S.D.A. Petition 9629101p for deregulation. The insert has one functional copy of a bar gene conferring resistance to the herbicide phosphinothricin. Flanking the bar gene on both sides are directly repeated DNA sequences that include cloning vector DNA and Bt toxin encoding DNA sequences. In addition to these direct repeats, there are additional shorter regions of direct homology that also may serve as target sequences for non-reciprocal recombination mediated deletion of transgene DNA within the insert.

In order to identify individuals that have undergone homologous recombination mediated transgene deletion, an assay was carried out to screen for plants that showed a loss of the phosphinothricin resistance phenotype. Southern blot analysis was used to characterize the copy number of transgene elements present in the phosphinothricin sensitive individuals.

Hemizygous DBT418 plants were selfed, and progeny identified that were homozygous for the DBT418 insertion event. These homozygous plants were outcrossed to non-transgenic plants to generate a population of hemizygous seed. Approximately 1,000 seed of a finished inbred, hemizygous for the DBT418 insert, were planted and assayed for phosphinothricin resistance using a nondestructive herbicide leaf painting assay (U.S. Pat. No. 5,489,520). Individuals displaying a necrotic response in the treated area were assayed again by the leaf painting assay for confirmation of the phosphinothricin sensitive phenotype. Five individuals were found to be sensitive to phosphinothricin.

Genomic DNA was isolated and analyzed by Southern blot analysis. The blot was hybridized with probes for the bt, bar and amp genes. Results of this analysis are shown in Table 9.

TABLE 9

Summary of DBT418 Recombinants Displaying Phosphinothricin Sensitivity

| Individual | | Phenotypes and Genotypes | | | |
|---|---|---|---|---|---|
| Row | Plant | Phenotype[a] | # full-length bar gene copies | # partial bar gene copies | # full-length Bt gene copies | # full-length Amp copies |
| 03 | 09 | S | 0 | 1 | 1 | 1 |
| 08 | 17 | S | 0 | 1 | >3 | >5 |
| 09 | 07 | S | 0 | 1 | 2 | 2 |
| 11 | 18 | S | 0 | 1 | 2 | 2 |
| 15 | 11 | S | 0 | 1 | 2 | 2 |

TABLE 9-continued

Summary of DBT418 Recombinants Displaying Phosphinothricin Sensitivity

| | | | Phenotypes and Genotypes | | | |
|---|---|---|---|---|---|---|
| Individual | | | # full-length bar | # partial bar gene | # full-length Bt | # full-length Amp |
| Row | Plant | Phenotype[a] | gene copies | copies | gene copies | copies |
| Normal DBT418 | | R | 1 | 1 | 2 | 3 |

[a]PPT resistant (R) or Sensitive (S)

All five phosphinothricin-sensitive individuals lacked the full length bar gene present in phosphinothricin-resistant DBT418. The data also showed that each phosphinothricin-sensitive plant still contained transgene DNA corresponding to the partial bar gene copy, the Bt gene and the amp gene. The copy number of these transgenes varied among the phosphinothricin sensitive individuals. The data shows three classes of variants. Plant 03–09 lacked the full length bar gene copy, but retained a partial bar gene copy, one copy of the Bt gene and one copy of the amp gene (FIG. 10). Plants 09–07, 11–18, and 15–11 represent a second class of variants that lacked the full length bar gene, but retained a partial bar gene, two copies of the Bt gene, and two copies of the amp gene (FIG. 10). Finally, a third class was observed where the full length bar gene copy was absent, but a partial bar gene copy was retained, and where the copy number of the Bt gene and amp gene were increased compared to DBT418.

EXAMPLE 2

Deletion of nptII or cryIA(b) Gene from the Transgenic Events "MON849" and "MON850"

Transformation events (MON849) and (MON 850) were produced by microprojectile bombardment of cells with plasmid vector using pMON19344 (FIG. 4). The structure of the MON849 transgene insert is diagrammed in FIG. 11. The insert has one copy of an nptII gene conferring resistance to kanamycin and one copy of a cryIA(b) Bt gene conferring resistance to certain insect pests. Both the nptII and cryIA(b) coding regions are flanked on the 5¢ ends by identical 35S promoters and hsp70 introns. Both the nptII and cryIA(b) coding regions are flanked on the 3¢ ends by identical nos terminators. Recombination events between the 35S promoter and hsp70 intron regions of the cryIA(b) gene and the 35S promoter and hsp70 intron regions of the nptII gene result in the loss of the cryIA(b) gene (FIG. 11). Recombination events between the nos terminator region of the cryIA(b) gene and the nos terminator region of the nptII gene result in the loss of the nptII gene (FIG. 11). The latter recombination event is useful in that (i) the resultant plant would be genetically more stable, as loss of the cryIA(b) gene would not occur during seed increase, (ii) the resultant plant would be phenotypically more stable, as there would be no repeated genetic elements within the insert, and (iii) the ancillary DNA sequence encoding nptII that does not contribute to the designed insect resistance phenotype is deleted.

Plant material was prepared by self pollinating plants hemizygous for the transgene insert, identifying individuals homozygous for the transgene insert in the subsequent generation, and crossing the homozygous individuals to nontransgenic plants. The resulting population was hemizygous for the transgene insert.

To identify non-reciprocal recombinants within this MON849 progeny population, transgene expression assays were carried out on approximately 1,000 individuals and 7 individuals that differed in phenotype from the parent were identified (Table 10) (frequency of 0.4%). PCR analysis carried out for the cryIA(b) and nptII genes showed that the lack of a transgene phenotype correlated with the absence of the particular transgene. Plant 20–102-A (plant numbers refer to range-row-stake number, as listed in Table 10) appears to be a recombinant that has lost the nptII gene. Plant 20–103–3 lacks both transgenes and may be the result of pollen contamination. Five MON849 progeny plants show an apparent recombination in which the cryIA(b) gene was lost and the nptII gene retained. A similar transgene stability assay was also carried out on approximately 1,000 individuals derived from a parent plant that was homozygous for the MON850 event and about 0.7% of the individuals differed from the parent. One MON849 progeny plant and one MON850 progeny plant showed an apparent recombination in which the nptII gene was lost and the cryIA(b) gene retained. The recombinant individuals lacking the nptII gene were crossed with a variety of inbreds.

TABLE 10

Genetic Analysis (PCR) of Mon849 and Mon850 Plants Displaying Off-type Phenotypes

| | | | | Phenotypes | | Genotypes (PCR) | |
|---|---|---|---|---|---|---|---|
| Event | Range | Row | Stake # | CryIA(b) | NPTII | CryIA(b) | NPTII |
| MON850 | 19 | 126 | 8[1] | o | o | o | o |
| MON850 | 18 | 125 | 7[1] | o | o | o | o |
| MON850 | 18 | 129 | B | + | o | + | o |
| MON850 | 19 | 125 | C | + | o | + | + |

TABLE 10-continued

Genetic Analysis (PCR) of Mon849 and Mon850 Plants Displaying Off-type Phenotypes

| Event | Range | Row | Stake # | Phenotypes | | Genotypes (PCR) | |
|---|---|---|---|---|---|---|---|
| | | | | CrylA(b) | NPTII | CrylA(b) | NPTII |
| MON849 | 20 | 102 | A | + | o | + | o |
| MON849 | 18 | 113 | 6 | o | + | o | + |
| MON849 | 20 | 105 | 5 | o | + | o | + |
| MON849 | 19 | 105 | 4 | o | + | o | + |
| MON849 | 20 | 103 | 3 | o | o | o | o |
| MON849 | 20 | 99 | 2 | o | + | o | + |
| MON849 | 19 | 99 | 1 | o | + | o | o |

[1]These plants were small in stature, consistent with these individuals being nontransgenic inbred.

Southern blot analyses of the recombinant MON849 individuals were carried out in order to confirm that gene deletion was mediated by homologous recombination. As shown in Table 11, both nptII+/cryIA(b)– and nptII–/cryIA(b)+ individuals displayed a pattern of hybridizing bands that are indicative of homologous recombination mediated transgene deletion.

TABLE 11

Southern hybridization band sizes for MON849 F1 derivatives

| | | | Probe A = CryIA(b) | | Probe B = nptII | |
|---|---|---|---|---|---|---|
| Kan[R] | CrylA(b) ELISA | % in F$_1$ progeny[*] | EcoRI (E) | NcoI (N) | EcoRI (E) - NcoI (N) | XbaI (X) |
| + | + | 99.3% | 10.0 | 6.1 | 2.6 | 5.2 |
| + | o | 0.6% | ? | ? | 7.3 | 5.2 |
| o | + | 0.1% | 10.0 | 5.9 | ? | ? |

[*]n = 1000

Quantitative ELISA analysis of a nptII–/cryIA(b)+ individual derived from both MON849 and MON850 events indicated that deletion of the nptII gene did not significantly compromise the expression of the cryIA(b) gene as shown in Table 12.

TABLE 12

Quantitative ELISA on MON849 and MON850 F1 Derivatives

| Phenotype | | CryIA(b) Protein (μg/g dry wt.) | |
|---|---|---|---|
| Kan[R] | CrylA(b) | MON849 | MON850 |
| + | + | 18.48 | 11.22 |
| o | + | 11.59 | 17.36 |

Finally, in looking at the relationship between the repeated sequences flanking the deleted gene and the frequency of recombination, a direct correlation was observed between the length of the direct repeat sequences flanking the deleted gene and the observed frequency of homologous recombination mediated transgene deletion (Table 13). The observed gene deletion frequency is estimated at about 0.1% per 287 bp of homologous direct repeat sequence ±19 bp (S.E).

TABLE 13

Correlation Between Flanking Direct Repeat Length and Frequency of Intervening Gene Deletion

| Event | Deleted Gene | Direct Repeats | Repeat Length | % Deletion Recombinants |
|---|---|---|---|---|
| Mon849 | nptII | nos | 0.3 kbp | 0.1% |
| Mon849 | CrylA(b) | e35S-hsp70 | 1.5 kbp | 0.6% |
| DBT418 | bar | pDPG354 | 6.2 kbp | 2.0% |

EXAMPLE 3

Alteration of a Transgene Insertion Event in Transformed Cells

Figure 12:
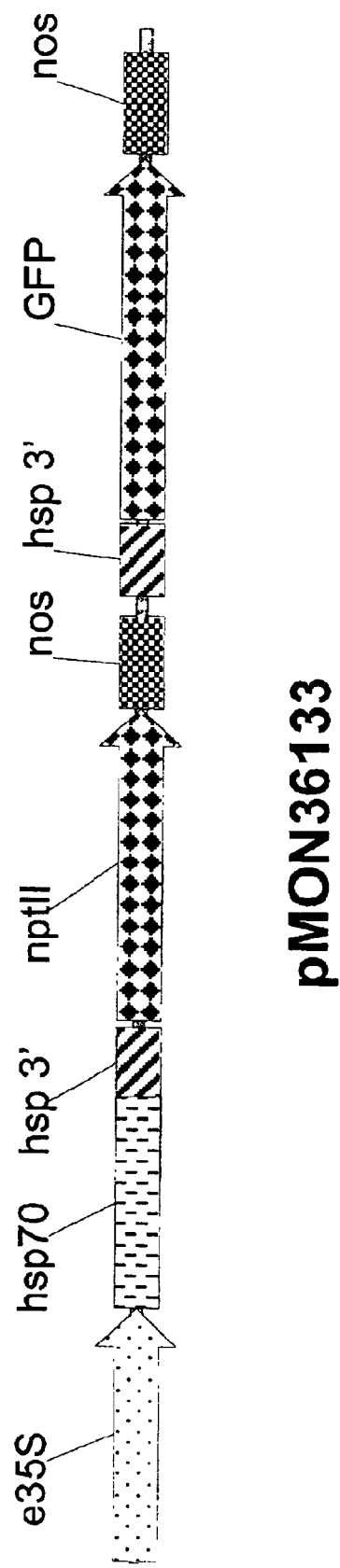
FIG. 12. Plasmid vector pMON36133.

The plasmid vector pMON36133 (FIG. 12) was constructed wherein a neomycin phosphotransferase II (nptII) gene is flanked on both the 5' and 3' ends by direct repeats of sequences derived from the 3' end of the maize hsp70 intron. The vector further comprises a gene encoding green fluorescent protein (GFP) that lacks a promoter and is not expressed in a plant cell. Deletion of the sequences between the repeated hsp70 sequences produces a transgene wherein the 35S promoter and hsp70 intron are operable linked to the GFP gene and therefore, the GFP protein is expressed.

The plasmid vector pMON36133 was introduced into Black Mexican Sweet maize cells using microprojectile bombardment. Transformed callus was selected based on resistance to kanamycin conferred by the nptII gene. Sectors of GFP expressing tissues were observed in the transformants, indicating that the nptII gene was deleted, thereby activating expression of the GFP gene.

In conclusion, homologous recombination can be used to remove unwanted transgenic DNA sequences from genetically transformed plants. Target trait gene expression was not compromised by the deletion of a linked marker gene. Moreover, the observed recombination frequency appears to be directly proportional to the length of the repeats within the region being targeted for gene deletion. Thus, transformation can be designed to facilitate subsequent gene deletion, such as in pMON19344.

All publications, patents and patent applications cited above are incorporated by reference herein, as though fully set forth. The invention has been described with reference to various specific and preferred embodiments and will be further described by reference to the following detailed examples. It is understood, however, that there are many extensions, variations, and modifications on the basic theme of the present invention beyond that shown in the examples and description, which are within the spirit and scope of the present invention.

REFERENCES

The references listed below are incorporated herein by reference to the extent that they supplement, explain, provide a background for, or teach methodology, techniques, and/or compositions employed herein.

U.S. Pat. No. 4,535,060
U.S. Pat. No. 4,940,835
U.S. Pat. No. 4,940,838
U.S. Pat. No. 4,959,317
U.S. Pat. No. 5,134,074
U.S. Pat. No. 5,168,053
U.S. Pat. No. 5,254,801
U.S. Pat. No. 5,258,300
U.S. Pat. No. 5,268,526
U.S. Pat. No. 5,276,268
U.S. Pat. No. 5,290,924
U.S. Pat. No. 5,302,523
U.S. Pat. No. 5,322,783
U.S. Pat. No. 5,354,855
U.S. Pat. No. 5,384,253
U.S. Pat. No. 5,451,513
U.S. Pat. No. 5,464,765
U.S. Pat. No. 5,482,852
U.S. Pat. No. 5,489,520
U.S. Pat. No. 5,500,365
U.S. Pat. No. 5,508,184
U.S. Pat. No. 5,508,468
U.S. Pat. No. 5,510,471
U.S. Pat. No. 5,538,877
U.S. Pat. No. 5,538,880
U.S. Pat. No. 5,550,318
U.S. Pat. No. 5,563,055
U.S. Pat. No. 5,563,324
U.S. Pat. No. 5,590,390
U.S. Pat. No. 5,591,616
U.S. Pat. No. 5,593,963
U.S. Pat. No. 5,610,042
U.S. Pat. No. 5,624,824
U.S. Pat. No. 5,625,047
U.S. Pat. No. 5,654,182
U.S. Pat. No. 5,658,772
U.S. Pat. No. 5,689,052
U.S. Pat. No. 5,723,765
U.S. Pat. No. 5,743,477
U.S. Pat. No. 5,780,708
U.S. Pat. No. 5,780,709
U.S. Pat. No. 5,792,924
U.S. Pat. No. 5,801,030
U.S. Pat. No. 5,831,011
U.S. Pat. No. 6,627,061
EP 0154204 B1
PCT Publication No. WO 92/17598
PCT Publication No. WO 97/04103
PCT Publication No. WO 97/26366
PCT Publication No. WO 98/26064
PCT Publication No. WO 99/32642
Abdullah et al., 1986. *Biotechnology*, 4:1087
Abel, P. P., Nelson, R. S., De, B., Hoffman, N., Rogers, S. G., Fraley, R. T. and Beachy, R. N. 1986. *Science* 232:738–743.
Abremski et al. 1983. *Cell* 32:1301
An, G. et al. 1989. *Plant Cell* 1:115–122.
Armaleo et al., 1990. *Curr. Genet.* 17(2):97–103

Assad, F. A., Signer, E. R., 1992, *Genetics* 132:553–566.
Athma, P., Peterson, T., 1991. *Genetics* 128:163–173
Barkai-Golan, R., Mirelman, D., Sharon, N. 1978. *Arch. Microbiol* 116:119–124.
Bates, *Mol. Biotechnol.*, 1994. 2(2):135–145
Battraw and Hall, 1991. *Theor. App. Genet.*, 82(2):161–168
Beck, E., Ludwig, G., Auerswald, E. A., Reiss, B. & Schaller, H. 1982. *Gene* 19(3):327–36.8
Bernal-Lugo, I. and Leopold, A. C. 1992. *Plant Physiol.* 98:1207–1210.
Berzal-Herranz et al., 1992. *Genes and Devel.*, 6:129–134
Bevan, M., Barnes, W. M., Chilton, M. D., 1983. *Nucleic Acid Research.* 11:369–385.
Bhattacharjee; An; Gupta, 1997. *J. Plant Bioch. and Biotech.* 6, (2):69–73
Blackman, S. A., Obendorf, R. L., Leopold, A. C. 1992. *Plant Physiol.* 100:225–230.
Bol, J. F., Linthorst, H. J. M., Cornelissen, B. J. C. 1990. *Annu. Rev. Phytopath.* 28:113–138.
Bottjer et al., 1985. *Experimental Parasitology,* 60:239–244
Bouchez D., Tokuhisa J. G., Llewellyn D. J., Dennis E. S. and Ellis J. G., 1989. *EMBO Journal* 8(13):4197–4204.
Bower et al., 1992. *The Plant Journal,* 2:409–416.
Bowler, C., Van Montagu, M., and Inze, D. 1992. *Ann Rev. Plant Physiol.* 43:83–116.
Branson, T. F. and Guss, P. L. 1972. *Proceedings North Central Branch Entomological Society of America* 27:91–95.
Broakaert, W. F., Parijs, J., Leyns, F., Joos, H., Peumans, W. J. 1989. *Science* 245:1100–1102.
Buchanan-Wollaston et al., 1992. *Plant Cell Reports* 11:627–631.
Buising and Benbow, 1994. *Mol Gen Genet,* 243(1):71–81.
Callis, J., Fromm, M., Walbot, V. 1987., Genes and Develop. 1:1183–1200.
Campbell, W. C. ed. 1989. In: *Avermectin and Abamectin.*
Carrer, H., et al. 1993. *Mol. Gen. Genet.* 241:49
Casa et al., 1993. *Proc. Nat'l Acad. Sci. USA,* 90(23):11212–11216
Cech et al., 1981. *Cell,* 27:487–496
Chandler, V. L., Radicella, J. P., Robbins, P. P., Chen, J., Turks, D. 1989. *The Plant Cell* 1:1175–1183
Chowrira et al, 1993. *J Biol Chem.,* 268:19458–62
Chowrira et al., 1994. *J Biol. Chem.,* 269:25856–25864
Christou; Murphy; Swain, 1987. *Proc. Nat'l Acad. Sci. USA,* 84(12):3962–3966
Chu C. C., Wang C. C., Sun C. S., Hsu C., Yin K. C., Chu C. Y., Bi F. Y. 1975. *Scientia Sinica* 18:659–668
Clark, R. 1982. *J Plant Nutrition* 5:1039.
Coe, E. H., Neuffer, M. G., and Hoisington, D. A. 1988. in *Corn and Corn Improvement*, Sprague, G. F. and Dudley, J. W., eds., pp. 81–258
Comai et al., 1985. *Nature,* 317:741–744
Conkling, M. A., Cheng, C. L., Yamamoto, Y. T., Goodman, H. M. 1990. *Plant Physiol.* 93:1203–1211
Coruzzi et al. 1971. *EMBO J.* 3:1671
Coxson, D. S., McIntyre, D. D., and Vogel, H. J. 1992. *Biotropica* 24:121–133.
Cuozzo, M., O'Connell, K. M., Kaniewski, W., Fang, R. X., Chua, N. and Turner, N. 1988. *Bio/Technology* 6:549–553.
Cutler, A. J., Saleem, M., Kendell, E., Gusta, L. V., Georges, F., Fletcher, G. L. 1989. *J Plant Physiol* 135:351–354.
Czako, M. and Marton, L. 1994. The herpes simplex virus thymidine kinase gene as a conditional negative selectable marker gene in *Arabidopsis thaliana*. Plant Physiol. 104:1067–1071.

Czapla and Lang 1990. *J. Econ. Entomol.* 83:2480–2485.
Davies, T. G. E., Thomas, H., Thomas, B., Rogers, L. J. 1990. *Plant Physiol.* 93:588–595.
De Block et al., 1987. *The EMBO Journal,* 6(9):2513–2518
De Block, De Brouwer, Tenning, 1989. *Plant Physiol.,* 91:694–701
Dekeyser et al. 1990. *Plant Cell* 2:591–602.
Dellaporta, S., Greenblatt, I., Kermicle, J., Hicks, J. B., Wessler, S. 1988. in *Chromosome Structure and Function: Impact of New Concepts, 18th Stadler Genetics Symposium,* J. P. Gustafson and R. Appels, eds (New York: Plenum Press) pp. 263–282.
Depicker et al., 1988. *Plant Cell Reports,* 7:63–66
D'Halluin et al., 1992. *Plant Cell,* 4(12):1495–1505
Dotson, S. B., Lnahan, M. B., Smith, A. G., and Kishore, G. M. 1996a. A phosphonate monoester hydrolase from *Burkholderia caryophilli* PG2982 is useful as a conditional lethal gene in plants. Plant J. 10:383–392.
Dotson, S. B., Smith, C. E., Ling, C. S., Barry, G. F. and Kishore, G. M. 1996b. J. Biol. Chem. 271 (42): 25754–25761.
Dure, L., Crouch, M., Harada, J., Ho, T. -H. D., Mundy, J., Quatrano, R., Thomas, T., and Sung, Z. R. 1989. *Plant Molecular Biology* 12:475–486.
Ebert, P. R., Ha, S. B., An. G. 1987. *PNAS* 84:5745–5749.
Ehrenshaft et al., 1999. *Current Genetics,* 34(6):478–485
Ellis J. G., Llewellyn D. J., Walker J. C., Dennis E. S., and Peacock W. J., 1987. *EMBO Journal* 6(11):3203–3208.
Erdmann, N., Fulda, S., and Hagemann, M. 1992. *J. Gen. Microbiology* 138:363–368.
Evans, D. A. and Paddock, E. F. 1979. Mitotic Crossing-Over in Higher Plants. In: *Plant Cell and Tissue Culture, Principles and Applications.* Sharp, W. R. et al. eds. Ohio State Unversity Press.
Finkle B. J., Ulrich J. M., Rains W., Savarek S. J., 1985. *Plant Sci* 42:133–140.
Fitzpatrick, T. 1993. *Gen. Engineering News* 22 (March 7):7.
Forster and Symons, 1987. *Cell,* 49:211–220
Fraley et al., 1985. *Bio/Technology,* 3:629–635
Fransz, P. F., de Ruijter, N. C. A., Schel, J. H. N. 1989. *Plant Cell Rep* 8:67–70
Fromm et al., 1986. *Nature* 319:791–793
Fromm M. E. et al. 1990. *Bio/Technology,* 8, 833
Fromm, H., Katagiri, F., Chua, N. H. 1989. *The Plant Cell* 1:977–984.
Gal, S., Pisan, B., Hohn, T., Grimsley, N., Hohn, B., 1991, *EMBO J.* 10:1571–1578
Gallie, D. R., Lucas, W. J., Walbot, V. 1989. *The Plant Cell* 1:301–311.
Gatehouse, A. M., Dewey, F. M., Dove, J., Fenton, K. A., Dusztai, A. 1984. *J Sci Food Agric* 35:373–380.
Gelvin, S. B., Schilperoort, R. A., Varma, D. P. S., eds., 1990. *Plant Molecular Biology Manual*
Gerlach et al., 1987. *Nature* 328:802–805
Ghosh-Biswas et al., 1994. *J. Biotechnol.,* 32(1):1–10
Gordon-Kamm W. J. et al. 1990. *Plant Cell,* 2, 603
Goring, D. R., Thomson, L., Rothstein, S. J. 1991. *Proc. Natl. Acad Sci. USA* 88:1770–1774.
Guerrero, F. D., Jones, J. T., Mullet, J. E. 1990. *Plant Molecular Biology* 15:11–26.
Gupta, A. S., Heinen, J. L., Holaday, A. S., Burke, J. J., and Allen, R. D. 1993. *Proc. Natl. Acad. Sci USA* 90:1629–1633.
Hagio, Blowers, Earle, 1991. *Plant Cell Rep.,* 10(5):260–264
Hallauer et al. 1988. In: *Corn and Corn Improvement,* Sprague et al. (eds.) pp. 463–564

Hammock, B. D., Bonning, B. C., Possee, R. D., Hanzlik, T. N., and Maeda, S. 1990. *Nature* 344:458–461.
Hardy et al. 1997. *J. Virology* 71:1842
Haseloff and Gerlach, 1988. *Nature,* 334:585–591
He et al, 1994. *Plant Cell Reports,* 14 (2–3):192–196
Heijne et al. 1989. *Eur. J. Biochem.,* 180, 535
Hemenway, C., Fang, R., Kaniewski, W. K., Chua, N. and Turner, N. E. 1988. *The EMBO J.* 7:1273–1280.
Hensgens et al., 1993. *Plant Mol. Biol.,* 22(6):1101–1127
Herrera-Estrella et al. 1990. *Proc. Natl. Acad. Sci. USA,* 87:9534–9537.
Hiei et al., 1997. *Plant. Mol. Biol.,* 35(1–2):205–218
Hilder, V. A., Gatehouse, A. M. R., Sheerman, S. E., Barker, R. F., Boulter, D. 1987. *Nature* 330:160–163.
Hinchee, M. A. W., Connor-Ward, D. V., Newell, C. A., McDonell, R. E., Sato, S. J.,
Gasser, C. S., Fischhoff, D. A., Re, C. B., Fraley, R. T., Horsch, R. B. 1988. *Bio/technol* 6:915–922.
Holmberg et al., 1997. *Nature Biotechnology,* 15(3): 244–247
Hou and Lin, 1996. *Plant Physiology,* 111 (Sup 2):166
Hudspeth, R. L. and J. W. Grula. 1989. *Plant Mol. Biol.* 12:579–589.
Ikeda, H., Kotaki, H., Omura, S. 1987. *J Bacteriol* 169:5615–5621.
Ikuta, N., Souza, M. B. N., Valencia, F. F., Castro, M. E. B., Schenberg, A. C. G., Pizzirani-Kleiner, A., Astolfi-Filho, S. 1990. *Bio/technol* 8:241–242.
Ishida et al., *Nat. Biotechnol.,* 1996. 14(6):745–750
Jefferson R. A., 1987. *Plant Molecular Biology Reporter,* 5, 387–405
Jelesko, J. G., Harper, R., Furuya, M., Gruissem, W., *Proc. Natl. Acad. Sci USA* 96:10302–10307
Jenkins, G., and Cundliffe, E. 1991. *Gene* 108(1):55–62.
Johnson et al., 1989. *Proc. Natl. Acad. Sci. USA,* 86:9871–9875
Joshi, C. P. 1987. *Nucleic Acids Res.,* 15:6643–6653.
Joyce, 1989. *Nature,* 338:217–244
Kaasen, I., Falkenberg, P., Styrvold, O. B., Strom, A. R. 1992. *J. Bacteriology* 174:889–898.
Kaeppler et al., 1990. *Plant Cell Reports* 9:415–418
Kaeppler, Somers, Rines, Cockburn, 1992. *Theor. Appl. Genet.,* 84(5–6):560–566
Karsten, U., West, J. A. and Zuccarello, G. 1992. *Botanica Marina* 35:11–19.
Kasuga, et al. 1999. *Nat. Biotech.* 17:287
Katz et al. 1983. *J. Gen. Microbiol.* 129:2703–2714.
Keegstra et al. 1989. *Ann. Rev. Plant Physiol. Plant Mol. Biol.,* 40:471
Keller et al. 1989. *EMBO J.,* 8(5):1309–1314.
Kim and Cech, 1987. *Proc. Natl. Acad. Sci. USA,* 84:8788–8792
Klee, Yanofsky, Nester, 1985. *Bio-Technology,* 3(7):637–642
Knittel, Gruber; Hahne; Lenee, 1994. *Plant Cell Reports,* 14(2–3):81–86
Koster, K. L. and Leopold, A. C. 1988. *Plant Physiol.* 88:829–832.
Laufs, J., Wirtz, U., Kammann, M., Matzeit, V., Schaefer, S., Schell, J., Czernilofsky, A. P., Baker, B., and Gronenborn, B. 1990. *Proc. Natl. Acad. Sci USA.* 87:7752–7756.
Laursen, C. M., Krzyzek, R. A., Flick, E. E., Anderson, P. C., Spencer, T. M. 1994. *Plant Molecular Biology.* 24:51
Lawton, M. A., Tierney, M. A., Nakamura, I., Anderson, E., Komeda, Y., Dube, P., Hoffman, N., Fraley, R. T., Beachy, R. N. 1987. *Plant Mol. Biol.* 9:315–324.
Lazzeri, 1995. *Methods Mol. Biol.,* 49:95–106

Lee, C. A. and Saier, M. H. Jr. 1983. *J. of Bacteriol.* 153:685–692.
Lee; Suh; Lee, 1989. *Korean J. Genet.,* 11(2):65–72
Levings, C. S., III. 1990. *Science* 250:942–947
Lichtenstein, C., Paszkowski, J., Hohn, B., in: *Homologous Recombination and Gene Silencing in Plants,* Ed. J. Paszkowski. Kluwer, Dordrecht, The Netherlands, 1994
Lieber and Strauss, 1995. *Mol. Cell. Biol.,* 15:540–551
Loomis, S. H., Carpenter, J. F., Anchordoguy, T. J., Crowe, J. H., and Branchini, B. R. 1989. *J. Expt. Zoology* 252:9–15.
Lorz et al., 1985. *Mol Gen Genet,* 199:178–182
Luo H., Lyznik, L. A., Gidoni D., Hodges, T. K. 2000. *Plant J.* Aug;23(3):423–430
Lyznik, L. A., Rao, K. V., Hodges, T. K. 1996. *Nucleic Acids Res,* Oct 1; 24(19):3784–9
Marcotte et al., 1988. *Nature,* 335:454–457.
Mariani, C., De Beuckeleer, M., Truettner, J., Leemans, J. and Goldberg, R. B. 1990. *Nature* 347:737–741.
McCabe, Martinell, 1993. *Bio-Technology,* 11(5):596–598
McCormac et al., 1998. *Euphytica,* v. 99 (1) p. 17–25
McElroy et al 1990. *Plant Cell,* 2:163
McElroy et al. 1991. *Molec. Gen. Genet.,* 231:150–160
*Methods in Enzymology,* 153, 292, 1987.
Michel and Westhof, 1990. *J Mol. Biol.,* 216:585–610
Moll, B., et al. 1990. *Mol. Gen. Genet.* 221:245
Mundy, J. and Chua, N. -H. 1988. *The EMBO J.* 7:2279–2286.
Murakami T., Anzai H., Imai S., Satoh A., Nagaoka K., Thompson C. J. 1986. *Mol Gen Genet* 205:42–50.
Murashige T., Skoog F. 1962. *Physiol Plant* 15:473–497.
Murdock et al. 1990. *Phytochemistry* 29:85–89.
Nagatani, Honda, Shimada, Kobayashi, 1997. *Biotech. Tech.,* 11(7):471–473
Napoli, Lemieux, Jorgensen, 1990. *Plant Cell,* 2:279–289
Niedz et al. 1995. *Plant Cell Reports,* 14:403
Odell, J. T., Nagy, F., Chua, N. H. 1985. *Nature* 313:810–812.
Ogawa et al., 1973. *Sci. Rep.,* 13:42–48
Omirulleh et al., 1993. *Plant Mol. Biol.,* 21(3):415–428
Ow, D. W., Wood, K. V., DeLuca, M., deWet, J. R., Helinski, D. R., Howell, S. H. 1986. *Science* 234:856–859.
Palukaitis et al., 1979. *Virology,* 99:145–151
Perlak F. J., Fuchs R. L., Dean D. A., McPherson S. L., and Fischhoff D. A., 1991. *Proc. Natl. Acad. Sci. USA* 88:3324–3328.
Perriman et al., 1992. *Gene,* 113:157–163
Peterhans, A., Schlupmann, H., Basse, C., Paxzkowski, J., 1990, *EMBO J.* 9:3437–45Phi-Van et al., 1990. *Mol. Cell. Biol.,* 10:2302–2307
Piatkowski, D., Schneider, K., Salamini, F. and Bartels, D. 1990. *Plant Physiol.* 94:1682–1688.
Potrykus I 1989. *Trends Biotechnol* 7:269–273.
Potrykus, I., Saul, M. W., Petruska, J., Paszkowski, J., Shillito, R. D. 1985. *Mol Gen Genet* 199:183–188
Prasher et al., 1985. *Biochem. Biophys. Res. Commun.,* 126(3):1259–1268
Prasher, et al. 1985. *Biochem. Biophys. Res. Commun.,* 126(3): 1259–1268.
Prody et al., 1986. *Science,* 231:1577–1580
Reed, R. H., Richardson, D. L., Warr, S. R. C., Stewart, W. D. P. 1984. *J. Gen. Microbiology* 130:1–4.
Reinhold-Hurek and Shub, 1992. *Nature,* 357:173–176
Reiss, B., Klemm, M., Kosak, H., Schell, J., 1996. *Proc. Natl. Acad. Sci. USA* 93:3094–3098
Rensburg et al., 1993. *J. Plant Physiol.,* 141:188–194
Rhodes et al., 1995. *Methods Mol. Biol.,* 55:121–131
Ritala et al., 1994. *Plant Mol. Biol.,* 24(2):317–325 Robbins, T. P., Walker, E. L.,
Kermicle, J. L., Alleman, M., Dellaporta, S. L. 1991. *Genetics* 129:271–283 Rogers et al., 1987. *Methods Enzymol.,* 153:253–277
Sambrook, J., Fritsch, E. F., and Maniatus, T. 1989. *Molecular Cloning, A Laboratory Manual* 2nd ed. Cold Spring Harbor Press, Cold Spring Harbor, N.Y.
Sengupta-Gopalan, 1985. *Proc. Natl. Acad. Sci. USA,* 82:3320
Shagan, T., Bar-Zvi, D. 1993. *Plant Physiol.* 101:1397–1398
Shalev, G., Sitrit, Y., Avivi-Ragolski, N., Lichtenstein, C., Levy, A. 1999. *Proc. Natl Acad. Sci. USA* 96:7398–7402.Shapiro, In: *Mobile Genetic Elements,* 1983.
Singsit et al., 1997. *Transgenic Res.,* 6(2):169–176
Skriver, K. and Mundy, J. 1990. *Plant Cell* 2:503–512.
Smith, Watson, Bird, Ray, Schuch, Grierson, 1990. *Mol. Gen. Genet.,* 224:447–481
Spencer, T. M., O'Brien, J. V., Start, W. G., Adams, T. R., Gordon-Kamm, W. J. and Lemaux, P. G. 1992. *Plant Molecular Biology* 18:201–210.
Stalker, D. M., McBride, K. E., and Malyj, L. 1988. *Science* 242:419–422
Stemberg et al. 1981. *Cold Spring Harbor Symposia on Quantitative Biology,* Vol. XLV 297
Stief et al, 1989. *Nature* 341:343
Stiefel et al. 1990. *The Plant Cell,* 2:785–793.
Stougaard, J. 1993. *The Plant Journal* 3:755–761.
Sullivan, Christensen, Quail, 1989. *Mol. Gen. Genet.,* 215 (3):431–440
Sutcliffe, J. G. 1978. *Proc Natl Acad Sci USA* 75:3737–3741
Swoboda, P., Hohn, B., Gal, S., 1993, *Mol. Gen. Genet.* 237:33–40
Swoboda, P., Gal, S., Hohn B., Puchta, H., 1994, Intrachromosomal homologous recombination in whole plants. *EMBO J.* 13:484–489
Symons, R. H. 1981. *Nucleic Acids Res* 9(23):6527–37.
Symons, R. H. 1992. *Annu. Rev. Biochem.,* 61:641–671
Szostak, J. W., Orr-Weaver, T. L., Rothstein, R. J., Stahl, F. W., 1983, The double-strand break repair model for recomgination. *Cell* 33:25–35
Tarczynski, M. C., Jensen, R. G., and Bohnert, H. J. 1993. *Science* 259:508–510.
Tarczynski, M. C., Jensen, R. G., and Bohnert, H. J. 1992. *Proc. Natl. Acad. Sci. USA,* 89:2600
Thillet, J., Absil, J., Stone, S. R., Pictet, R. 1988. *J Biol Chem* 263:12500–12508.
Thompson et al, 1995. *Euphytica,* 85(1–3):75–80
Thompson et al., 1987. *The EMBO Journal,* 6(9):2519–2523
Tingay et al., 1997. *The Plant Journal* v. 11 (6) p.1369–1376
Tomes et al., 1990. *Plant. Mol. Biol.* 14(2):261–268
Torbet, Rines, Somers, 1998. *Crop Science,* 38(1):226–231
Torbet, Rines, Somers, 1995. *Plant Cell Reports,* 14(10): 635–640
Toriyama et al., 1986. *Theor Appl. Genet.,* 73:16
Tovar and Lichtenstein, 1992. *The Plant Cell* 4:319–332.
Tsukada; Kusano; Kitagawa, 1989. *Plant Cell Physiol.,* 30(4)599–604
Twell D., Klein T. M., Fromm M. E., McCormick S. 1989. *Plant Physiol* 91:1270–1274.
Uchimiya et al., 1986. *Mol. Gen. Genet.,* 204:204–207.
Ugaki et al. 1991. *Nucl Acid Res,* 19:371–377.
Van der Krol et al., 1990. *Plant Cell,* 2:291–99
Van Eck; Blowers; Earle, 1995. *Plant Cell Reports,* 14(5): 299–304
Vasil, V., Clancy, M., Ferl, R. J., Vasil, I. K., Hannah, L. C. 1989. *Plant Physiol.* 91:1575–1579.

Viet, B., Vollbrecht, E., Mathem, J., Hake, S. 1990. *Genetics* 125:623–631.Vernon, D. M. and Bohnert, H. J. 1992. *The EMBO J.*11:2077–2085.

Walker, J. C., Howard, E. A., Dennis, E. S., Peacock, W. J 1987. *Proc. Natl. Acad. Sci. USA* 84:6624–6628.

Wang, Y., Zhang, W., Cao, J., McEhoy, D. and Ray Wu. 1992. *Molecular and Cellular Biology* 12:3399–3406.

Watrud et al, In: *Engineered Organisms and the Environment*, 1985.

Withers L. A., King P. J. 1979. *Plant Physiol* 64:675–678.

Wolter, F., Schmidt, R., and Heinz, E. 1992. *The EMBO J.* 11:4685–4692.

Xiang and Guerra, Plant Physiol., 1993. 102:287–293

Xu et al., *Plant Physiol.*, 1996. 110:249–257

Yamada et al, 1986. *Plant Cell Rep.*, 4:85

Yamaguchi-Shinozaki, K., Koizumi, M., Urao, S., Shinozaki, K. 1992. *Plant Cell Physiol.* 33:217–224.

Yang, N. S., Russell, D. 1990. *Proc. Natl. Acad. Sci. USA* 87:4144–4148.

Yuan and Altman, 1994. *Science,* 263:1269–1273

Yuan et al., 1992. *Proc. Natl. Acad. Sci. USA,* 89:8006–8010

Zhang et al., 1997. *Mol Biotechnol.*, 8:223–31

Zheng and Edwards, 1990. *J Gen. Virol.*, 71:1865–1868

Zhou et al., 1993. *Plant Cell Reports,* 12(11). 612–616

Zubko, E., Scutt, C., Meyer, P., 2000,. *Nature Biotechnology* 18:442–445

What is claimed is:

1. A method of preparing a marker-free fertile transgenic plant having all marker gene sequences removed from transgene insertions comprising:

a) obtaining a first fertile transgenic plant homozygous for a transgene insertion DNA sequence, wherein the transgene insertion DNA sequence comprises at least one marker gene DNA sequence flanked by directly repeated DNA sequences, wherein said directly repeated sequences are not recognized by a site-specific recombinase enzyme;

b) obtaining a plurality of progeny of any generation of the first fertile transgenic plant; and c) selecting a progeny fertile transgenic plant wherein all marker gene sequences are deleted.

2. The method of claim 1 wherein the marker gene comprises a selectable marker gene or reporter gene.

3. The method of claim 2 wherein the selectable marker gene comprises a bar, nptII, or a glyphosate resistant EPSPS enzyme gene.

4. The method of claim 2 wherein the reporter gene comprises a uidA gene, a gfp gene or an R-locus gene.

5. The method of claim 1 wherein the plant is a monocot.

6. The method of claim 5 wherein the monocot plant is a maize, barley, sorghum, wheat, rye or rice plant.

7. The method of claim 1 wherein the plant is a dicot.

8. The method of claim 7 wherein the dicot plant is a soybean, cotton, canola, or potato plant.

9. The method of claim 1 wherein said plant is maize and the plurality of progeny plants are obtained by self pollination.

10. The method of claim 1 wherein said plant is maize and the plurality of progeny plants are obtained by outcrossing to produce hybrid progeny.

11. The method of claim 1 wherein said plant is maize and the plurality of progeny plants are obtained by inbreeding to produce inbred plants.

12. The method of claim 1 wherein the marker gene is deleted at a frequency of at least 0.1%.

13. The method of claim 1 wherein the marker gene is deleted at a frequency of at least 0.6%.

14. The method of claim 1 wherein the marker gene is deleted at a frequency of at least 2%.

* * * * *